US009480793B2

(12) United States Patent
Mhatre et al.

(10) Patent No.: US 9,480,793 B2
(45) Date of Patent: *Nov. 1, 2016

(54) OCCLUSION SENSING FOR AN INFUSION PUMP

(71) Applicant: Bigfoot Biomedical, Inc., Milpitas, CA (US)

(72) Inventors: Amit Mhatre, Sunnyvale, CA (US); Jian Yao Wu, San Jose, CA (US); Mitchell Wenger, Ross, CA (US); Steven M. Friedman, San Francisco, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/830,841

(22) Filed: Aug. 20, 2015

(65) Prior Publication Data
US 2015/0352279 A1 Dec. 10, 2015

Related U.S. Application Data

(60) Continuation of application No. 14/506,933, filed on Oct. 6, 2014, now abandoned, which is a continuation of application No. 13/008,529, filed on Jan. 18, 2011, now Pat. No. 8,852,141, which is a division of application No. 11/751,383, filed on May 21, 2007, now Pat. No. 7,892,199.

(51) Int. Cl.
*A61M 5/168* (2006.01)
*A61M 5/14* (2006.01)
(Continued)

(52) U.S. Cl.
CPC ....... *A61M 5/16831* (2013.01); *A61M 5/1413* (2013.01); *A61M 5/14244* (2013.01);
(Continued)

(58) Field of Classification Search
CPC ......... A61M 5/16831; A61M 5/1413; A61M 5/14244; A61M 5/14566; A61M 5/16854; A61M 2005/16863; A61M 2005/16868; A61M 2005/31518; A61M 2205/0244; A61M 2205/18; A61M 2205/3306; G01L 9/0077
USPC .............. 604/65–67, 131, 151; 128/DIG. 12, 128/DIG. 13
See application file for complete search history.

(56) References Cited

U.S. PATENT DOCUMENTS 2,605,765 A 8/1952 Kollsman
3,040,583 A * 6/1962 Post ............................... 73/705
(Continued)

FOREIGN PATENT DOCUMENTS

CA 2543545 5/2005
DE 196 27 619 A 1/1998
(Continued)

OTHER PUBLICATIONS

Accu-Chek Spirit, "Pump Therapy Made for You," Roche, 2006, 6 pages.
(Continued)

*Primary Examiner* — Manuel Mendez
(74) *Attorney, Agent, or Firm* — Fish & Richardson P.C.

(57) ABSTRACT

Some embodiments of an infusion pump system may include an occlusion sensor that can be used to detect when an occlusion exists in the fluid path between the medicine reservoir and the infusion site on the user's skin. Such an occlusion may occur, for example, when the fluid flow line (e.g., a cannula, infusion set tubing, or the like) is kinked. If the medicine dispensation path to the user is occluded, the user may receive no dosage or a lower dosage of the medicine. As such, the occlusion sensor can be used to indicate when the fluid is flowing or not flowing, thereby permitting the infusion pump system to communicate an alarm to the user if an occlusion exists.

24 Claims, 23 Drawing Sheets

(51) Int. Cl.
*A61M 5/142* (2006.01)
*A61M 5/145* (2006.01)
*G01L 9/00* (2006.01)
*A61M 5/315* (2006.01)

(52) U.S. Cl.
CPC ..... *A61M5/14566* (2013.01); *A61M 5/16854* (2013.01); *G01L 9/0077* (2013.01); *A61M 2005/16863* (2013.01); *A61M 2005/16868* (2013.01); *A61M 2005/31518* (2013.01); *A61M 2205/0244* (2013.01); *A61M 2205/18* (2013.01); *A61M 2205/3306* (2013.01)

(56) References Cited

U.S. PATENT DOCUMENTS

| | | | |
|---|---|---|---|
| 3,563,090 A * | 2/1971 | Deltour | 73/861.41 |
| 3,886,938 A | 6/1975 | Szabo et al. | |
| 4,077,405 A | 3/1978 | Haerten et al. | |
| 4,231,368 A | 11/1980 | Becker | |
| 4,265,241 A | 5/1981 | Portner et al. | |
| 4,300,554 A | 11/1981 | Hessberg et al. | |
| 4,313,439 A | 2/1982 | Babb et al. | |
| 4,387,734 A | 6/1983 | Borsanyi | |
| 4,398,908 A | 8/1983 | Siposs | |
| 4,435,173 A | 3/1984 | Siposs et al. | |
| 4,443,218 A | 4/1984 | DeCant, Jr. et al. | |
| 4,493,704 A | 1/1985 | Beard et al. | |
| 4,529,401 A | 7/1985 | Leslie et al. | |
| 4,681,569 A | 7/1987 | Coble et al. | |
| 4,838,857 A | 6/1989 | Strowe et al. | |
| 4,850,817 A | 7/1989 | Nason et al. | |
| 5,045,064 A | 9/1991 | Idriss | |
| 5,088,981 A | 2/1992 | Howson et al. | |
| 5,088,990 A | 2/1992 | Hivale et al. | |
| 5,189,240 A * | 2/1993 | Kawashima | 84/724 |
| 5,190,522 A | 3/1993 | Wojcicki et al. | |
| 5,225,763 A | 7/1993 | Krohn et al. | |
| 5,250,027 A | 10/1993 | Lewis et al. | |
| 5,261,882 A | 11/1993 | Sealfon et al. | |
| 5,314,412 A | 5/1994 | Rex | |
| 5,335,994 A | 8/1994 | Weynant Nee Girones | |
| 5,338,157 A | 8/1994 | Blomquist | |
| 5,342,180 A | 8/1994 | Daoud | |
| 5,389,078 A | 2/1995 | Zalesky et al. | |
| 5,395,340 A | 3/1995 | Lee | |
| 5,411,487 A | 5/1995 | Castagna | |
| 5,415,641 A | 5/1995 | Yerlikaya et al. | |
| 5,429,602 A * | 7/1995 | Hauser | 604/65 |
| 5,545,143 A | 8/1996 | Fischell et al. | |
| 5,551,850 A | 9/1996 | Williamson et al. | |
| 5,569,186 A | 10/1996 | Lord et al. | |
| 5,626,566 A | 5/1997 | Petersen et al. | |
| 5,637,095 A | 6/1997 | Nason et al. | |
| 5,665,065 A | 9/1997 | Colman et al. | |
| 5,718,562 A | 2/1998 | Lawless | |
| 5,741,216 A | 4/1998 | Hemmingsen et al. | |
| 5,766,155 A | 6/1998 | Hyman et al. | |
| 5,772,635 A | 6/1998 | Dastur et al. | |
| 5,814,015 A * | 9/1998 | Gargano et al. | 604/67 |
| 5,816,306 A | 10/1998 | Giacomel | |
| 5,852,803 A | 12/1998 | Ashby, III et al. | |
| 5,853,386 A * | 12/1998 | Davis et al. | 604/65 |
| 5,858,001 A | 1/1999 | Tsals et al. | |
| 5,919,167 A | 7/1999 | Mulhauser | |
| 5,925,018 A | 7/1999 | Ungerstedt | |
| 5,928,201 A | 7/1999 | Poulsen et al. | |
| 5,947,934 A | 9/1999 | Hansen et al. | |
| 5,951,530 A | 9/1999 | Steengaard et al. | |
| 5,957,889 A | 9/1999 | Poulsen et al. | |
| 5,984,894 A | 11/1999 | Poulsen et al. | |
| 5,984,897 A | 11/1999 | Petersen et al. | |
| 5,997,475 A | 12/1999 | Bortz | |
| 6,003,736 A | 12/1999 | Ljunggren | |
| 6,010,485 A | 1/2000 | Buch-Rasmussen et al. | |
| 6,033,377 A | 3/2000 | Rasmussen et al. | |
| 6,045,537 A | 4/2000 | Klitmose | |
| 6,074,372 A | 6/2000 | Hansen | |
| 6,083,206 A | 7/2000 | Molko | |
| 6,110,149 A | 8/2000 | Klitgaard et al. | |
| 6,156,014 A | 12/2000 | Petersen et al. | |
| 6,171,276 B1 | 1/2001 | Lippe et al. | |
| 6,231,540 B1 | 5/2001 | Smedegaard | |
| 6,248,067 B1 | 6/2001 | Causey, III et al. | |
| 6,248,090 B1 | 6/2001 | Jensen et al. | |
| 6,248,093 B1 | 6/2001 | Moberg | |
| 6,277,098 B1 | 8/2001 | Klitmose et al. | |
| 6,302,855 B1 | 10/2001 | Lav et al. | |
| 6,302,869 B1 | 10/2001 | Klitgaard | |
| 6,368,314 B1 | 4/2002 | Kipfer et al. | |
| 6,375,638 B2 | 4/2002 | Nason et al. | |
| 6,379,339 B1 | 4/2002 | Klitgaard et al. | |
| 6,381,496 B1 | 4/2002 | Meadows et al. | |
| 6,404,098 B1 | 6/2002 | Kayama et al. | |
| 6,427,088 B1 | 7/2002 | Bowman, IV et al. | |
| 6,436,072 B1 | 8/2002 | Kullas et al. | |
| 6,461,331 B1 | 10/2002 | Van Antwerp | |
| 6,474,219 B2 | 11/2002 | Klitmose et al. | |
| 6,485,461 B1 | 11/2002 | Mason et al. | |
| 6,508,788 B2 | 1/2003 | Preuthun | |
| 6,524,280 B2 | 2/2003 | Hansen et al. | |
| 6,533,183 B2 | 3/2003 | Aasmul et al. | |
| 6,537,251 B2 | 3/2003 | Klitmose | |
| 6,540,672 B1 | 4/2003 | Simonsen et al. | |
| 6,544,229 B1 | 4/2003 | Danby et al. | |
| 6,547,764 B2 | 4/2003 | Larsen et al. | |
| 6,551,276 B1 | 4/2003 | Mann et al. | |
| 6,554,798 B1 | 4/2003 | Mann et al. | |
| 6,554,800 B1 | 4/2003 | Nezhadian et al. | |
| 6,558,320 B1 | 5/2003 | Causey, III et al. | |
| 6,558,351 B1 | 5/2003 | Steil et al. | |
| 6,562,001 B2 | 5/2003 | Lebel et al. | |
| 6,562,011 B1 | 5/2003 | Buch-Rasmussen et al. | |
| 6,564,105 B2 | 5/2003 | Starkweather et al. | |
| 6,569,126 B1 | 5/2003 | Poulsen et al. | |
| 6,571,128 B2 | 5/2003 | Lebel et al. | |
| 6,577,899 B2 | 6/2003 | Lebel et al. | |
| 6,582,404 B1 | 6/2003 | Klitgaard et al. | |
| 6,585,644 B2 | 7/2003 | Lebel et al. | |
| 6,585,699 B2 | 7/2003 | Ljunggreen et al. | |
| 6,589,229 B1 | 7/2003 | Connelly et al. | |
| 6,605,067 B1 | 8/2003 | Larsen | |
| 6,613,019 B2 | 9/2003 | Munk | |
| 6,641,533 B2 | 11/2003 | Causey, III et al. | |
| 6,648,821 B2 | 11/2003 | Lebel et al. | |
| 6,650,951 B1 | 11/2003 | Jones et al. | |
| 6,656,158 B2 | 12/2003 | Mahoney et al. | |
| 6,656,159 B2 | 12/2003 | Flaherty | |
| 6,659,948 B2 | 12/2003 | Lebel et al. | |
| 6,659,978 B1 | 12/2003 | Kasuga et al. | |
| 6,659,980 B2 | 12/2003 | Moberg et al. | |
| 6,663,602 B2 | 12/2003 | Møller | |
| 6,668,196 B1 | 12/2003 | Villegas et al. | |
| 6,669,669 B2 | 12/2003 | Flaherty et al. | |
| 6,687,546 B2 | 2/2004 | Lebel et al. | |
| 6,690,192 B1 | 2/2004 | Wing | |
| 6,691,043 B2 | 2/2004 | Ribeiro, Jr. | |
| 6,692,457 B2 | 2/2004 | Flaherty | |
| 6,692,472 B2 | 2/2004 | Hansen et al. | |
| 6,694,191 B2 | 2/2004 | Starkweather et al. | |
| 6,699,218 B2 | 3/2004 | Flaherty et al. | |
| 6,702,779 B2 | 3/2004 | Connelly et al. | |
| 6,715,516 B2 | 4/2004 | Ohms et al. | |
| 6,716,198 B2 | 4/2004 | Larsen | |
| 6,723,072 B2 | 4/2004 | Flaherty et al. | |
| 6,733,446 B2 | 5/2004 | Lebel et al. | |
| 6,736,796 B2 | 5/2004 | Shekalim | |
| 6,740,059 B2 | 5/2004 | Flaherty | |
| 6,740,072 B2 | 5/2004 | Starkweather et al. | |
| 6,740,075 B2 | 5/2004 | Lebel et al. | |
| 6,744,350 B2 | 6/2004 | Blomquist | |
| 6,749,587 B2 | 6/2004 | Flaherty | |
| 6,752,787 B1 | 6/2004 | Causey, III et al. | |
| 6,758,810 B2 | 7/2004 | Lebel et al. | |

(56) References Cited

U.S. PATENT DOCUMENTS

| | | |
|---|---|---|
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman, IV et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larsen et al. |
| 7,014,625 B2 | 3/2006 | Bengtsson |
| 7,018,360 B2 | 3/2006 | Flaherty et al. |
| 7,025,743 B2 | 4/2006 | Mann |
| 7,029,455 B2 | 4/2006 | Flaherty |
| 7,052,251 B2 | 5/2006 | Nason et al. |
| 7,054,836 B2 | 5/2006 | Christensen et al. |
| 7,104,972 B2 | 9/2006 | Møller et al. |
| 7,128,727 B2 | 10/2006 | Flaherty et al. |
| 7,133,329 B2 | 11/2006 | Skyggebjerg et al. |
| 7,232,423 B2 | 6/2007 | Mernoe |
| 7,327,273 B2 | 2/2008 | Hung et al. |
| 7,789,859 B2 | 9/2010 | Estes et al. |
| 7,892,199 B2 | 2/2011 | Mhatre et al. |
| 8,852,141 B2 | 10/2014 | Mhatre et al. |
| 2001/0041869 A1 | 11/2001 | Causey, III et al. |
| 2001/0056262 A1 | 12/2001 | Cabiri |
| 2002/0004651 A1 | 1/2002 | Ljnggreen et al. |
| 2002/0007154 A1 | 1/2002 | Hansen et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0167035 A1 | 9/2003 | Flaherty et al. |
| 2003/0198558 A1 | 10/2003 | Nason et al. |
| 2003/0199825 A1 | 10/2003 | Flaherty |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0171983 A1 | 9/2004 | Sparks et al. |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0065760 A1 | 3/2005 | Murtfeldt et al. |
| 2005/0090808 A1 | 4/2005 | Malave et al. |
| 2005/0090851 A1 | 4/2005 | Devlin |
| 2005/0095063 A1 | 5/2005 | Fathallah |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0234404 A1 | 10/2005 | Vilks et al. |
| 2005/0238507 A1 | 10/2005 | DiIanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0151545 A1 | 7/2006 | Imhof et al. |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2007/0073228 A1 | 3/2007 | Mernoe et al. |
| 2007/0073236 A1 | 3/2007 | Mernoe et al. |
| 2007/0088271 A1 | 4/2007 | Richards |
| 2007/0106218 A1 | 5/2007 | Yodfat et al. |
| 2007/0124002 A1 | 5/2007 | Estes et al. |
| 2007/0141786 A1 | 6/2007 | Kawagoe et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2007/0239116 A1 | 10/2007 | Follman et al. |
| 2008/0051716 A1 | 2/2008 | Stutz |
| 2008/0097381 A1 | 4/2008 | Moberg et al. |
| 2008/0208627 A1 | 8/2008 | Skyggebjerg |

FOREIGN PATENT DOCUMENTS

| | | |
|---|---|---|
| DE | 102 36 669 | 2/2004 |
| EP | 0 062 974 | 10/1982 |
| EP | 0 496 141 | 7/1992 |
| EP | 0 612 004 | 8/1994 |
| EP | 0 580 723 | 10/1995 |
| EP | 0 275 213 | 7/1998 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| EP | 1 818 664 | 8/2007 |
| FR | 2 585 252 | 1/1987 |
| GB | 747 701 | 4/1956 |
| GB | 2 218 831 | 11/1989 |
| WO | WO 90/15928 | 12/1990 |
| WO | WO 97/21457 | 6/1997 |
| WO | WO 98/04301 | 2/1998 |
| WO | WO 98/11927 | 3/1998 |
| WO | WO 98/57683 | 12/1998 |
| WO | WO 99/21596 | 5/1999 |
| WO | WO 99/39118 | 8/1999 |
| WO | WO 99/48546 | 9/1999 |
| WO | WO 01/72360 | 10/2001 |
| WO | WO 01/91822 | 12/2001 |

(56) References Cited

FOREIGN PATENT DOCUMENTS

| WO | WO 01/91833 | 12/2001 |
|---|---|---|
| WO | WO 02/40083 | 5/2002 |
| WO | WO 02/057627 | 7/2002 |
| WO | WO 02/068015 | 9/2002 |
| WO | WO 02/084336 | 10/2002 |
| WO | WO 02/100469 | 12/2002 |
| WO | WO 03/026726 | 4/2003 |
| WO | WO 03/103763 | 12/2003 |
| WO | WO 2004/056412 | 7/2004 |
| WO | WO 2004/110526 | 12/2004 |
| WO | WO 2005/002652 | 1/2005 |
| WO | WO 2005/039673 | 5/2005 |
| WO | WO 2005/072794 | 8/2005 |
| WO | WO 2005/072795 | 8/2005 |
| WO | WO 2006/067217 | 6/2006 |
| WO | WO 2006/097453 | 9/2006 |
| WO | WO 2006/105792 | 10/2006 |
| WO | WO 2006/105793 | 10/2006 |
| WO | WO 2006/105794 | 10/2006 |
| WO | WO 2007/141786 | 12/2007 |

OTHER PUBLICATIONS

Collins and Lee, "Microfluidic flow transducer based on the measurement of electrical admittance," *Lab Chip*, 2004, 4:7-10.

Debiotech News Release, "Debiotech reveals its new miniaturized Disposable Insulin Nanopump™ for Diabetes therapy," available at http://www.debiotech.com/news/nw_159.html Apr. 24, 2006, 3 pages.

European Office Action issued in EP Application No. 08755970.4, dated Aug. 16, 2013, 5 pages.

International Preliminary Report on Patentability, PCT/US2008064244, mailed Dec. 3, 2009, (9 pages).

International Search Report & Written Opinion PCT/US2008064244, mailed Sep. 16, 2008, 18 pages.

Medtronic News Release, "Medtronic Receives FDA Approval for World's First Insulin Pump with Real-time Continuous Glucose Monitoring," Apr. 13, 2006, 3 pages.

OmniPod Insulin Management System—Investor Relations—Press Release, Feb. 1, 2005, http://investors.insulet.com/phoenix.zhtml?c=209336&p=irol-newsArticle&ID=988708&highlight=1 page.

OmniPod Quick Start Guide, 2007, 2 pages.

Patent Abstracts of Japan, vol. 1999, No. 04, and JP 11 010036, Apr. 30, 1999 and Jan. 19, 1999, Toray Ind. Inc.

The Medtronic Diabetes Connection, 2006, 6 pages.

Xilas Temp Touch, "The latest in high-tech and convenient devices," DOCNews, vol. 2, No. 7, Jul. 1, 2005, http://docnews.diabetesjournals.ord/cgi/content/full/2/7/13, 3 pages.

\* cited by examiner

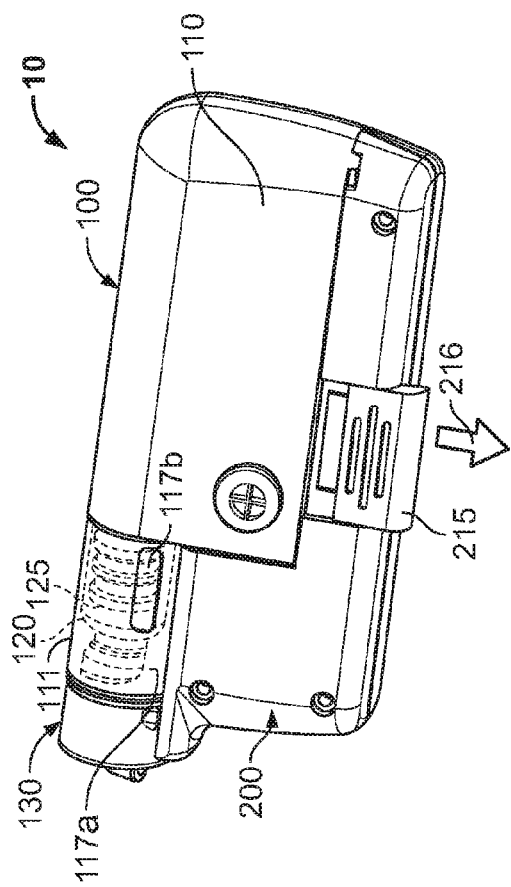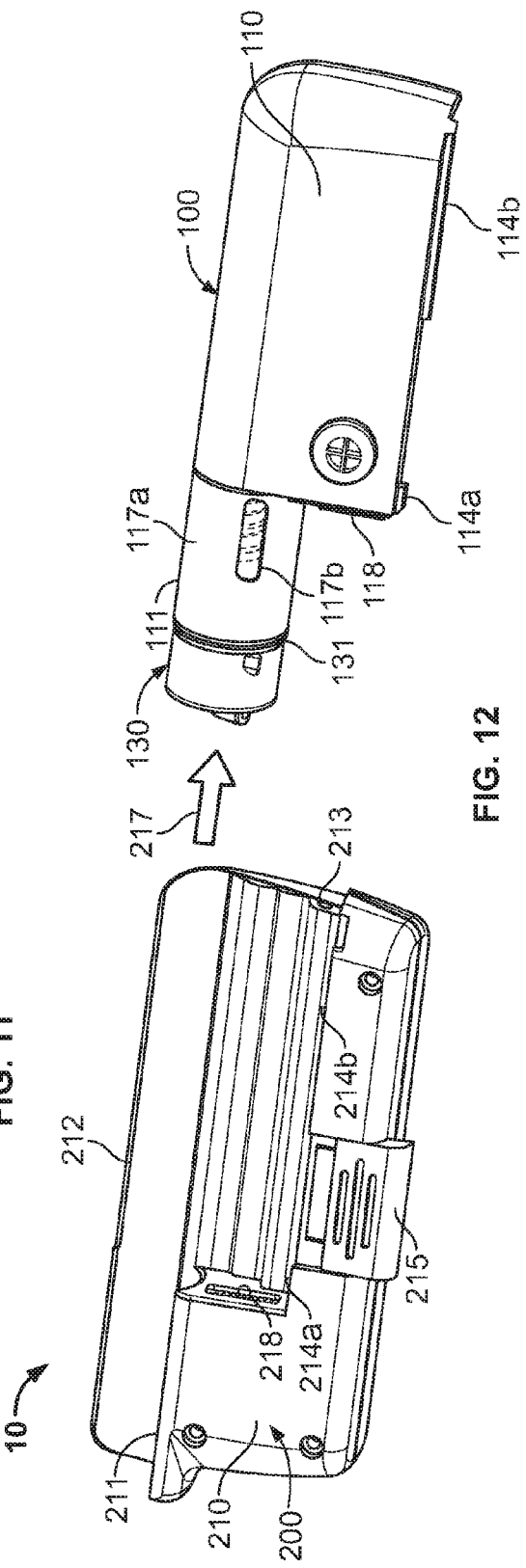
FIG. 11
FIG. 12

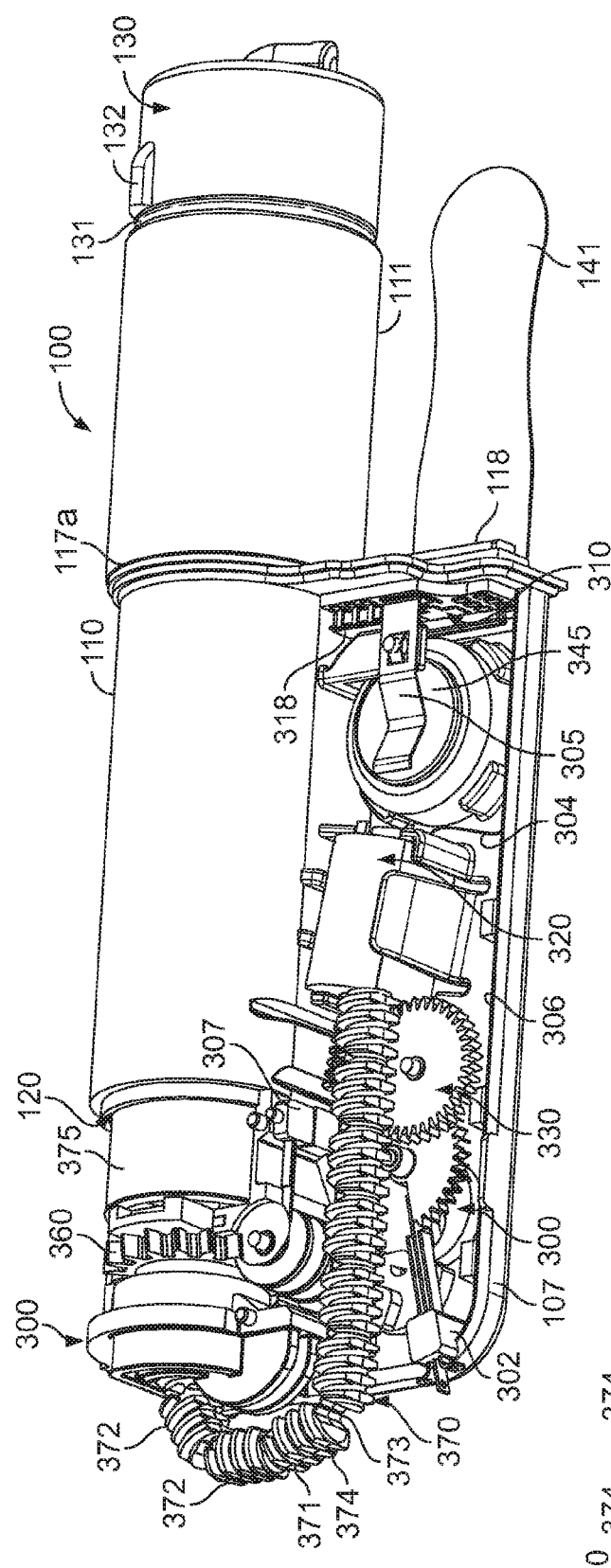
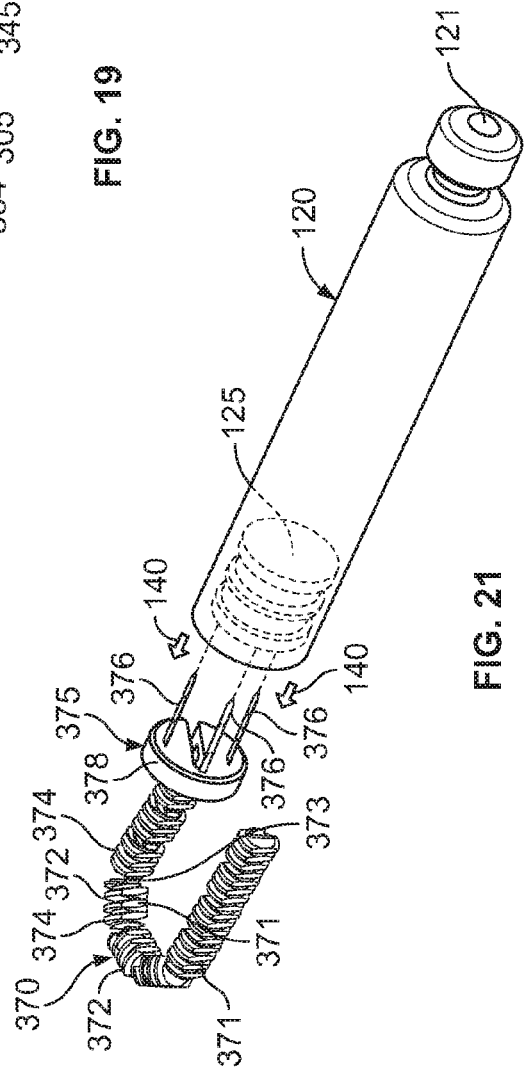
FIG. 19
FIG. 21

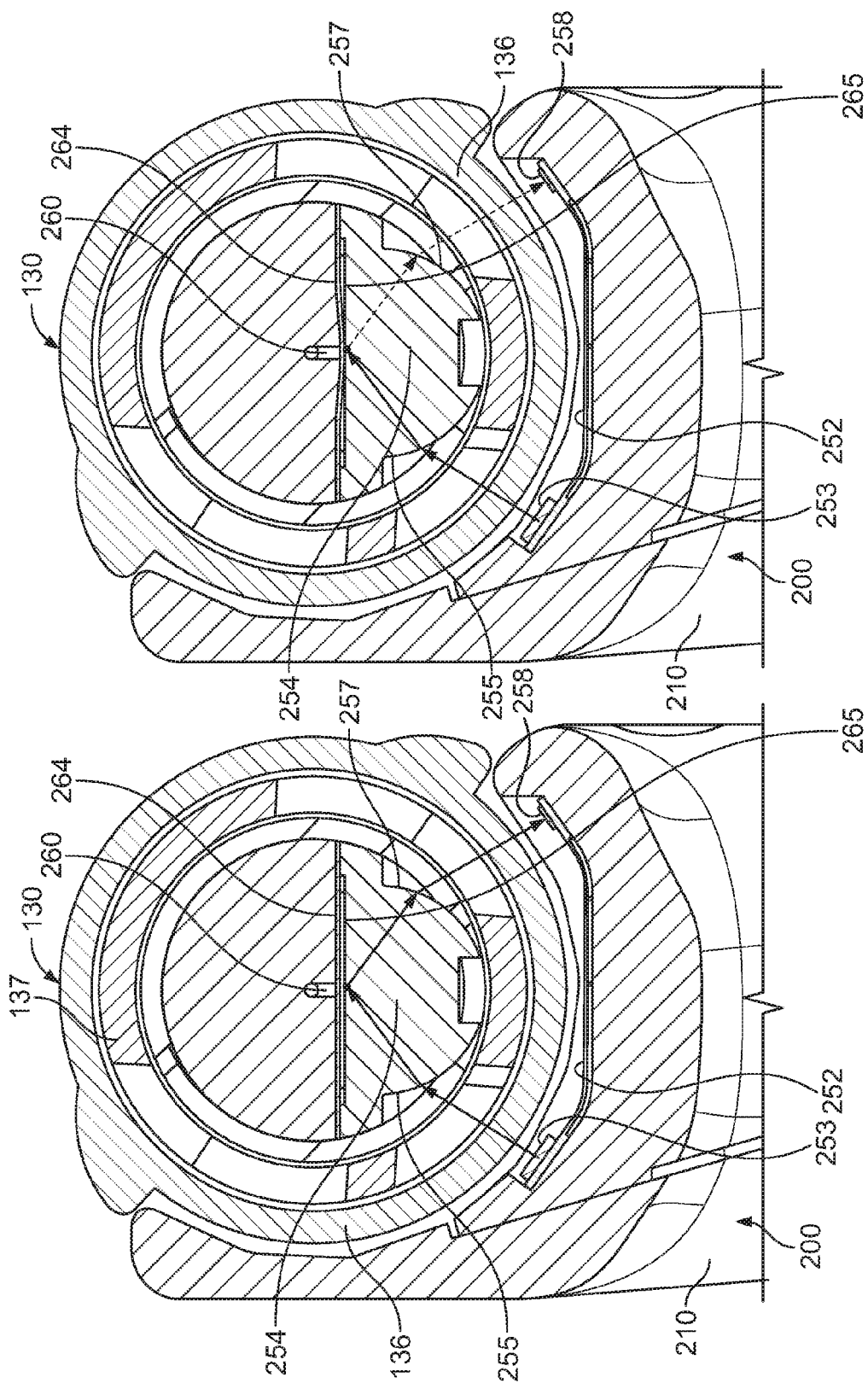

OCCLUSION SENSING FOR AN INFUSION PUMP

CLAIM OF PRIORITY

This is a continuation application of U.S. patent Ser. No. 14/506,933 filed on Oct. 6, 2014, which is a continuation of U.S. patent Ser. No. 13/008,529 (now U.S. Pat. No. 8,852, 141) filed on Jan. 18, 2011, which is a division of U.S. patent Ser. No. 11/751,383 (now U.S. Pat. No. 7,892,199) filed on May 21, 2007, the contents of these previous applications being incorporated herein by reference.

TECHNICAL FIELD

This document relates to delivery of fluid from an infusion pump system, such as the delivery of medicine from a wearable infusion pump system.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

SUMMARY

Some embodiments of an infusion pump system may include an occlusion sensor that can be used to detect when an occlusion exists in the fluid path between the medicine reservoir and the infusion site on the user's skin. Such an occlusion may occur, for example, when the fluid flow line (e.g., a cannula, infusion set tubing, or the like) is kinked. If the medicine dispensation path to the user is occluded, the user may receive no dosage or a lower dosage of the medicine. As such, the occlusion sensor can be used to indicate when the fluid is flowing or not flowing, thereby permitting the infusion pump system to communicate an alarm to the user if an occlusion exists.

Particular embodiments include an occlusion sensor system for an infusion pump system including a reusable controller device that is removably attachable to a disposable single-use pump device. The occlusion sensor system may include a light emitter and a light sensor arranged in the reusable controller device. The light emitter and the light sensor may be in electrical communication with control circuitry of the reusable controller device. The occlusion sensor system may also include a light transmissive member arranged in the disposable single-use pump device. The light transmissive member may be aligned with the light emitter and the light sensor when the reusable controller device is removably attached to a disposable single-use pump device. The light sensor may receive light from the light emitter that is internally reflected by the light transmissive member.

Some embodiments include methods for detecting an occlusion in a flow path from an infusion pump system. One method can include activating a light emitter arranged in a controller device housing to direct light outside of the controller device housing and into a light transmissive member arranged in a pump device that is removably attached to the controller device housing. The method may also include receiving signals from a light sensor arranged in the controller device housing. The signals from the light sensor may be generated in response to the light sensor receiving light from the light emitter that is internally reflected by the light transmissive member. The method may further include determining if an occlusion exists in a flow path based at least in part on the signals received from the light sensor.

Certain embodiments include an infusion pump system for dispensing medicine. The infusion pump system can include a pump device and a removable controller device. The pump device may include a drive system to dispense a medicine from the pump device and a cap having a fluid channel through which the medicine is dispensed. The cap may have a light transmissive member arranged proximate to the fluid channel. The removable controller device may include control circuitry to communicate with the drive system of the pump device when the pump device is removably attached to the controller device. The removable controller device may also include a light emitter and a light sensor that are in electrical communication with control circuitry. The light sensor may receive light from the light emitter that is internally reflected by the light transmissive member in the cap.

Some embodiments include an occlusion sensor system for detecting an occlusion in a flow path from an insulin infusion pump system. The occlusion sensor system may include a fluid channel defined in a cap of a pump device. The fluid channel may be at least a portion of an insulin flow path. The occlusion sensor system may also include a flexible membrane in the cap adjacent to the fluid channel so as to define at least a portion of a wall of the fluid channel. The occlusion sensor system may further include an air cavity in the cap adjacent to the flexible membrane and opposite the fluid channel. Also, the occlusion sensor system may include a light transmissive member in the cap adjacent to the air cavity. The light transmissive member may be arranged opposite the flexible membrane such that fluid pressure in the fluid channel above a threshold value causes the flexible membrane to deform into the air cavity and toward the light transmissive member. The occlusion sensor system may further include a light emitter and a light sensor arranged in a controller device and outside of the pump device. The light emitter and the light sensor may be aligned with the cap of the pump device when the controller device is removably attached to the pump device.

Some or all of the embodiments described herein may provide one or more of the following advantages. First, the infusion pump system may include an occlusion sensor configuration that reliably detects occlusions in the medicine flow path extending from the pump device to the user. As such, the occlusion sensor feature can provide notice to the user if he or she is receiving no dosage or a lower dosage of the medicine due to an occlusion in the medicine flow path.

Second, some embodiments of the infusion pump system may include a reusable controller device that is removably attachable to a disposable single-use pump device. In such circumstances, some of the relatively higher-cost components of the occlusion sensor system can be housed in the reusable controller device, thereby permitting these components to be used over a longer period of time with a series of successive pump devices.

Third, because some components of the occlusion sensor system are housed in the controller device, the sensor signals can be readily communicated to the control circuitry to determine if an occlusion exists. If so, the user interface of the controller device can be used to promptly alert the user of the problem.

Fourth, some embodiments of the pump device may be attached to the controller device so that a user can readily monitor infusion pump operation by simply viewing the user interface connected to the pump device. In these circumstances, the user may activate and control the pump device without the requirement of locating and operating a separate monitoring module.

Fifth, some embodiments of the infusion pump system may be configured to be portable, wearable, and (in some circumstances) concealable. For example, a user can conveniently wear the infusion pump system on the user's skin under clothing or can carry the pump device in the user's pocket (or other portable location) while receiving the medicine dispensed from the pump device.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 11-12 are perspective views of a pump device being detached from a controller device, in accordance with some embodiments.

FIG. 19 is a perspective view of a portion of the pump device of FIG. 18.

FIG. 21 is an exploded perspective view of a medicine cartridge and a flexible piston rod, in accordance with some embodiments.

FIGS. 30-31 are cross-sectional views of the occlusion sensor of FIGS. 28-29.

Like reference symbols in the various drawings indicate like elements.

DETAILED DESCRIPTION OF ILLUSTRATIVE EMBODIMENTS

Figure 1:
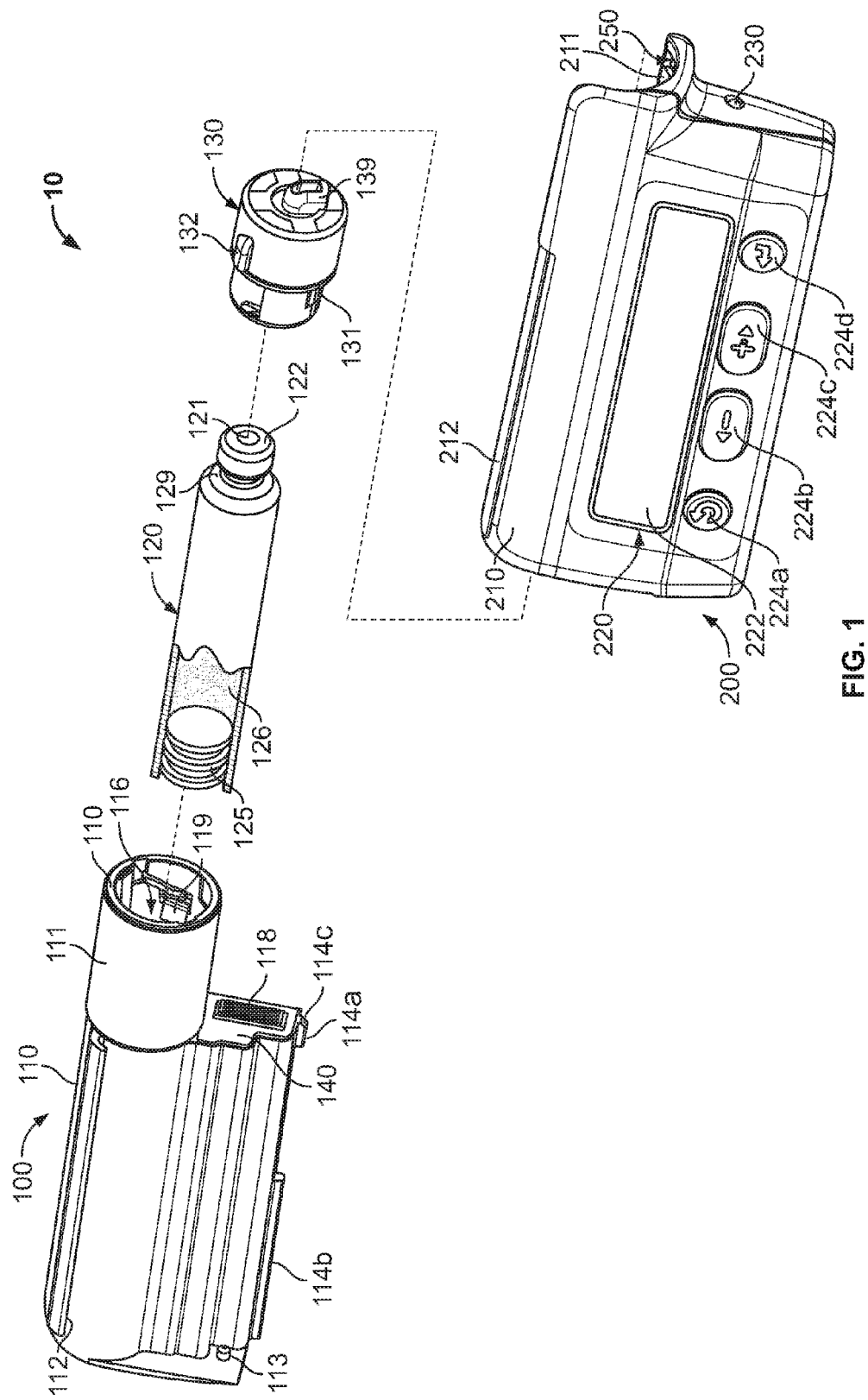
FIG. 1 is a perspective view of an infusion pump system in accordance with some embodiments, in accordance with some embodiments.
Figure 2:
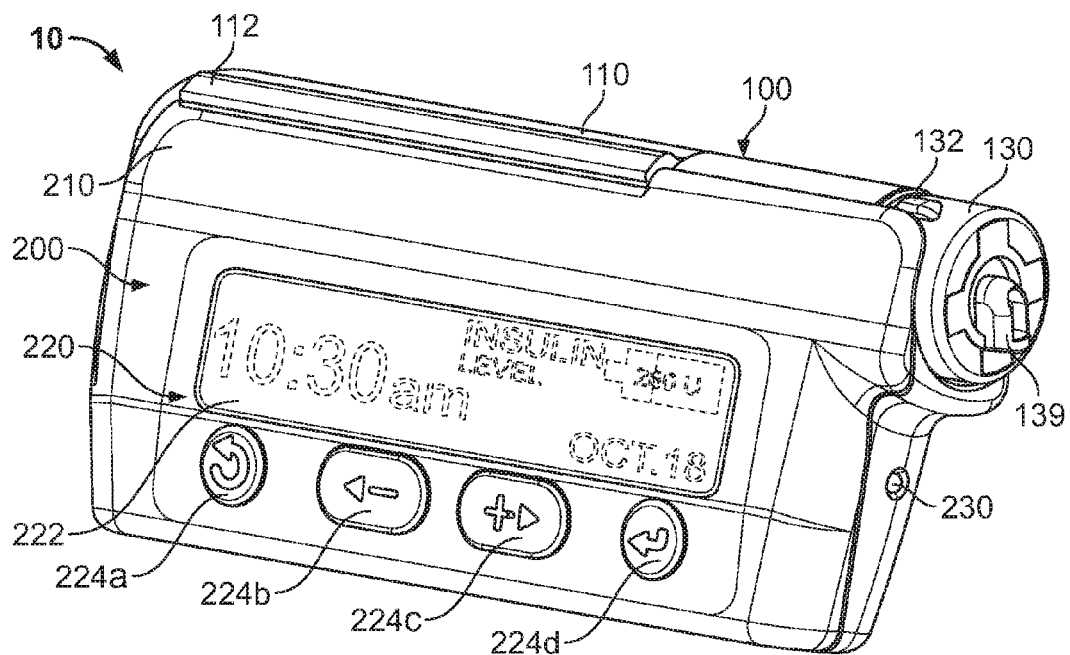
FIG. 2 is a perspective view of the infusion pump system of FIG. 1 in an assembled state.
Figure 3:
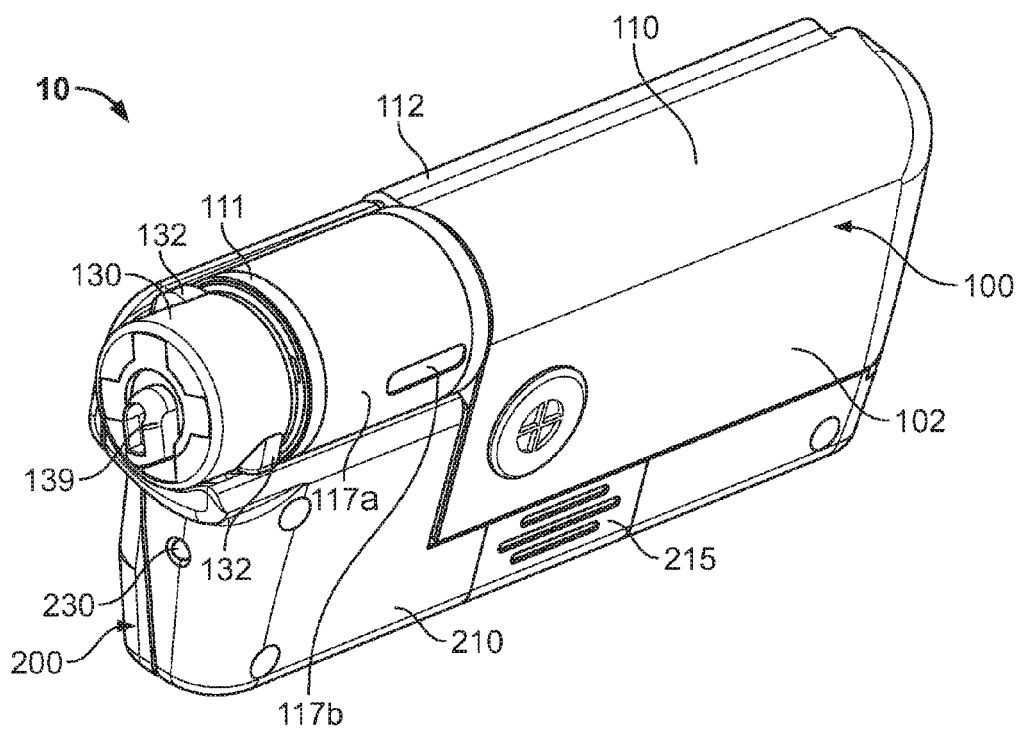
FIG. 3 is another perspective view of the infusion pump system of FIG. 2.

Referring to FIGS. 1-3, an infusion pump system 10 can include a pump device 100 and a controller device 200 that communicates with the pump device 100. The pump device 100 includes a housing structure 110 that defines a cavity 116 in which a fluid cartridge 120 can be received. The pump device 100 also includes a cap device 130 to retain the fluid cartridge 120 in the cavity 116 of the housing structure 110. The pump device 100 includes a drive system (described in more detail below) that advances a plunger 125 in the fluid cartridge 120 so as to dispense fluid therefrom. The controller device 200 communicates with the pump device 100 to control the operation of the drive system. When the controller device 200, the pump device 100 (including the cap device 130), and the fluid cartridge 120 are assembled together, the user can (in some embodiments) conveniently wear the infusion pump system 10 on the user's skin under clothing or in the user's pocket while receiving the fluid dispensed from the pump device 100.

The controller device 200 may be configured as a reusable component that provides electronics and a user interface to control the operation of the pump device 100. In such circumstances, the pump device 100 can be a disposable component that is disposed of after a single use. For example, the pump device 100 can be a "one time use" component that is thrown away after the fluid cartridge 120 therein is exhausted. Thereafter, the user can removably attach a new pump device 100 to the reusable controller device 200 for the dispensation of fluid from a new fluid cartridge 120. Accordingly, the user is permitted to reuse the controller device 200 (which may include complex or valuable electronics) while disposing of the relatively low-cost pump device 100 after each use. Such a pump system 10 can provide enhanced user safety as a new pump device 100 (and drive system therein) is employed with each new fluid cartridge 120.

Briefly, in use, the pump device 100 is configured to removably attach to the controller device 200 in a manner that provides a secure fitting, an overall compact size, and a reliable electrical connection that is resistant to water migration. For example, as described in more detail below in connection with FIGS. 1-5, the controller device 200 includes a housing 210 having a number of features that mate with complementary features of the pump housing 110. In such circumstances, the controller device 200 can removably attach with the pump device 100 in a generally side-by-side configuration while not fully surrounding the pump housing 110. Accordingly, the pump device 100 and the controller device 200 can be separate components that fit together, but the overall size of the combined assembly is reduced because there is no requirement for one component (e.g., the controller device) to completely surround or envelop the second component (e.g., the pump device). The compact size permits the infusion pump system 10 to be discrete and portable (as described below in connection with FIGS. 6-8). Moreover, at least one of the pump device 100 or the controller device 200 may include a release member that facilitates an easy-to-use detachment and replacement process. For example, as described in more detail below in connection with FIGS. 11-16, an exhausted pump device 100 may be a "one time use" component that is discarded after being used, and a new pump device 100' (having a new medicine cartridge 120') can thereafter be attached to the controller device 200.

Moreover, the pump device 100 and the controller device 200 can be mounted to one another so that the assembled system 10 is resistant to migration of external contaminants (e.g., water from precipitation or splashing, sweat, and the like) both into the pump housing structure 110 and the controller housing structure 210. In particular, the infusion pump system 10 may include one or more seals that are arranged to hinder migration of external contaminants into the cavity of the pump device 100 (e.g., to protect the insulin container 120 and the drive system during operation). Also, the infusion pump system may include one or more gaskets arranged proximate to the electrical connection location (between the pump device 100 and the controller device 200) to protect the electrical connection from migration of external contaminants. Thus, in some embodiments, the infusion pump system 10 can be assembled into a water resistant configuration that protects sensitive components from water migration (e.g., if the user encounters water while wearing the pump system 10).

In addition or in the alternative, the controller device 200 can be equipped with an illumination instrument 230 that provides the user with an opportunity to illuminate and inspect a targeted location. For example, as described in more detail below in connection with FIGS. 9-10, the light emitting device 230 can be directed at the infusion site on the user's skin to verify that the infusion set is properly embedded, or the light emitting device 230 can be directed at the pump device 100 to illuminate the cavity 116 or other areas.

Furthermore, in use, the controller device 200 can include a sensor configuration that detects occlusions in the fluid flow path extending to the user. For example, the controller device 200 may include an optical sensor system 250 that detects the amount of light reflected from a portion of the cap device 130. As described in more detail below in connection with FIGS. 26-38, the amount of light reflected from the cap device 130 may change if an occlusion occurs to cause an increase in the fluid pressure. For instance, some embodiments of the optical sensor system 250 may operate using the principle of total internal reflection. The optical sensor system 250 may include a number of components that are housed in the controller device 200. In one example, the light emitter and light sensor may be arranged on a sensor circuit in the controller device 200, thereby permitting these components to be reused along with the controller device (while the relatively low cost components in the pump device 100 are discarded after the "one time use" of the pump device 100).

Referring again to FIGS. 1-3, in this embodiment, the pump system 10 is a medical infusion pump system that is configured to controllably dispense a medicine from the cartridge 120. As such, the fluid cartridge 120 may contain a medicine 126 (FIG. 1) to be infused into the tissue or vasculature of a targeted individual, such as a human or animal patient. For example, the pump device 100 can be adapted to receive a medicine cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge may comprise a reservoir that is integral with the pump housing structure 110 (e.g., the fluid cartridge can be defined by one or more walls of the pump housing structure 110 that surround a plunger to define a reservoir in which the medicine is injected or otherwise received).

In some embodiments, the pump device 100 may include one or more structures that interfere with the removal of the medicine cartridge 120 after the medicine cartridge 120 is inserted into the cavity 116. For example, as shown in FIG. 1, the pump housing structure 110 may include one or more retainer wings 119 that at least partially extend into the cavity 116 to engage a portion of the medicine cartridge 120 when the medicine cartridge 120 is installed therein. In this embodiment, the pump housing structure 110 includes a pair of opposing retainer wings 119 (only one is shown in the view in FIG. 1) that flex toward the inner surface of the cavity 116 during insertion of the medicine cartridge 120. After the medicine cartridge is inserted to a particular depth, the retainer wings 119 are biased to flex outward (toward the center of the cavity 116) so that the retainer wings 119 engage a neck portion 129 of the medicine cartridge 120. This engagement with the retainer wings 119 and the neck portion 129 hinder any attempts to remove the medicine cartridge 120 away from the pump device 100.

Such a configuration may facilitate the "one-time-use" feature of the pump device 100. Because the retainer wings 119 interfere with attempts to remove the medicine cartridge 120 from the pump device 100, the pump device 100 will be discarded along with the medicine cartridge 120 after the medicine cartridge 120 is emptied, expired, or otherwise exhausted. The retainer wings 119 may serve to hinder attempts to remove the exhausted medicine cartridge 120 and to insert a new medicine cartridge 120 into the previously used pump device 100. Accordingly, the pump device 100 may operate in a tamper-resistant and safe manner because the pump device 100 can be designed with predetermined life expectancy (e.g., the "one-time-use" feature in which the pump device is discarded after the medicine cartridge 120 is emptied, expired, or otherwise exhausted).

Still referring to FIGS. 1-3, the cap device 130 can be joined with the pump device 100 after the medicine cartridge is inserted in the cavity 116. In this embodiment, the cap device 130 is multifunctional in that it performs a number of functions for the pump device operation. For example, attachment of the cap device 130 may cause one or more of the following preparatory functions: forcing the plunger 125 (FIG. 1) of the fluid cartridge 120 to engage with the piston rod (not shown in FIGS. 1-3, refer for example to FIG. 19), piercing a septum 121 of the fluid cartridge 120 to provide a flow path for the fluid (refer for example to FIG. 27), and priming the fluid cartridge 120 with a "break away" force to initiate movement of the plunger 125 in the fluid cartridge 120. In addition or in the alternative, attachment of the cap device 130 may also cause one or more of the following safety related functions: aligning an occlusion sensor 250 with the a portion of the fluid flow path (described in connection with FIGS. 26-38), sealing the pump housing 110 (e.g., using a polymeric o-ring seal 131 or the like) to resist migration of external contaminants into the cavity 116, and ceasing or preventing the dispensation of fluid if the cap device 130 is improperly engaged with the pump housing 110. In other embodiments, the cap device 130 may supplement or replace the previously described retainer wings 119 by locking into position after joining with the pump housing 110, thereby hindering removal of the fluid cartridge 120 in the pump housing 110.

The cap device 130 can include one or more alignment tabs 132 that operate to ensure that the cap device 130 is joined with the pump housing 110 in a selected orientation. For example, as shown in FIGS. 2-3, the cap device 130 may include an output port 139 that connects with tubing (e.g., FIG. 6) for dispensation of the medicine to the user. The output port 139 may have an angled orientation such that a portion of the tubing extends transversely to the central axis of the cartridge 120 and cap device 130. The alignment tabs 132 arranged on the body of the cap device 130 can align with adjacent surfaces of the controller housing 210 to provide the selected orientation of the output port during operation. If, for example, the cap device 130 were joined with the pump housing 100 in an orientation that is 180-degrees off from the selected orientation, the alignment tabs 132 would receive interference from the barrel channel 211 of the controller housing 210. As such, the user would be unable to attach the pump device 100 to the controller 200, thereby indicating to the user that the cap device 130 must be reoriented to the selected position.

Still referring to FIGS. 1-3, the controller device 200 may be removably attached to the pump device 100 so that the two components are mechanically mounted to one another in a fixed relationship. Such a mechanical mounting can form an electrical connection between the removable controller device 200 and the pump device 100. For example, the controller device 200 may be in electrical communication with a portion of a drive system (not shown in FIGS. 1-3) of the pump device 100. As described in more detail below, the pump device 100 includes a drive system that causes controlled dispensation of the medicine or other fluid from the cartridge 120. In some embodiments, the drive system incrementally advances a piston rod (not shown in FIGS. 1-3) longitudinally into the cartridge 120 so that the fluid is forced out of an output end 122. A septum 121 (FIG. 1) at the output end 122 of the fluid cartridge 120 can be pierced to permit fluid outflow when the cap device 130 is connected to the pump housing structure 110 (described in more detail below). Thus, when the pump device 100 and the controller device 200 are attached and thereby electrically connected, the controller device 200 communicates electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the medicine cartridge 120.

In some embodiments, the controller device is configured to removably attach to the pump device 100 in a side-by-side arrangement. As such, the controller device 200 can be electrically connected with the pump device 100 while the controller device 200 remains outside of the pump housing 110 (and, likewise, the pump device 100 remains outside of the controller housing 210). Accordingly, the pump device 100 and the controller device 200 can be separate components that fit together, but the overall size of the combined assembly is reduced because there is no requirement for one component (e.g., the controller device) to completely surround or envelop the second component (e.g., the pump device). The compact size permits the infusion pump system 10 to be discrete and portable when the pump device 100 is attached with the controller device 200 (as shown in FIGS. 2-3). In this embodiment, the controller device 200 includes a controller housing structure 210 having a number of features (e.g., a barrel channel 211, a rail 212, a depression 213, and a guide channel 214a-b that is segmented by a release latch 215) that are configured to mate with complementary features (e.g., a barrel 111, a slider channel 112, an mating extension 113, and a segmented guide rail 114a-b) of the pump housing structure 110 so as to form a releasable mechanical connection (as shown, for example, in FIGS. 1 and 4-5). Such mating features of the pump housing structure 110 and the controller housing structure 210 can provide a secure connection in the previously described side-by-side arrangement. It should be understood that, in other embodiments, other features or connector devices can be used to facilitate the side-by-side mounting arrangement. These other features or connector devices may include, for example, magnetic attachment devices, mating tongues and grooves, or the like.

As shown in FIG. 1, the pump device 100 may include an electrical connector 118 (e.g., having conductive pads, pins, and the like) that are exposed to the controller device 200 and that mate with a complementary electrical connector (refer to connector 218 in FIG. 4) on the adjacent face of the controller device 200. The electrical connectors 118 and 218 provide the electrical communication between the control circuitry (refer, for example, to FIG. 17) housed in the controller device 200 and at least a portion of the drive system or other components of the pump device 100. For example, in some embodiments, the electrical connectors 118 and 218 permit the transmission of electrical control signals to the pump device 100 and the reception of feedback signals (e.g., sensor signals) from particular components within the pump device 100. Furthermore, as described in more detail below, the infusion pump system 10 may include a gasket 140 that provides a seal that is resistant to migration of external contaminants when the pump device 100 is attached to the controller device 200. Thus, in some embodiments, the infusion pump system 10 can be assembled into a water resistant configuration that protects the electrical interconnection from water migration (e.g., if the user encounters water while carrying the pump system 10).

Still referring to FIGS. 1-3, the controller device 200 includes a user interface 220 that permits a user to monitor the operation of the pump device 100. In some embodiments, the user interface 220 includes a display 222 and one or more user-selectable buttons (e.g., four buttons 224a, 224b, 224c, and 224d in this embodiment). The display 222 may include an active area in which numerals, text, symbols, images, or a combination thereof can be displayed (refer, for example, to FIG. 2). For example, the display 222 may be used to communicate a number of settings or menu options for the infusion pump system 10. In this embodiment, the user may press one or more of the buttons 224a, 224b, 224c, and 224d to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons 224a, 224b, 224c, and 224d of the user interface 220. For example, in embodiments of the infusion pump system 10 configured to dispense insulin, the user may press one or more of the buttons 224a, 224b, 224c, and 224d to change the dispensation rate of insulin or to request that a bolus of insulin be dispensed immediately or at a scheduled, later time. Also, as described below in connection with FIGS. 9-10, the user can activate the illumination instrument 230 on the controller device 200 by pressing one or more buttons 224a, 224b, 224c, and 224d of the user interface 220.

The display 222 of the user interface 220 may be configured to display quick reference information when no buttons 224a, 224b, 224c, and 224d have been pressed. For example, as shown in FIG. 2, the active area of the display 222 can display the time and the date for a period of time after no button 224a, 224b, 224c, and 224d has been actuated (e.g., five seconds, 10 seconds, 30 seconds, 1 minute, 5 minutes, or the like). Thereafter, the display 222 may enter sleep mode in which the active area is blank, thereby conserving battery power. In addition or in the alternative, the active area can display particular device settings, such as the current dispensation rate or the total medicine dispensed, for a period of time after no button 224a, 224b, 224c, or 224d has been actuated (e.g., five seconds, 10 seconds, 30 seconds, 1 minute, 5 minutes, or the like). Again, thereafter the display 222 may enter sleep mode to conserve battery power. In certain embodiments, the display 222 can dim after a first period of time in which no button 224a, 224b, 224c, or 224d has been actuated (e.g., after 15 seconds or the like), and then the display 22 can enter sleep mode and become blank after a second period of time in which no button 224a, 224b, 224c, or 224d has been actuated (e.g., after 30 seconds or the like). Thus, the dimming of the display device 222 can alert a user viewing the display device 222 when the active area 223 of the display device will soon become blank.

Accordingly, when the controller device 200 is connected to the pump device 100, the user is provided with the opportunity to readily monitor infusion pump operation by simply viewing the user interface 220 of the controller device 200 connected to the pump device 100. Such monitoring capabilities may provide comfort to a user who may have urgent questions about the current operation of the pump device 100 (e.g., the user may be unable to receive immediate answers if wearing an infusion pump device having no user interface attached thereto).

Also, in these embodiments, there may be no need for the user to carry and operate a separate module to monitor the operation of the infusion pump device 100, thereby simplifying the monitoring process and reducing the number of devices that must be carried by the user. If a need arises in which the user desires to monitor the operation of the pump device 100 or to adjust settings of the pump system 10 (e.g., to request a bolus amount of medicine), the user can readily operate the user interface 220 of the controller device 200, which is removably attached to the pump device 100, without the requirement of locating and operating a separate monitoring module.

In other embodiments, the user interface 200 is not limited to the display and buttons depicted in FIGS. 1-3. For example, in some embodiments, the user interface 220 may include only one button or may include a greater numbers of buttons, such as two buttons three buttons, four buttons, five buttons, or more. In another example, the user interface 220 of the controller device 200 may include a touch screen so that a user may select buttons defined by the active area of the touch screen display. Alternatively, the user interface 220 may comprise audio inputs or outputs so that a user can monitor the operation of the pump device 100.

Figure 4:
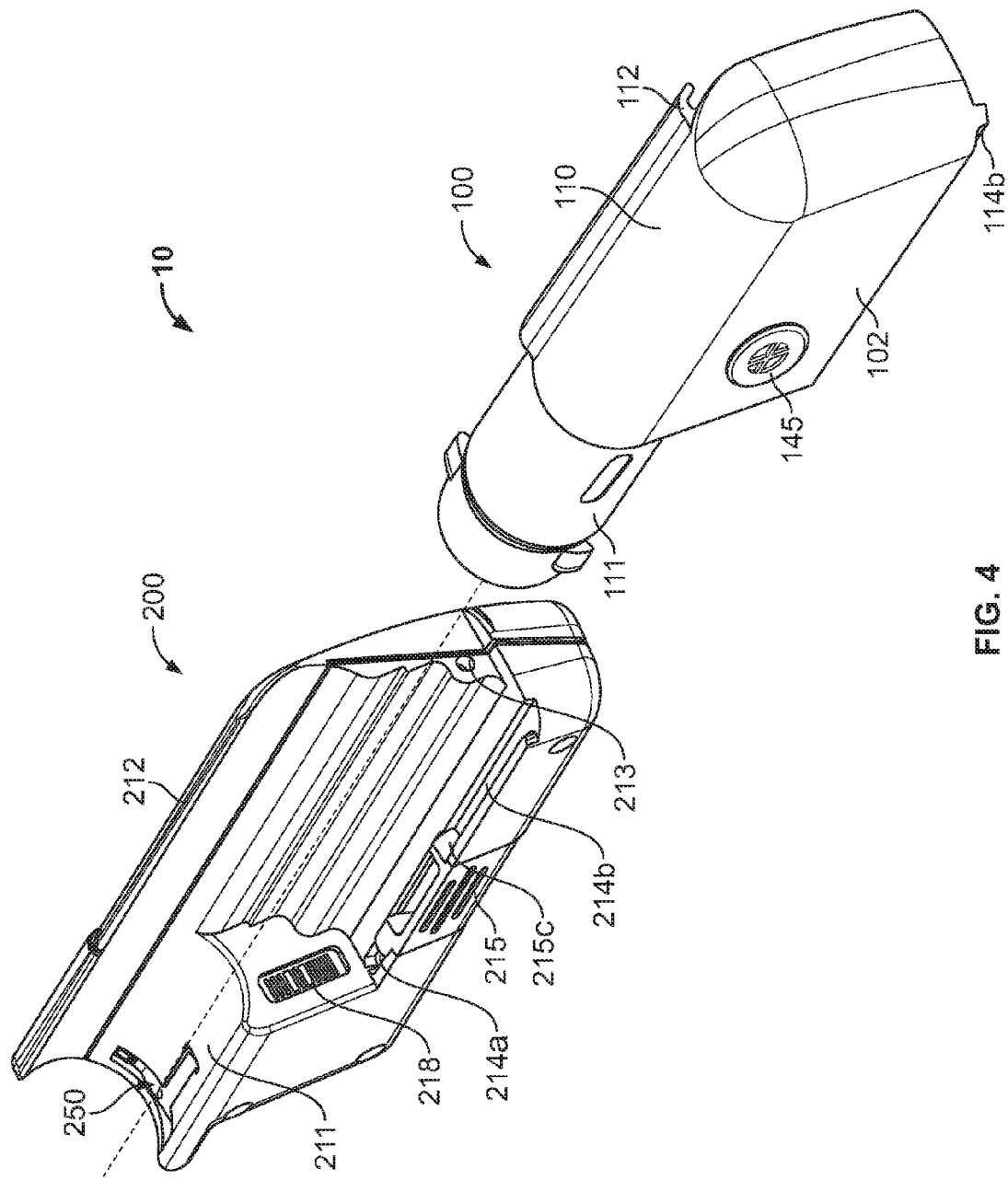
FIG. 4 is a perspective view of the infusion pump system of FIG. 1 in a detached state.
Figure 5:
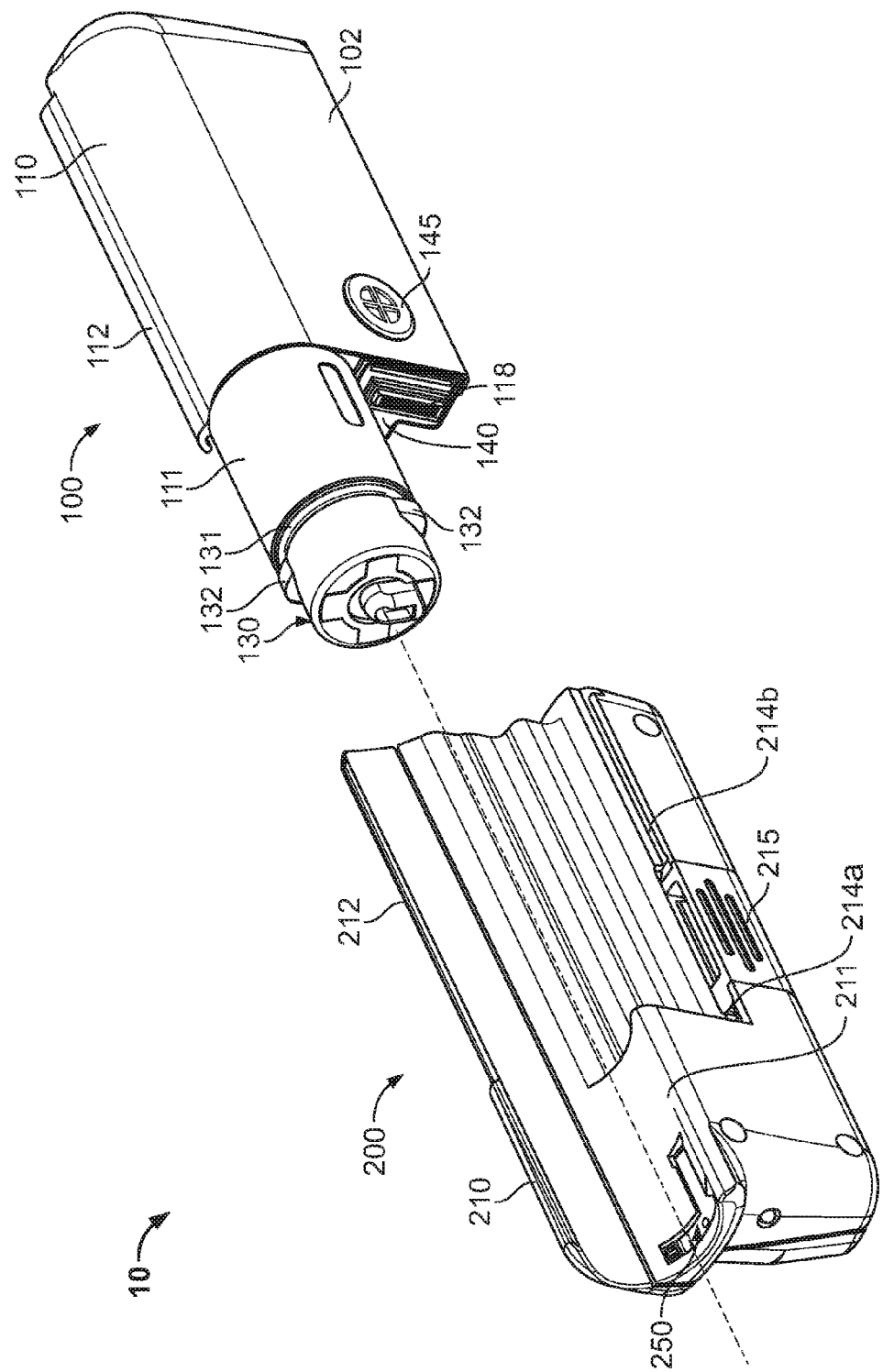
FIG. 5 is another perspective view of the infusion pump system on FIG. 4.

Referring now to FIGS. 4-5, when the infusion pump system 10 operates, the controller device 200 is removably attached to the pump device 100 in a side-by-side arrangement. For example, the pump device 100 may be moved in a longitudinal direction (e.g., refer to direction 219 in FIG. 15) toward the controller device 200 until the complementary features connect and secure the separate components in the side-by-side arrangement. In these circumstances, the pump device 100 and the controller device 200 can be separate components that fit together, but the overall size of the combined assembly is reduced because there is no requirement for one component (e.g., the controller device or pump device) to surround or envelop the second component (e.g., the pump device or controller device). Moreover, in some embodiments, the pump device 100 and controller device 200 can be readily attached together with a "one-movement" process that is convenient to the user (described in more detail below).

In this embodiment, the controller device 200 includes a controller housing structure 210 having a number of features that are configured to mate with complementary features of the pump housing structure 110 so as to form a releasable mechanical connection. For example, the pump housing structure 110 may include a barrel 111 that mates with a complementary barrel channel 211 of the controller housing 210. Also, the pump housing 110 includes slider channel 112 that slidably engages a complementary rail 212 defined by the controller housing 210. The slider channel 112 can guide the relative motion between the pump device 100 and the controller device 200 in the longitudinal direction during the attachment process. Similarly, the pump housing 110 may include a segmented rail 114a-b (FIG. 1) that mates with a guide channel 214a-b to direct the relative longitudinal motion between the pump device 100 and the controller device 200. As described in more detail below, the segmented rails 114a-b may interact with the release member 215 so as to releasably secure the pump device 100 into assembly with the controller device 200. In addition, the pump housing 110 may include an extension 113 (FIG. 1) that mates with a depression 213 (FIG. 5) in the controller housing 210 when the pump device 100 is fully attached to the controller device 200.

Still referring to FIGS. 4-5, when the pump device 100 is advanced in the longitudinal direction toward the controller device 200 as guided by the slider channel 112 and the segmented rails 114a-b, the electrical connector 118 (FIG. 5) of the pump device 100 is directed toward engagement with the mating connector 218 (FIG. 4) of the controller device 200. As the connectors 118 and 218 join together to form the electrical connection, the release member 215 is shifted to a position between the segmented rails 114a-b so as to prevent withdrawal of the connection. Also, when the connectors 118 and 218 are mated, the extension 113 and barrel 111 are mated with the corresponding depression 213 and barrel channel 211 so as to resist relative rotational movement between the pump device 100 and the controller device 200. In this embodiment, the physical attachment of the electrical connectors 118 and 218 may also serve to resist relative rotational movement between the pump device 100 and the controller device 200. Furthermore, when the connectors 118 and 218 are mated, the slide channel 112 is mated with the corresponding rail 112 and barrel channel 211 so as to resist relative side-to-side movement between the pump device 100 and the controller device 200.

Accordingly, the pump device 100 is configured to removably attach to the controller device 200 in a manner that provides a secure fitting, an overall compact size, and a reliable electrical connection. When the pump device 100 and the controller device 200 are arranged in this side-by-side configuration, the controller device 200 can be electrically connected with the pump device 100 while the controller device 200 remains outside of the pump housing 110 (and, likewise, the pump device 100 remains outside of the controller housing 210). As such, the overall size of the assembled system 10 can be minimized, thereby providing an infusion pump system 10 having a discrete size and enhanced portability.

Additionally, in some embodiments, the attachment of the pump device 100 to the controller device 200 can be accomplished by a user with a convenient "one-movement" process. For example, as previously described, the user can readily slide the pump device 100 and the controller device 200 toward one another in a single movement (e.g., in the longitudinal direction) that causes both a physical connection and an electrical connection. As described in more detail below in connection with FIGS. 11-16, the release member 215 may be arranged so as to automatically adjust to a locked position when the pump device 100 is advanced into engagement with the controller device 200. Thus, the infusion pump system 10 permits users to readily join the pump device 100 and the controller device 200 without compound or otherwise difficult hand movements—a feature that can be beneficial to child users or to elderly users.

It should be understood that, in other embodiments, other features or connector devices can be used to facilitate the side-by-side mounting arrangement. These other features or connector devices may include, for example, magnetic attachment device, mating tongues and grooves, mounting protrusions that friction fit into mating cavities, or the like.

Still referring to FIGS. 4-5, the pump device 100 and the controller device 200 can be attached in a manner that is resistant to migration of external contaminants (e.g., water, dirt, and the like) both into the pump housing structure 110 and the controller housing structure 210. For example, when the pump device 100 is advanced in the longitudinal direction toward the controller device 200 (as guided by the slider channel 112 and the segmented rails 114*a-b*), the electrical connector 118 (FIG. 5) of the pump device 100 is directed toward engagement with the mating connector 218 (FIG. 4) of the controller device 200. When the connectors 118 and 218 join together to form the electrical connection, the gasket 140 is compressed between the adjacent surfaces of the pump housing 110 and the controller housing 210. The gasket 140 thereby forms a water-resistant seal between the ambient environment and the mated connectors 118 and 218.

The gasket 140 may comprise a polymer foam material that is adhered to a surface of either the pump housing 110 or the controller housing 210 (e.g., adhered to the pump housing 110 in this embodiment). The gasket 140 may be die cut to a selected shape so as to include an aperture for the electrical connection. Thus, in this embodiment, the gasket 140 surrounds the electrical connection when the pump device 100 is secured to the controller device 200. The configuration provides protection from water migration to one or both of the electrical connectors 118 and 218. Accordingly, in particular circumstances, the infusion pump system 10 can be assembled into a "water tight" configuration that protects sensitive internal components from water migration in the event that the user encounters water while wearing the pump system 10. In one example, the gasket 140 may resist migration of water to the electrical connectors 118 and 218 even when the system 10 is submerged underwater (e.g., in a pool, in a bath, or the like) for an extended period of time, such as at least 10 minutes, at least 30 minutes, at least one hour, at least two hours, and preferably at least four hours.

As shown in FIG. 5, the gasket 140 is arranged to extend generally perpendicular to the assembly motion when the pump device 100 is being attached to the controller device. For example, the pump device 100 can be attached to the controller device 200 by moving the pump device 100 in the longitudinal direction (e.g., refer to direction 219 in FIG. 15). The gasket 140 includes a major interface surface extends in a generally lateral direction that is perpendicular to the longitudinal assembly motion. Because the gasket 140 extends in a direction (e.g., the lateral direction in this embodiments) that is generally perpendicular to the attachment direction (the longitudinal direction in this embodiment), the gasket 140 can be sufficiently compressed to form a seal when the user performs the "one-movement" process to attach the pump device 100 and the controller device 200.

In addition, other paths for migration of external contaminants into the assembled pump system 10 may be sealed. For example, the infusion pump system 10 may include one or more seals that are arranged to hinder migration of external contaminants between the cap device 130 and the pump housing 110 into the cavity 116 of the pump device 100. In this embodiment, the seal 131 arranged between the cap device 130 and the barrel 111 can provide an effective water-resistant seal against water migration into the cavity. As such, the medicine cartridge 120 and pump drive system (not shown in FIGS. 4-5) can be protected during operation.

Still referring to FIGS. 4-5, some embodiments of the infusion pump system 10 may employ a power source arranged in pump device 100 or the controller device 200 that draws upon surrounding air for optimum operation. Because the controller device 200 and the pump device 100 may be sealed to resist water migration during normal usage, a water-resistant vent instrument 145 may be used to provide the air to the power source without permitting migration of water therethrough. For example, in this embodiment, the pump device 100 may house a power source 345 in the form of a zinc-air cell battery (refer to FIG. 18), which draws upon the surrounding air during operation. When the pump device 100 is in use, the pump housing 110 is preferably sealed to protect the internal drive system and medicine cartridge from water migration. As such, the pump housing 110 may include a water-resistant vent instrument 145 disposed proximate to the zinc-air cell battery 345 so that some air may pass through the vent 145 and toward the battery. The water-resistant vent instrument 145 may include one or more layers of a material that is permeable to air and resistant to passage of liquids such as water. For example, the water-resistant vent instrument 145 may include one or more layers of a GORE-TEX material to resist the migration of water into the pump device while permitting the passage of air toward the battery.

Accordingly, the pump device 100 and the controller device 200 can be mounted to one another so that the assembled system 10 is resistant to water migration both into the pump housing structure 110 and the controller housing structure 210. Such a configuration may also provide water-resistant protection for the electrical connection between the pump device 100 and the controller 200. Thus, the sensitive internal components in the controller device 200 and the pump device 100 can be reliably protected from water migration if the user encounters water (e.g., rain, incidental splashing, and the like) while using the pump system 10.

Figure 6:
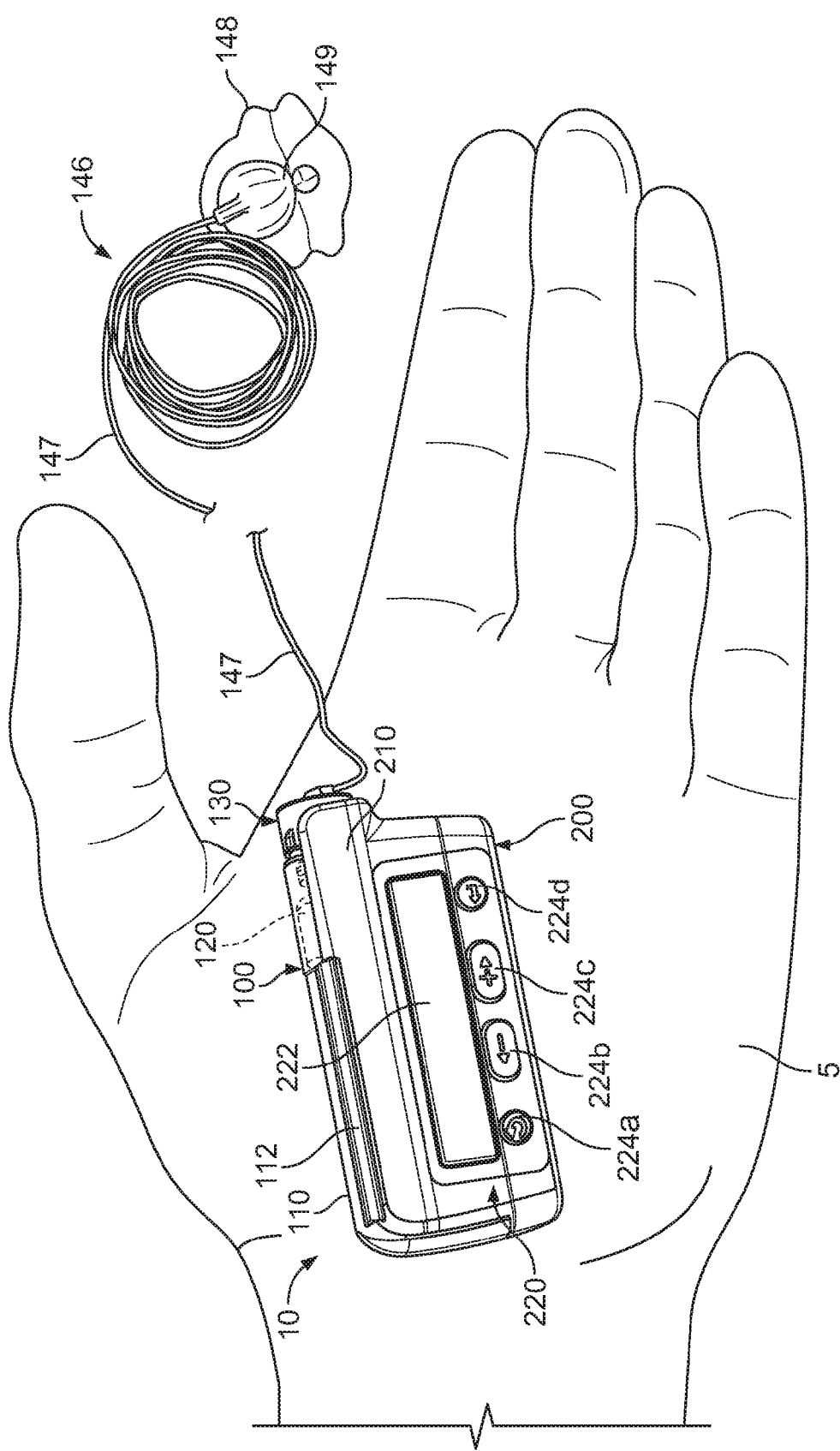
FIG. 6 is a perspective view of an infusion pump system, in accordance with some embodiments.
Figure 7:
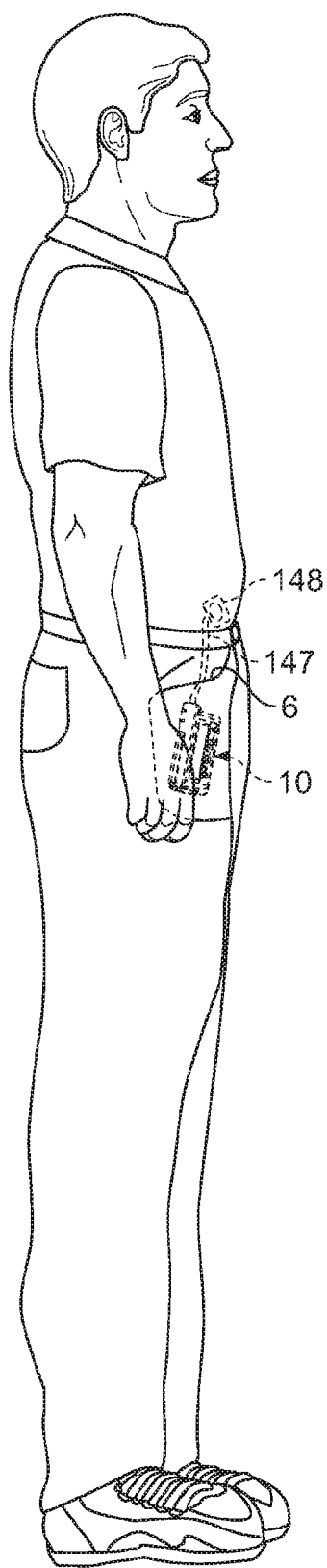
FIG. 7 is a perspective view of the infusion pump system of FIG. 6 worn on clothing of a user.
Figure 8:
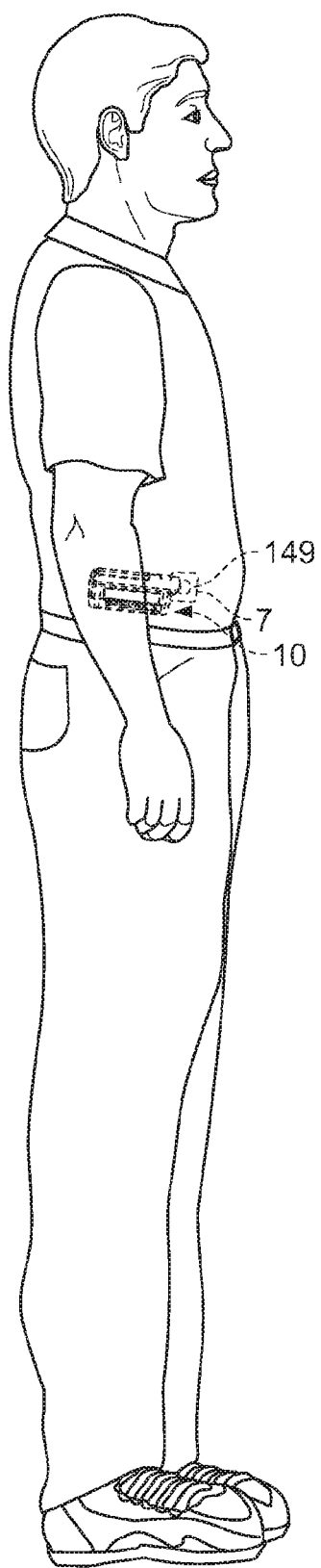
FIG. 8 is a perspective view of an infusion pump system worn on skin of a user, in accordance with particular embodiments.

Referring to FIGS. 6-8, the infusion pump system 10 may be configured to be portable and can be wearable and concealable. For example, a user can conveniently wear the infusion pump system 10 on the user's skin (e.g., skin adhesive) underneath the user's clothing or carry the pump device 100 in the user's pocket (or other portable location) while receiving the medicine dispensed from the pump device 100. As described below in connection with FIGS. 18-25, the drive system of the pump device 100 may be arranged in a compact manner so that the pump device 100 has a reduced length. For example, in the circumstances in which the medicine cartridge 120 has a length of about 6 cm to about 7 cm (about 6.4 cm in one embodiment), the overall length of the pump housing structure 110 (which contains medicine cartridge and the drive system) can be about 7 cm to about 10 cm and about 7 cm to about 9 cm (about 8.3 cm or less in one embodiment). In addition, the pump housing structure 110 may have an overall height of about 2 cm to about 4 cm (about 3.1 cm or less in one embodiment) and an overall thickness of about 8 mm to about 20 mm (about 17.5 mm or less in one embodiment). In such circumstances, the controller device 200 can be figured to mate with the pump housing 110 so that, when removably attached to one another, the components define a portable infusion pump system that stores a relatively large quantity of medicine compared to the overall size of the unit. For example, in this embodiment, the infusion pump system 10 (including the removable controller device 200 attached to the pump device 100 having the cap 130) may have an overall length of about 7 cm to about 10 cm (about 9.3 cm or less in one embodiment), an overall height of about 2 cm to about 5 cm (about 4.2 cm or less in one embodiment), and an overall thickness of about 8 mm to about 20 mm (about 17.5 mm or less in one embodiment).

The pump system 10 is shown in FIG. 6 as being held in a user's hand 5 so as to illustrate an exemplary size of the system 10 in accordance with some embodiments. This embodiment of the infusion pump system 10 is compact so that the user can wear the portable infusion pump system 10 (e.g., in the user's pocket, connected to a belt clip, adhered to the user's skin, or the like) without the need for carrying and operating a separate module. In such embodiments, the cap device 130 of the pump device 100 may be configured to mate with an infusion set 146. In general, the infusion set 146 is tubing system that connects the infusion pump system 10 to the tissue or vasculature of the user (e.g., to deliver medicine into the tissue or vasculature under the user's skin) The infusion set 146 may include a flexible tube 147 that extends from the pump device 100 to a subcutaneous cannula 149 retained by a skin adhesive patch 148 that secures the subcutaneous cannula 149 to the infusion site. The skin adhesive patch 148 can retain the infusion cannula 149 in fluid communication with the tissue or vasculature of the patient so that the medicine dispensed through the tube 147 passes through the cannula 149 and into the user's body. The cap device 130 may provide fluid communication between the output end 122 (FIG. 1) of the medicine cartridge 120 and the tube 147 of the infusion set 146. For example, the tube 147 may be directly connected to the output port 139 (FIG. 1) of the cap device 130. In another example, the infusion set 146 may include a connector (e.g., a Leur connector or the like) attached to the tube 147, and the connector can then mate with the cap device 130 to provide the fluid communication to the tube 147. In these examples, the user can carry the portable infusion pump system 10 (e.g., in the user's pocket, connected to a belt clip, adhered to the user's skin, or the like) while the tube 147 extends to the location in which the skin is penetrated for infusion. If the user desires to monitor the operation of the pump device 100 or to adjust the settings of the infusion pump system 10, the user can readily access the user interface 220 of the controller device 200 without the need for carrying and operating a separate module (refer for example to FIG. 6).

Referring to FIG. 7, in some embodiments, the infusion pump system 10 is pocket-sized so that the pump device 100 and controller device 200 can be worn in the user's pocket 6 or in another portion of the user's clothing. For example, the pump device 100 and the controller device 200 can be attached together and form the system that comfortably fits into a user's pocket 6. The user can carry the portable infusion pump system 10 and use the tube 147 of the infusion set 146 extends to direct the dispensed medicine to the desired infusion site. In some circumstances, the user may desire to wear the pump system 10 in a more discrete manner. Accordingly, the user may pass the tube 147 from the pocket 6, under the user's clothing, and to the infusion site where the adhesive patch 148 is positioned. As such, the pump system 10 can be used to delivery medicine to the tissues or vasculature of the user in a portable, concealable, and discrete manner.

Referring to FIG. 8, in other embodiments, the infusion pump system 10 may be configured to adhere to the user's skin 7 directly at the location in which the skin is penetrated for medicine infusion. For example, a rear surface 102 (FIG. 3) of the pump device 100 may include a skin adhesive patch so that the pump device 100 is physically adhered to the skin of the user at a particular location. In these embodiments, the cap device 130 may have a configuration in which medicine passes directly from the cap device 130 into an infusion cannula 149 that is penetrated into the user's skin. In one example, the fluid output port 139 through the cap device 130 can include a curve or a 90° corner so that the medicine flow path extends longitudinally out of the medicine cartridge and thereafter laterally toward the patient's skin 7. Again, if the user desires to monitor the operation of the pump device 100 or to adjust the settings of the infusion pump system 10, the user can readily access the user interface 220 of the controller device 200 without the need for carrying and operating a second, separate device. For example, the user may look toward the pump device 100 to view the user interface 220 of the controller device 200 that is removably attached thereto. In another example, the user can temporarily detach the controller device 200 (while the pump device 100 remains adhered to the skin 7) so as to view and interact with the user interface 220.

Figure 9:
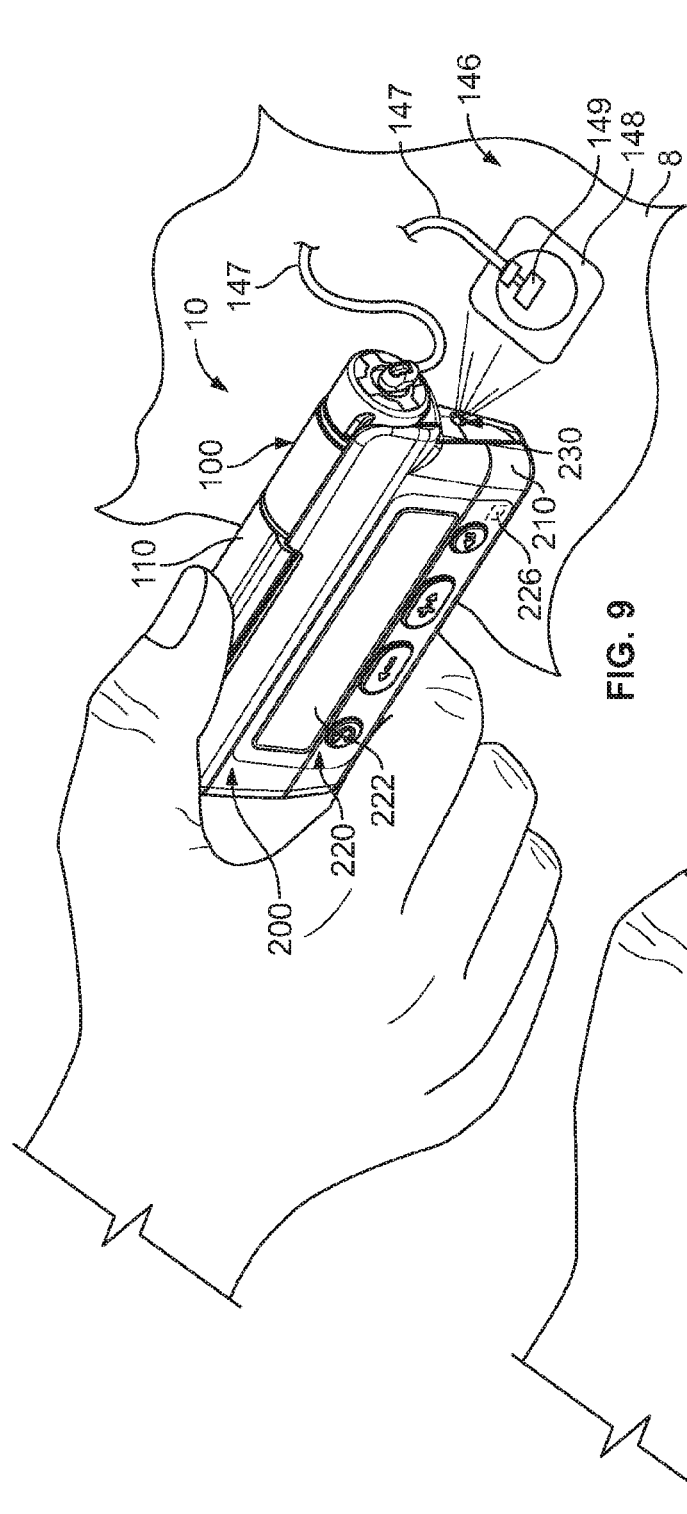
FIG. 9 is a perspective view on an infusion pump system having an illumination instrument, in accordance with some embodiments.
Figure 10:
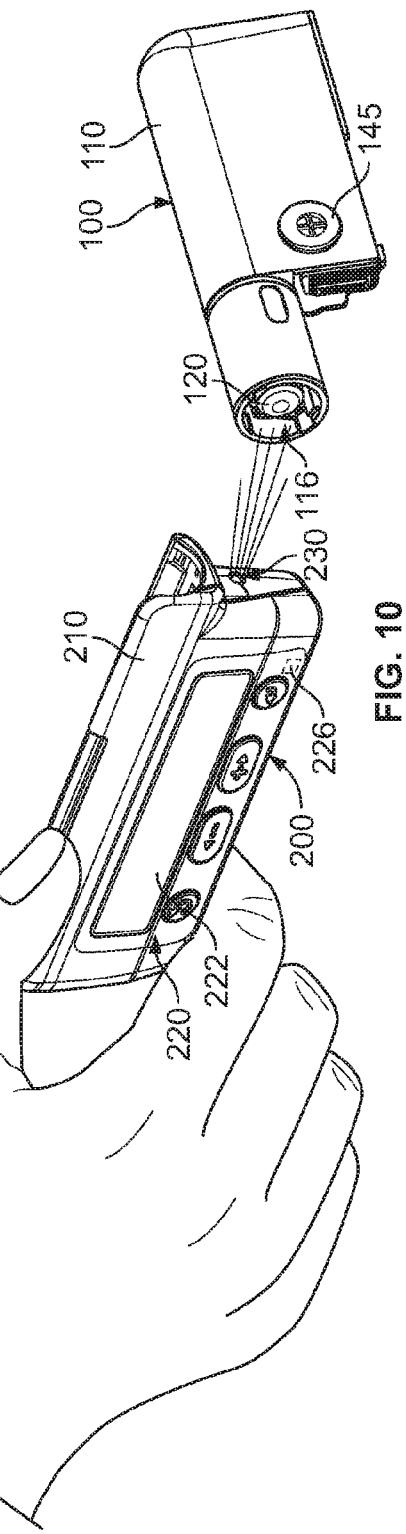
FIG. 10 is a perspective view of an infusion pump system having an illumination instrument, in accordance with particular embodiments.

Referring now to FIGS. 9-10, the infusion pump system 10 can include an illumination instrument 230 that provides the user with an opportunity to illuminate and inspect a targeted location. The illumination instrument 230 can be useful in situations where the ambient lighting is insufficient for the user's inspection needs (e.g., during the night, during presentation or movie in which the lighting is low, or the like). The illumination instrument 230 can be arranged on the pump device 100, the controller device 200, or both. In this embodiment, the illumination instrument is arranged on the controller device 200. In such circumstances, the illumination instrument 230 can be directed at the infusion site on the user's skin 8 to verify that the infusion set cannula 149 is properly embedded (refer, for example, to FIG. 9). In another example, the illumination instrument 230 can be directed at the pump device 100 to illuminate some portion of the pump device 100, such as the cavity 116 in which the medicine cartridge 120 is received (refer to FIG. 10).

During the operation of the infusion pump system 10, the user may be instructed to periodically assess the condition of the connection of the infusion set 146 into the user's body. This assessment can include visually inspecting the adhesive pad 148 that secures the set to the body and the cannula 149 that passes through the skin 8 to provide access for the medicine to enter the tissue or vasculature. In some cases, this inspection reveals that a new infusion set 146 is needed, and the user can thereafter change the infusion set 146 by attaching a new infusion set 146 to the user's skin 8 and the to the pump device 100. Changing the infusion set 146 can be a detailed process that requires the user to visualize the infusion site along the skin 8 as well as the tip of the infusion cannula 149 prior to insertion (e.g., to verify proper priming or filling of the infusion set tubing 147).

Also during operation of the infusion pump system 10, the user may encounter a need to visually inspect one or more or components of the pump device 100. For example, the user may visually inspect the medicine cartridge 120 in the cavity 116 of the pump housing 110 to verify the fluid level in the medicine cartridge 120. Although the controller device 200 can include sensors and software to track medicine usage and provide an estimate of the remaining fluid volume, visual confirmation of the fluid level can be comforting to many users. If the visual inspection of the cavity 116 reveals that the medicine cartridge 120 has a low fluid level or is broken, the user can employ a new pump device 100' and a new medicine cartridge 120' as described below in connection with FIGS. 11-16.

As shown in FIGS. 9-10, the infusion pump system 10 can be equipped with the illumination instrument 230 to conveniently aid in visual inspection processes. For example, visual inspection and possible change of the infusion set 146 may be required in less than optimal conditions, including low-light conditions. Likewise, visual inspection of the pump housing cavity 116 (and the medicine cartridge 120 therein) may be required in low-light conditions. The user interface 220 of the controller device 200 can include an illuminated display screen 222 to facilitate the user's view of the display screen 22, but the illumination instrument 230 provides a dedicated light source for illuminating targeted sites external to the controller device 200 (e.g., the skin 8, the infusion set 146, or the like).

The illumination instrument 230 can include one or more user triggered light sources that are positioned to direct illumination at targeted objects outside of the pump system 10 or at components of the pump device 100. In the embodiments depicted in FIGS. 9-10, the light source is arranged on the controller device 200. Such an arrangement provides close proximity to the control circuitry 240 housed in the controller device 200. In other embodiments, could be arranged on the pump device 100 or on both the controller device 200 and the pump device 100.

Still referring to FIGS. 9-10, the illumination instrument 230 may include a light source in the form of an LED device 232 (FIG. 17) that is electrically connected to the control circuitry 240 (FIG. 17) in the controller housing 210. The light transmitted from the LED device 232 may be directed through a light guide 234 (FIGS. 17 and 26) extending to the controller housing 210 so that the light exits the light guide 234 and illuminates the targeted object. In some circumstances, the light guide 234 may operate as a light transmissive cover that permits light to pass out of the controller device 200 while sealing out water or other contaminants. Such a construction, for example, may provide an illumination instrument 230 that emits an inspection light even when submerged underwater for a particular period of time. As shown in FIGS. 9-10, the light from the illumination instrument 230 can be emitted from a side of the controller device 200 that is different from the side on which the user interface 220 is exposed. In this example, the light from the illumination instrument 230 exits from the light guide 234 toward a targeted site while the display 222 and buttons 224a-d face a different direction. Thus, the illumination instrument 230 can direct an inspection light toward a targeted site while the user interface 220 remains in a viewable position for the user.

In this embodiment, the illumination instrument 230 emits a beam of light (e.g., a generally cylindrical or conical beam) that provides an intensity sufficient for visually inspecting external sites. For example, the light transmitted from the LED device 232 may be directed through a plastic light guide 234 to provide a beam of light having an illumination intensity that is sufficient to noticeably illuminate a specific area (e.g., a circular area having a diameter of about 10 inches) around a targeted site from more than six inches away, from more that twelve inches away, and preferably from more than eighteen inches away.

The user may, for example, actuate one or more buttons 224a-d of the user interface 220 to activate the illumination instrument 230. For example, the illumination instrument 230 may be configured to activate and transmit light when the user presses a single button (e.g., activate immediately when the single button is pressed or after the single button is pressed-and-held for a short period of time such as two seconds). The illumination device 230 may remain activated while the selected button was held down, and would thereafter shut off when the button is no longer pressed. This press-and-hold activation sequence can conserve battery power as the light is emitted only as long as the user holds the button. In another example, the illumination instrument 230 may be configured to activate and transmit light when the user presses a specified button sequence. The light would be emitted from the illumination instrument 230 while the user would have both hands available for the inspection process. To deactivate the illumination instrument 230 in this embodiment, the user may press another button sequence.

In other embodiments, the illumination instrument 230 can operate in conjunction with a timer that automatically deactivates the light source after a predetermined period of time. The duration of the timer could either be preset at the factory or adjustable by the user (e.g., by selecting the particular menu settings with the user interface 220). For example, the control circuitry 240 (FIG. 17) may operate to automatically shut off the illumination instrument 230 after a predetermined period of time, such as 5 seconds, 10 seconds, 20 seconds, 30 seconds, or the like. Such a timer feature can reduce the required user input effort and can conserve battery power.

In some circumstances, the illumination instrument 230 may serve as an indicator to the user that a particular condition exists. For example, the illumination instrument 230 may be automatically activated by the controller device 200 to serve as an alarm that an error has occurred (e.g., a controller error, a drive system error, a flow path error, or the like). In these circumstances, the illumination instrument 230 may emit light in a steady state or in a pulsing state to notify the user of the detected error.

In addition, the illumination instrument 230 may be automatically activated by the controller device during particular user interface activities. For example, when the user indicates that a new infusion set 146 is attached and should be "primed" to remove air gaps in the tubing 147, the controller device 200 can automatically activate the illumination instrument 230. Such automatic activation may be useful for the user in that the illumination device 230 can be readily directed to inspect the infusion set 146 without having to press a separate sequence of buttons to activate the light source.

In some embodiments, the controller device may include features that limit when the illumination instrument can be activated. For example, the controller device 200 may include an ambient light sensor 226 (FIGS. 9-10) to detect the light level available to the user. If the ambient light level is higher than a particular threshold (e.g., if the user is located in a lighted room or in daylight conditions), the illumination instrument 230 would not be automatically activated as previously described. As such, the battery power can be conserved by reducing the unnecessary illumination effects. In addition, the ambient light sensor 226 may be used by the controller device 200 to conserve battery power in other ways. For example, the lighting for display device 222 of the user interface 220 can be automatically adjusted based on the lighting condition detected by the ambient light sensor 226. The backlight for the display device 222 may be automatically reduced by the controller device 200 if the user is located in high-level lighting conditions (e.g., in a lighted room or in daylight conditions). Also, the backlight for the display device 222 may be automatically increased by the controller device 200 if the user is located in low-level lighting conditions.

In another embodiment, the activation of the illumination instrument 230 may be limited by the controller device 200 for reasons other than ambient lighting conditions. For example, the illumination instrument 230 may be limited if the controller device 200 detects that the remaining capacity of the power source reaches below a threshold level. In such circumstances, the battery power can be automatically reserved for use in operating the drive system to deliver medicine to the user. Alternatively, the illumination instrument 230 may be limited by the controller device 200 based on a power use profile. The power use profile can provide an estimate of remaining battery life based on the user's activity with the infusion pump system 10 (e.g., activations of the drive system to provide basal and bolus dispensations, historical interaction with the user interface 220, history of activating the illumination tool, and the like). Using this power use profile, the controller device 200 can estimate how long the remaining battery power will last in order to dispense the medicine remaining in the cartridge 120. If the power use profile indicates that the remaining battery power may be insufficient, particular features such as the illumination tool 230 may be limited or shut off in order to conserve the remaining battery power for activating drive system and indicating alarms. In another example, the controller device 200 may limit the number of uses of the illumination instrument 230 to a preset number of activations per day or per attachment of a new pump device 100. Again, providing a limit on the number of activations can conserve the battery power for other operations such as alarm indications and the drive system.

Referring now to FIGS. 11-16, the infusion pump system 10 can be operated such that the pump device 100 is a disposable, non-reusable component while the controller device 200 is a reusable component. In these circumstances, the pump device 100 may be configured as a "one-time-use" device that is discarded after the medicine cartridge is emptied, expired, or otherwise exhausted. Thus, in some embodiments, the pump device 100 may be designed to have an expected operational life of about 1 day to about 30 days, about 1 day to about 20 days, about 1 to about 14 days, or about 1 day to about 7 days—depending on the volume of medicine in the cartridge 120, the dispensation patterns that are selected for the individual user, and other factors. For example, in some embodiments, the medicine cartridge 120 containing insulin may have an expected usage life about 7 days after the cartridge is removed from a refrigerated state and the septum 121 is punctured. In some circumstances, the dispensation pattern selected by the user can cause the insulin to be emptied from the medicine cartridge 120 before the 7-day period. If the insulin is not emptied from the medicine cartridge 120 after the 7-day period, the remaining insulin may become expired sometime thereafter. In either case, the pump device 100 and the medicine cartridge 120 therein can be discarded after exhaustion of the medicine cartridge 120 (e.g., after being emptied, expired, or otherwise not available for use).

The controller device 200, however, may be reused with subsequent new pump devices 100' and new medicine cartridges 120'. As such, the control circuitry, the user interface components, and other components that may have relatively higher manufacturing costs can be reused over a longer period of time. For example, in some embodiments, the controller device 200 may be designed to have an expected operational life of about 1 year to about 7 years, about 2 years to about 6 years, or about 3 years to about 5 years—depending on a number of factors including the usage conditions for the individual user. Accordingly, the user is permitted to reuse the controller device 200 (which may include complex or valuable electronics) while disposing of the relatively low-cost pump device 100 after each use. Such a pump system 10 can provide enhanced user safety as a new pump device 100' (and drive system therein) is employed with each new fluid cartridge 120.

Referring to FIGS. 11-12, the pump device 100 can be readily removed from the controller device 200 when the medicine cartridge 120 is exhausted. As previously described, the medicine cartridge 120 is inserted into the cavity 116 (FIG. 1) of the pump housing 110 where it is retained by the cap device 130. In some embodiments, a portion of the pump housing 110 can comprise a transparent or translucent material so that at least a portion of the medicine cartridge 120 is viewable therethrough. For example, the user may want to visually inspect the medicine cartridge when the plunger 125 is approaching the output end 122 of the medicine cartridge, thereby providing a visual indication that the medicine cartridge may be emptied in the near future. In this embodiment, the barrel 111 of the pump housing 110 comprises a generally transparent polymer material so that the user can view the medicine cartridge 120 to determine if the plunger 125 is nearing the end of its travel length. Optionally, some embodiments of the pump device 100 may include a label 117a that is adhered around the barrel 111. The label 117a may provide a convenient location for basic user instructions, product identification information, and other information related to the infusion pump system 10. To provide enhanced viewability of the medicine cartridge 120 through the label 117a, the label 117a may include a window 117b through which the user may visually inspect if the plunger 125 is nearing the end of its travel length.

As shown in FIG. 11, the pump device 100 has been used to a point at which the medicine cartridge 120 is exhausted. The plunger 125 has been advanced, toward the left in FIG. 11, over a period of time so that all or most of the medicine has been dispensed from the cartridge 120. In some embodiments, the controller device 200 may provide a visual or audible alert when this occurs so as to remind the user that a new medicine cartridge is needed. In addition or in the alternative, the user may visually inspect the medicine cartridge 120 through the barrel 111 of the pump housing 110 (and through the window 117b of the label 117a in this embodiment) to determine if the medicine cartridge 120 is almost empty. When the user determines that a new medicine cartridge 120 should be employed, the pump device 100 can be readily separated from the controller device 200 by actuating the release member 215. In this embodiment, the release member 215 is a latch on the controller device 200 that is biased toward a locking position to engage the pump device 100. The latch may be arranged to engage one or more features on a lateral side of the pump housing 110. As such, the user may actuate the release member 215 by moving the release member 215 in a lateral direction 216 (FIG. 11) away from the pump device 100 (e.g., by applying a force with the user's finger).

As shown in FIG. 12, when the release member 215 is actuated and moved to a position away from the pump device 100, the segmented guide rail 114a-b is free to slide longitudinally in the guide channel 214a-b without interference from the release member 215. Accordingly, the user can move the pump device 100 in a longitudinal direction 217 away from the controller device 200. For example, the segmented guide rail 114a-b may slide along the guide channel 214a-b, the extension 113 (FIG. 1) may be withdrawn from the mating depression 213 (FIG. 12), and the electrical connector 118 can be separated from the mating connector 218. In these circumstances, the pump device 100 is physically and electrically disconnected from the controller device 200 while the pump device retains the exhausted medicine cartridge 120.

In some embodiments, the gasket 140 compressed between the pump device 100 and the controller device 200 may comprise a resilient material. In such circumstances, the gasket 140 can provide a spring-action that urges the pump device 100 to shift a small amount away from the controller device 200 when the release member 215 is moved to the unlocked position (e.g., move in the lateral direction 216 in the embodiment shown in FIG. 11). Accordingly, in some embodiments, the pump device 100 can automatically and sharply move a small distance (e.g., about 0.5 mm to about 5 mm) away from the controller 200 when the release member 215 is moved to the unlocked position. Such an automatic separation provides a convenient start for the user to detach the pump device 100 away from the controller device 200. Furthermore, this automatic separation caused by the spring-action of the gasket 140 can provide a swift disconnect between the electrical connectors 118 and 218 when the pump device 100 is being replaced.

Figure 13:
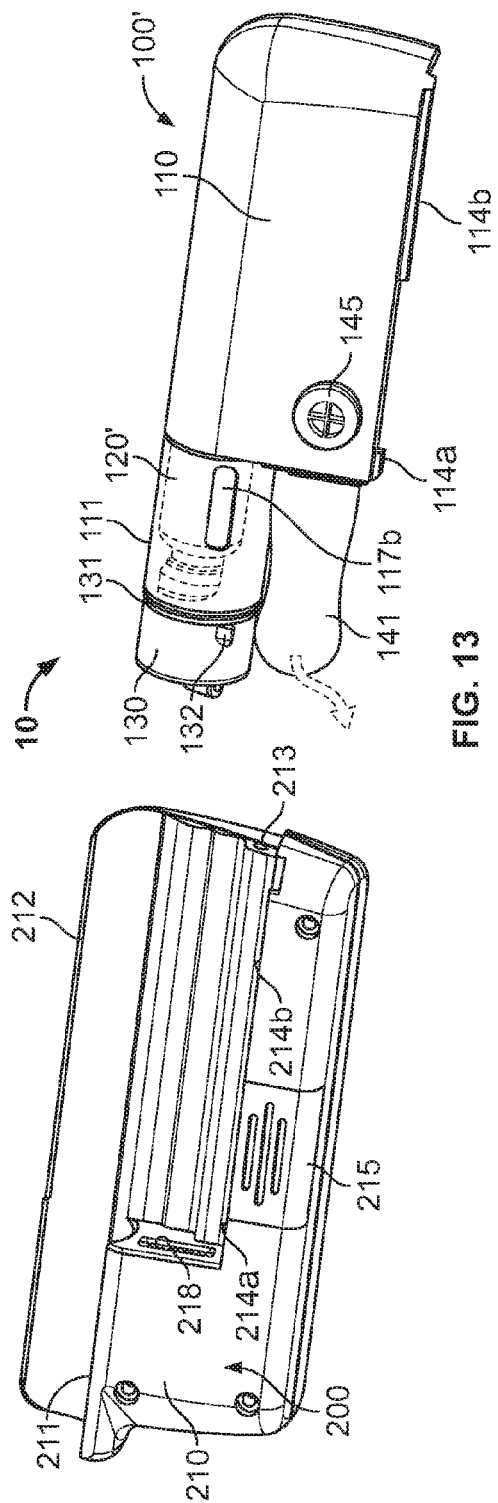
FIGS. 13-14 are perspective views of the pump device of FIGS. 11-12 being discarded and the controller device of FIGS. 11-12 being reused with a new pump device.
Figure 14:
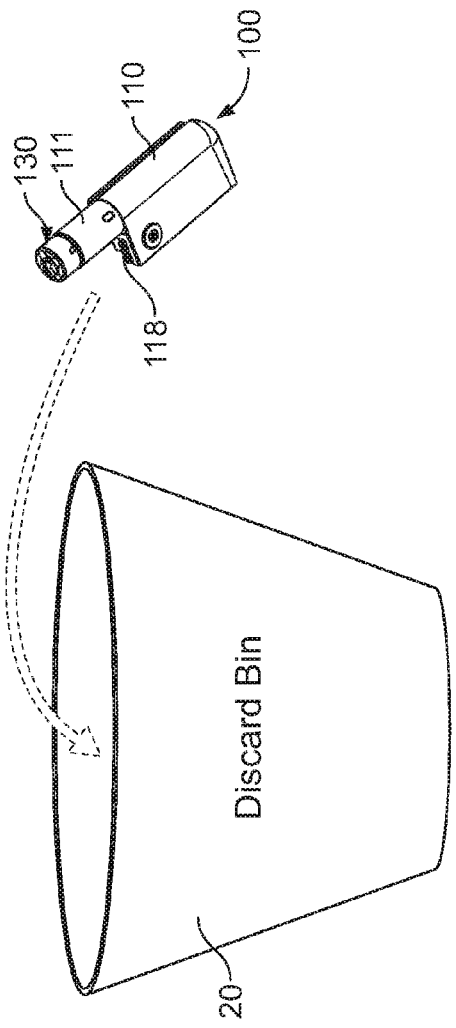

Referring to FIGS. 13-14, the same controller device 200 can be reused with a new pump device 100' having a new medicine cartridge 120' retained therein, and the previously used pump device 100 can be discarded with the exhausted medicine cartridge 120. The new pump device 100' (FIG. 13) can have a similar appearance, form factor, and operation as the previously used pump device 100 (FIGS. 11-12 and 14), and thus the new pump device 100' can be readily attached to the controller device 200 for controlled dispensation of medicine from the new medicine cartridge 120'. In some embodiments, the user may prepare the new pump device 100 for use with the controller device 200. For example, the user may insert the new medicine cartridge 120' in the cavity 116 of the new pump device 100' and then join the cap device 130 to the pump housing to retain the new medicine cartridge 120' therein (refer, for example, to FIG. 1). Although the tubing 147 of the infusion set 146 is not shown in FIG. 13, it should be understood that the tubing 147 may be attached to the cap device 130 prior to the cap device 130 being joined with the housing 110. For example, a new infusion set 146 can be connected to the cap device 130 so that the tubing 147 can be primed (e.g., a selected function of the pump device 100 controlled by the controller 200) before attaching the infusion set patch to the user's skin. As shown in FIG. 13, the new medicine cartridge 120' may be filled with medicine such that the plunger 125 is not viewable through the barrel 111.

As shown in FIG. 14, the previously used pump device 100 that was separated from the controller device (as described in connection with FIGS. 11-12) may be discarded after a single use. In these circumstances, the pump device 100 may be configured as a disposable "one-time-use" device that is discarded by the user after the medicine cartridge 120 is emptied, is expired, has ended its useful life, or is otherwise exhausted. For example, the pump device 100 may be discarded into a bin 20, which may include a trash bin or a bin specifically designated for discarded medical products. Thus, the user is permitted to dispose of the relatively low-cost pump device 100 after each use while reusing the controller device 200 (which may include complex or valuable electronics) with subsequent new pumps 100'. Also, in some circumstances, the infusion set 146 (not shown in FIG. 14, refer to FIG. 8) that was used with the pump device 100 may be removed from the user and discarded into the bin 20 along with the pump device 100. Alternatively, the infusion set 146 can be disconnected from the previous pump device 100 and attached to the new pump device 100'. In these circumstances, the user may detach the infusion set cannula and patch from the skin so as to "re-prime" the tubing with medicine from the new pump device 100' to remove air pockets from the tubing. Thereafter, the infusion set cannula and patch can be again secured to the user's skin.

Figure 15:
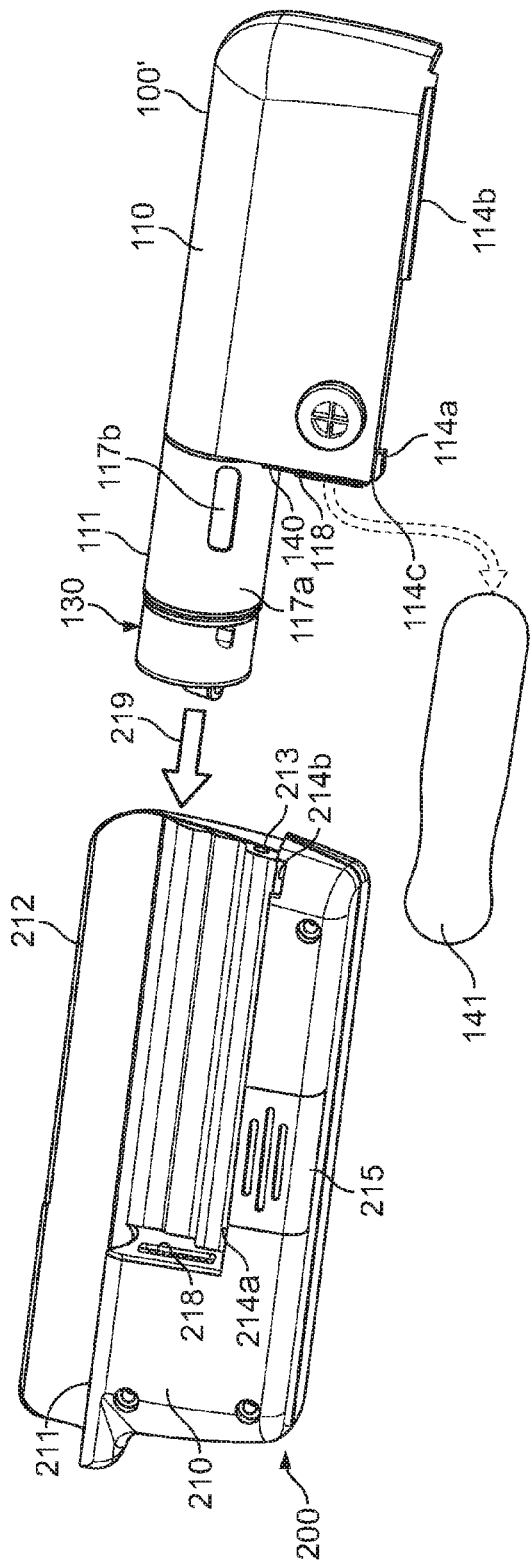
FIGS. 15-16 are perspective views of the new pump device of FIG. 13 being attached to the controller device of FIG. 13.
Figure 16:
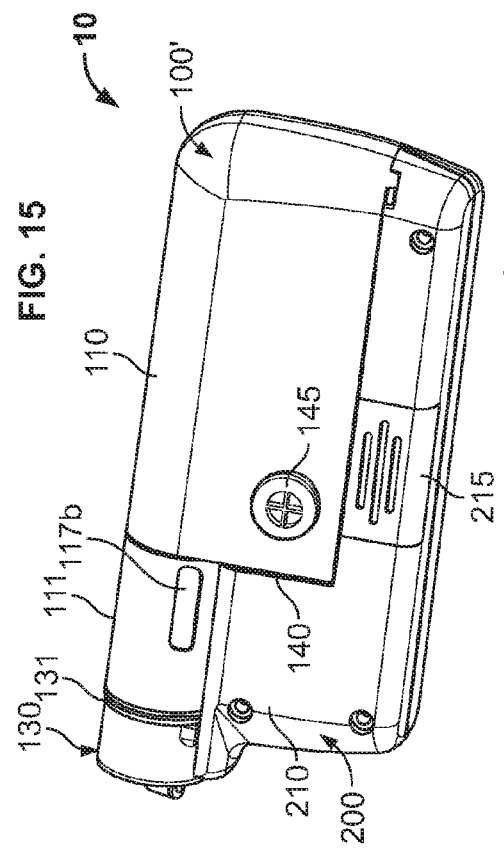

Referring to FIGS. 15-16, the new pump device 100' can be removably attached to the controller device 200 to assemble into the infusion pump system 10 for delivery of medicine to the user. Before the pump device 100 is electrically connected with the controller device 200, the user may prepare the new pump device 100' for use by pulling the removable tab 141 away from the pump housing 110. In this embodiment, the new pump device 100' includes the removable tab 141 to seal the battery in the unused pump device 100' and thereby maintain the battery in a storage mode (refer, for example, to FIG. 14 in which the removable tab 141 is arranged to cover an internal face of the vent 115). As described in more detail below, when the new pump device 100' is prepared for usage, the removable tab 141 can be pulled away from the pump housing 110 (and away from the battery therein), which switches the battery into an activation mode. Thus, the shelf-life of the pump device 100' (prior to usage with the controller device 200) may be extended by sealing the battery in a storage mode because little, if any, energy is dissipated from the battery when in the storage mode.

The new pump device 100' can be connected to the controller device 200 by advancing the new pump device 100' in a longitudinal direction 219 (FIG. 15) toward the controller device 200. When the pump device 100' is advanced in the longitudinal direction 219 toward the controller device 200, the movement is guided by the slider channel 112 (FIGS. 4-5) and the segmented rails 114a-b. In particular, the slider channel 112 of the pump housing engages the rail 212 of the controller housing 210. Also, the front portion of the segmented rail 114a slides into the rear portion of the guide channel 214b. In this embodiment, the front portion of the segmented rail 114a includes a ramp surface 114c (refer also to FIG. 1) that engages a complementary ramp surface 215c (FIG. 4) of the release member 215 to thereby force the release member 215 away from the guide channel 214a-b during advancement of the pump device 100'. The release member 215 is temporarily forced away from the guide channel 214a-b so that the front portion of the segmented rail 114a passes over the release member 215, which enables the electrical connector 118 of the pump device 100' to engage with the mating connector 218 of the controller device 200. As the connectors 118 and 218 join together to form the electrical connection, the release member 215 biased to return to its latched position and is shifted to a position in the guide channel 214a-b between the segmented rails 114a-b so as to prevent withdrawal of the pump device 100'.

Also, when the connectors 118 and 218 are mated, the extension 113 (FIG. 1) and barrel 111 are mated with the corresponding depression 213 and barrel channel 211 so as to resist relative rotational movement between the pump device 100 and the controller device 200. In this embodiment, the physical attachment of electrical connectors 118 and 218 may also serve to resist relative rotational movement between the pump device 100 and the controller device 200. Furthermore, when the connectors 118 and 218 are mated, the slide channel 112 is mated with the corresponding rail 112 (FIG. 1) and barrel channel 211 so as to resist relative side-to-side movement between the pump device 100 and the controller device 200.

As previously described, the guided motion in the longitudinal direction 219 provides the user with a convenient "one-movement" process to attach the pump device 100' and the controller device 200. For example, the user can readily slide the pump device 100' and the controller device 200 toward one another in a single movement (e.g., in the longitudinal direction) that causes both a physical connection and an electrical connection. Thus, the infusion pump system 10 permits users to readily join the pump device 100' and the controller device 200 without compound or otherwise difficult hand movements—a feature that can be beneficial to child users or to elderly users.

As shown in FIG. 16, when the new pump device 100' is fully advanced and attached to the controller device 200, the gasket 140 is compressed between the opposing surfaces of the pump housing 110 and the controller housing 210. Such a configuration provides a water-resistance seal around the electrical connection that protects the sensitive internal components of the pump device 100' and the controller device 200 from damage or malfunction. Although the tubing 147 of the infusion set 146 is not shown in FIGS. 15-16, it should be understood that the tubing 147 may be attached to the cap device 130 to provide a fluid path from the new pump device 100' to the user.

Accordingly, the new pump device 100' can removably attach to the controller device 200 in a manner that provides a secure fitting, an overall compact size, and a reliable electrical connection. When the pump device 100' and the controller device 200 are arranged in this side-by-side configuration, the controller device 200 can be electrically connected with the pump device 100' while the controller device 200 remains outside of the pump housing 110 (and, likewise, the pump device 100 remains outside of the controller housing 210). As such, the overall size of the assembly system 10 can be minimized, thereby providing an infusion pump system having a discrete size and enhanced portability.

Figure 17:
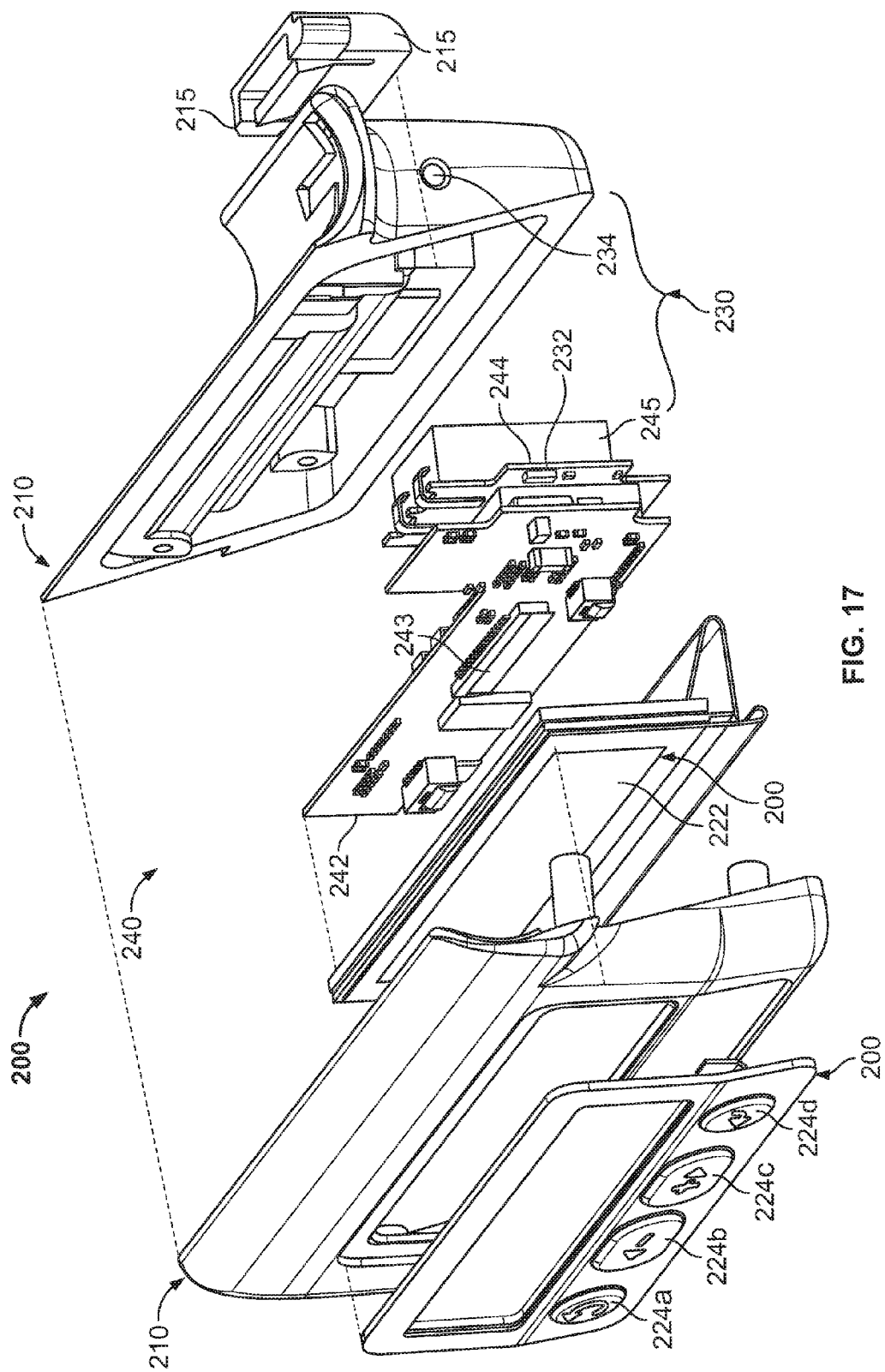
FIG. 17 is an exploded perspective view of a controller device for an infusion pump system, in accordance with some embodiments.

Referring now to FIG. 17, the controller device 200 (shown in an exploded view) houses a number of components that can be reused with a series of successive pump devices 100. In particular, the controller device 200 includes control circuitry 240 arranged in the controller housing 210 that is configured to communicate control signals to the drive system of the pump device 100. In this embodiment, the control circuitry 240 includes a main processor board 242 that is in communication with a power supply board 244. The control circuitry 240 includes at least one processor 243 that coordinates the electrical communication to and from the controller device 200 (e.g., communication between the controller device 200 and the pump device 100). The processor 243 can be arranged on the main processor board 242 along with a number of other electrical components such as memory devices. It should be understood that, although the main processor board 242 is depicted as a printed circuit board, the main processor board can have other forms, including multiple boards, a flexible circuit substrate, and other configurations that permit the processor 243 to operate. The control circuitry 240 can be programmable in that the user may provide one or more instructions to adjust a number of settings for the operation of the infusion pump system 10. Such settings may be stored in the memory devices arranged in the control circuitry 240. Furthermore, the control circuitry 240 may include one or more dedicated memory devices that store executable software instructions for the processor 243. The control circuitry 240 may include other components, such as sensors, that are electrically connected to the main processor board 242. For example, at least a portion of the occlusion sensor 250 (not shown in FIG. 17) can be electrically connected to the main processor board 242 via a flexible circuit substrate or one or more wires, as described in more detail below in connection with FIG. 26.

As previously described, the controller device 200 can be electrically connected with the pump device 100 via mating connectors 118 and 218 (FIGS. 4-5) so that the control circuitry 240 can communicate control signals to the pump device 100 and receive feedback signals from components housed in the pump device 100. In this embodiment, the electrical connector 118 (FIG. 5) on the pump device 100 is a z-axis connector, and the connector 218 (FIG. 4) on the controller device 200 is adapted to mate therewith. The electrical connector 218 on the controller device 200 is in communication with the control circuitry 240. As such, the processor 243 can operate according to software instructions stored in the memory device so as to send control signals to the pump device 100 via the connector 218.

Also as previously described, the controller device 200 can include the illumination instrument 230 that may be operated by the controller circuitry 240. For example, the illumination instrument 230 can include an LED device 232 that is electrically activated by the control circuitry 240 according to the user's input or according to the previously described automated conditions. The light emitted from the LED device 232 can be transmitted through a light guide 234 arranged on the external face of the controller housing 210. It should be understood that, in other embodiments, the illumination instrument 230 may include other light source configurations.

Still referring to FIG. 17, the user interface 220 of the controller device 200 can include input components, output components, or both that are electrically connected to the control circuitry 240. For example, in this embodiment, the user interface 220 includes a display device 222 having an active area that outputs information to a user and four buttons 224a-d that receive input from the user. Here, the display 222 may be used to communicate a number of settings or menu options for the infusion pump system 10. In this embodiment, the control circuitry 240 may receive the input commands from the user's button selections and thereby cause the display device 222 to output a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge 120, or the like). As previously described, the controller circuit 240 can be programmable in that the input commands from the button selections can cause the controller circuit 240 to change any one of a number of settings for the infusion pump system 100.

Some embodiments of the control circuitry 240 may include a cable connector (e.g., a USB connection port or another data cable port) that is accessible on an external portion of the controller housing 210. As such, a cable may be connected to the control circuitry 240 to upload data or program settings to the controller circuit or to download data from the control circuitry 240. For example, historical data of medicine delivery can be downloaded from the control circuitry 240 (via the cable connector) to a computer system of a physician or a user for purposes of analysis and program adjustments. Optionally, the data cable may also provide recharging power.

Still referring to FIG. 17, the control circuitry 240 of the controller device 200 may include a second power source 245 that can receive electrical energy from a first power source 345 (FIG. 18) housed in the pump device 100. In this embodiment, the second power source 245 is coupled to the power supply board 244 of the control circuitry 240. The hard-wired transmission of the electrical energy can occur through the previously described connectors 118 and 218 (FIGS. 4-5). In such circumstances, the first power source 345 (FIG. 18) may include a high density battery that is capable of providing a relatively large amount of electrical energy for its package size, while the second power source 245 (FIG. 17) may include a high current-output battery that is capable discharging a brief current burst to power the drive system 105 of the pump device 100. Accordingly, the first battery 345 disposed in the pump device 100 can be used to deliver electrical energy over time (e.g., "trickle charge") to the second battery 245 when the controller device 200 is removably attached to the pump device 100. For example, as previously described, the first battery 345 may comprise a zinc-air cell battery. The zinc-air cell battery 345 may have a large volumetric energy density compared to some other battery types. For example, the zinc-air cell battery 345 may have a volumetric energy density of greater than about 900 Watt-hours/Liter (Wh/L), about 1000 Wh/L to about 1700 Wh/L, and about 1200 Wh/L to about 1600 Wh/L. Also, the zinc-air cell battery may have a long storage life, especially in those embodiments in which the battery is sealed (e.g., by the removable tab 141 or the like) during storage and before activation. One exemplary zinc-air cell battery provides a potential voltage of about 1.1V to about 1.6V (about 1.2V to about 1.4 V, and about 1.3 V in one embodiment), a current output of about 8 mA to about 12 mA (about 10 mA in one embodiment), and a storage capacity of greater than about 600 mA·h (about 650 mA·h in one embodiment).

As shown in FIG. 17, the second battery 245 may include a high current-output device that is housed inside the controller housing 210. The second battery 245 can be charged over a period of time by the first battery 345 and then intermittently deliver high-current bursts to the drive system 105 over a brief moment of time. For example, the second battery 245 may comprise a lithium-polymer battery. The lithium polymer battery disposed in the controller device 200 may have an initial current output that is greater than the zinc-air cell battery disposed in the pump device 100, but zinc-air cell battery may have an energy density that is greater than the lithium polymer battery (e.g., the lithium polymer battery disposed in the controller device 200 may have a volumetric energy density of less than about 600 Wh/L). In addition, the lithium-polymer battery 245 is readily rechargeable, which permits the zinc-air battery 345 disposed in the pump device 100 to provide electrical energy to the lithium-polymer battery 245 for purposes of recharging. One exemplary lithium-polymer battery provides a initial current output of about greater than 80 mA (about 90 mA to about 110 mA, and about 100 mA in one embodiment) and a maximum potential voltage of about 4.0V to and 4.4V (about 4.2 V in one embodiment). In other embodiments, it should be understood that the second power source 245 may comprise a capacitor device capable of being recharged over time and intermittently discharging a current burst to activate the drive system 105.

Accordingly, the infusion pump system 10 having two power sources 345 and 245—one arranged in the pump device 100 and another arranged in the reusable controller device 200—permits a user to continually operate the controller device 200 without having to recharge a battery via a wall-plug or other cable. Because the controller device 200 can be reusable with a number of pump devices 100 (e.g., attach the new pump device 100' after the previous pump device 100 is expended and disposed), the second power source 245 in the controller device can be recharged over a period of time each time a new pump device 100 is connected thereto. Such a configuration can be advantageous in those embodiments in which the pump device 100 is configured to be a disposable, one-time-use device that attaches to a reusable controller device 200. For example, in those embodiments, the "disposable" pump devices 100 recharge the second power source 245 in the "reusable" controller device 200, thereby reducing or possibly eliminating the need for separate recharging of the controller device 200 via a power cord plugged into a wall outlet.

Figure 18:
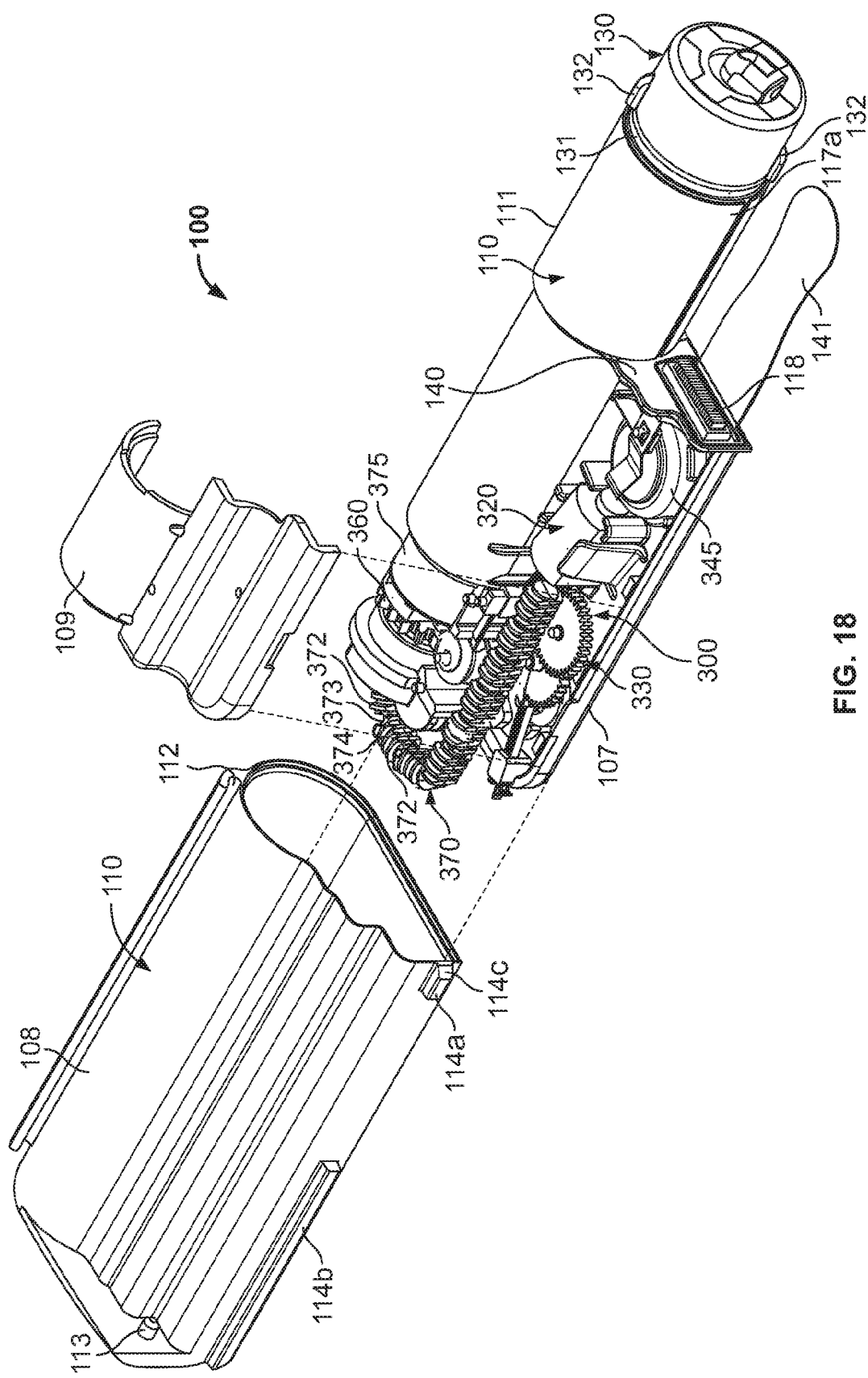
FIG. 18 is an exploded perspective view of a pump device for an infusion pump system, in accordance with some embodiments.
Figure 20:
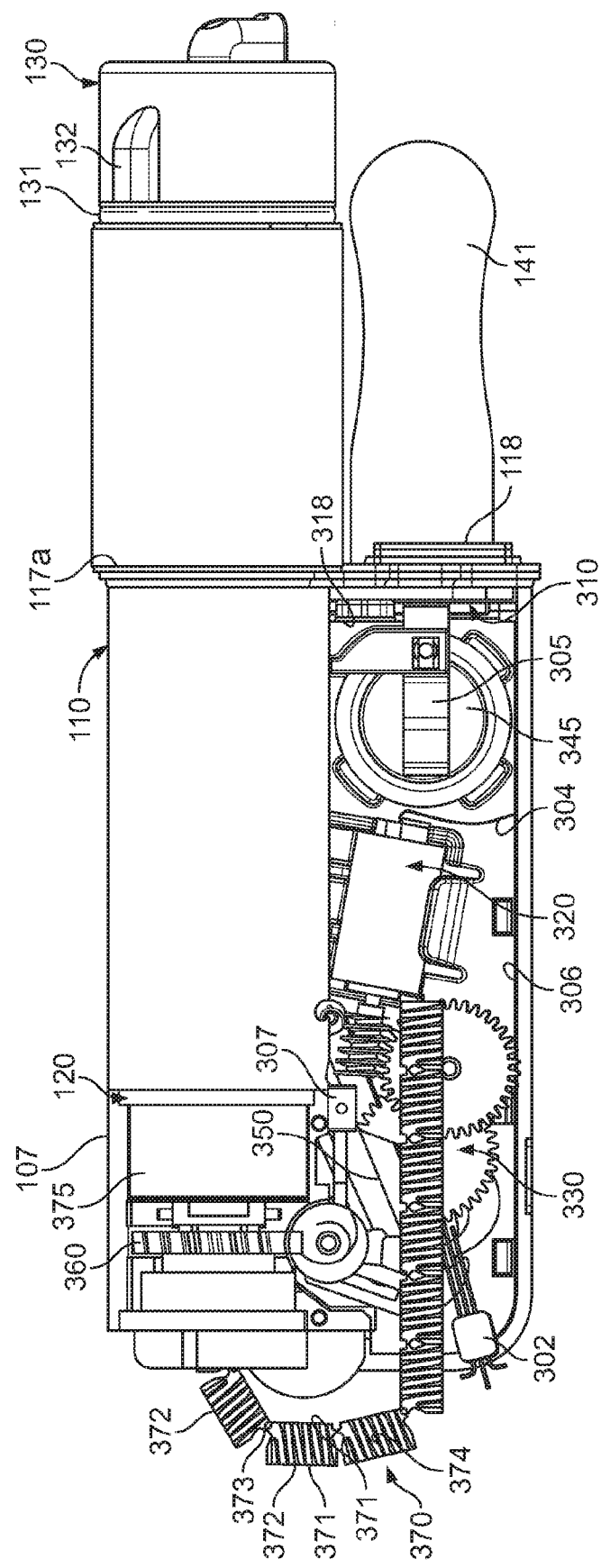
FIG. 20 is a top view of a portion of the pump device of FIG. 18.

Referring now to FIGS. 18-20, the pump device 100 may include a drive system 300 that is controlled by the removable controller device 200 (FIGS. 1-5). Accordingly, the drive system 300 can accurately and incrementally dispense fluid from the pump device 100 in a controlled manner. The drive system 300 may include a flexible piston rod 370 that is incrementally advanced toward the medicine cartridge 120 so as to dispense the medicine from the pump device 100. At least a portion of the drive system 300 is mounted, in this embodiment, to the pump housing 110. In this embodiment, the pump housing 110 includes a chassis 107, a shell portion 108, and a cover mount 109. The shell portion 108 can be used to cover at least a portion of the drive system 300. For example, the shell 108 may include an inner curved surface against which a curved section of a piston rod 370 rests. The cover mount 109 may be assembled to the chassis 107 of the pump housing 110 to secure some components of the drive system 300 in position between the cover mount 109 and the chassis 107. When the cover mount 109 is assembled into place, the "unused" or retracted portion of the piston rod 370 may rest in a channel defined in the top of the cover mount 109. The shell portion 108 can slide over the cover mount 109 and join with the chassis 107 to form the assembled pump housing 110.

Some embodiments of the drive system 300 may include a battery powered actuator (e.g., reversible motor 320 or the like) that resets a ratchet mechanism 330, a spring device 350 (FIG. 22) that provides the driving force to the ratchet mechanism 330, and a drive wheel 360 that is rotated by the ratchet mechanism 330 to advance the flexible piston rod 370 toward the medicine cartridge 120. The operation of the drive system 300 is described in more detail below in connection with FIGS. 22-25.

As shown in FIGS. 19-20, the pump device 100 can include one or more motion detectors coupled with the drive system 300 to provide feedback regarding the operation of the drive system 300. For example, the pump device 100 may include a first motion detector 302 configured as a limit switch that detects when a portion of the ratchet mechanism has reached the limit of its travel and must thereafter stop movement or reverse direction. The operation of the limit switch 302 is described in more detail below in connection with FIGS. 22-25. In another example, the pump device 100 may include a second motion detector 307 in the form of a mechanical error switch that indicates whether components of the drive system 300 completed the desired motion for each drive cycle. The operation of the mechanical error switch 307 is described in more detail below in connection with FIGS. 22-25.

Referring to FIGS. 19-20, the pump device 100 includes a connector circuit 310 to facilitate the transfer of signals to and from the electrical connector 118. As previously described, the electrical connector 118 of the pump device 100 mates with the connector 218 (FIG. 4) of the controller device 200 so that electrical communication can occur between the pump device 100 and the controller device 200. The connector circuit 310 may comprise a generally non-complex circuit 310 that does not include a processor or other relatively high-cost components. In this embodiment, the connector circuit 310 operates as a passageway for the control signals (from the control circuitry 240 (FIG. 17) of the controller device 200) to transmit to the drive system 300 (e.g., to the actuator 320). For example, the reversible motor 320 may be connected to the connector circuit 310 via one or more wires 304. The connector circuit 310 also operates as a passageway for the electrical power from the first battery 345 (FIG. 19) to pass to the controller device 200 for recharging of the second battery 245 (FIG. 17). For example, the first battery 345 may be connected to the connector circuit 310 via one or more power contacts 305. Furthermore, the connector circuit 310 operates as a passageway for feedback signals (e.g., from the motion detectors 302 and 307) to transmit to the control circuitry 240 (FIG. 17) of the controller device 200. For example, the limit switch 302 may be connected to the connector circuit 310 via one or more wires 306 (the one or more wires connecting the mechanical error switch 307 to the connector circuit 310 are not shown in FIGS. 19-20).

In some embodiments, the connector circuit 310 in the pump device 100 includes a memory device 318 that can store data regarding the pump device 100 and its operational history. For example, the memory device 318 of the connector circuit 310 may include a flash memory chip that is configured to store data such as: a unique serial number designated for the pump device 100, a manufacturer identifier code, and a drive cycle counter. The unique serial number designated for the pump device 100 and the manufacturer identifier code may be useful pieces of quality control information that remains with the pump device 100 throughout its shelf-life and operational life. If, for example, a manufacturing error is identified for a particular pump device 100, the unique serial number and the manufacturer identifier code (e.g., a lot code) can be used to promptly identify the manufacturing location and its manufacturing lot.

The drive cycle counter stored in the memory device 318 can be useful for maintaining an accurate estimate of the volume of medicine that remains in the medicine cartridge 120. For example, the number of drive cycles that are required to incrementally advance the plunger 125 and thereby dispense a full medicine cartridge 120 may be a predetermined value (e.g., in some embodiments, 6,300 drive cycles result in full dispensation of a new medicine cartridge). Accordingly, the drive cycle counter stored in the memory device 318 can keep track of the number of drive cycles that have occurred through the operational life of the pump device 100. Each time the motor 320 completes a new drive cycle and incrementally advances the piston rod 370 to dispense some medicine, the controller device 200 can store an updated value for the drive cycle counter stored in the memory device 318. When the updated value stored in drive cycle counter stored in the memory device 318 approaches the predetermined value, the controller device 200 can alert the user that the medicine cartridge is approaching exhaustion. Furthermore, because the memory device 318 is arranged in the pump device 100, the drive cycle counter stored in the memory device 318 remains local to the pump device 100. If the pump device 100 is temporarily disconnected from the controller device 200 and then reconnected (or reconnected to a different controller device 200), the controller device 200 can retrieve the value for the drive cycle counter stored in the memory device 318 and promptly ascertain how much medicine remains in the medicine cartridge 120.

Still referring to FIGS. 19-20, in some embodiments, the flexible piston rod 370 comprises a plurality of segments 372 serially connected by hinge portions 373 so that the flexible piston rod 370 is adjustable from a curved shape to a noncurved shape. The plurality of segments 372 and the interconnecting hinge portions 373 can be integrally formed in one piece from one or more moldable materials, including polymer materials such as Nylon or POM. In this embodiment, each of the plurality of rod segments 372 includes an exterior thread pattern 374 along at least one cylindrical surface portion. The piston rod 370 also includes a plunger engagement device 375 can be arranged at a forward end of the piston rod 370. As such, the plunger engagement device 375 faces toward the medicine cartridge 120 when the medicine cartridge 120 is inserted into the cavity 116. In some embodiments, the plunger engagement device 375 may comprise a pusher disc that abuts against the plunger 125 of the medicine device (refer, for example, to FIG. 21).

Referring to FIG. 21, some embodiments of the piston rod 370 can be optionally configured to attach with the medicine cartridge 120 when the medicine cartridge 120 is advanced into the cavity 116. For example, when the cap device 130 (refer to FIG. 1) is attached to the pump housing 110 to retain the medicine cartridge 120 therein, a portion of the cap device 130 can push upon the body of the cartridge 120. As shown in FIG. 21, a longitudinal force 140 may be applied to the medicine cartridge 120 during engagement of the cap device 130 to the pump housing 110. This longitudinal force 140 can be used to urge a portion of the medicine cartridge 120 (e.g., the plunger 125 in this embodiment) to secure to a plunger engagement device 375 (FIG. 21) that is optionally included on the piston rod 370. In some embodiments, the plunger engagement device 375 may include penetration members 376 (three such members 376 in the example depicted in FIG. 21) that penetrate into the plunger 125 of the medicine cartridge 120 and thereby secure the medicine cartridge 120 to the piston rod 170. (It should be understood that FIGS. 18-19 depicts the piston rod 370 arranged in the pump housing 110 of the pump device 100, and FIG. 21 shows a similar view with the piston rod 370 with other portions of the pump device 100 removed for purposes of illustrating the piston rod 370 and medicine cartridge 120.) In this embodiment, the plunger engagement device 375 includes a plurality of penetration members 376 that extend from a pusher disc 378 toward the plunger 125 and are configured to penetrate into the plunger 125 in response to the longitudinal force 140 (FIGS. 7B and 10). Thereafter, the plunger 125 may remain secured to the piston rod 370 during operation of the pump device 100, which may serve to reduce the compliance of the plunger material and thereby increase the dosage accuracy. Furthermore, the penetration members 376 secure the plunger 125 to the drive system (e.g., to the piston rod 370 in this embodiment), so the plunger 125 does not necessarily become displaced when the medicine cartridge 120 is impacted. For example, if the pump device 100 is dropped on the ground and undergoes an impact, the plunger 125 may be retained in its position relative to the wall of the cartridge 120 due to the attachment with the piston rod 370 via the penetration members 376.

In some embodiments, the flexible piston rod 370 can include an anti-rotation structure that hinders the piston rod 370 from rotating with the drive wheel 360 (thereby allowing the rotation of the drive wheel 360 to translate into a longitudinal motion of the piston rod 370). For example, as shown in FIGS. 19-21, the flexible piston 370 includes longitudinal flat surfaces 371 extending along each of the segments 372. The longitudinal flat surfaces 371 can engage a complementary surface on the pump housing 110 (not shown in FIGS. 19-21) proximate the drive wheel 360 so that the flexible piston rod 370 is hindered from rotating when the drive wheel 360 turns. Accordingly, the longitudinal flat surfaces 371 on each segment 372 align to form a key that is received in a mating keyway (e.g., a complementary flat surface) on the pump housing. In other embodiments, the anti-rotation structure may include one or more longitudinal channels (with each channel capable of engaging an associated protrusion that acts as a key to hinder rotation while permitting longitudinal motion) or the like.

Because the flexible piston rod 370 is adjustable from a curved shape to a noncurved shape, the overall length of the pump device can be reduced in some embodiments. For example, in a typical infusion pump that houses a straight and rigid rod, the typical infusion pump requires a package or housing having a linear dimension sufficient to accommodate the length of the rigid piston rod when it is at its limit of travel in which it is fully withdrawn from the container or cylinder. The pump device 100 incorporating the flexible piston rod 370 can require less space than a similar device that houses a non-flexible, rigid rod.

Referring now in more detail to the components of the drive system 300 depicted in FIGS. 22-25, the electrically powered actuator may be in the form of the motor 320 having a rotatable output shaft 321. In this embodiment, the motor 320 is reversible in that can receive signals that cause the output shaft 321 to rotate in a first rotational direction or in a second, opposite rotational direction. One example of a suitable motor 320 is a coreless DC motor with reversible rotation capabilities. As previously described, the operation of the motor 320 can be controlled by the removable controller device 200 (FIGS. 1-5) via electrical signals communicated through the mating electrical connectors 118 and 218 (FIGS. 4-5).

Still referring to FIGS. 22-25, a gear system 322 may be coupled to the motor 320 so that actuation by the motor 320 causes a pusher arm 325 to act upon the ratchet mechanism 330 or to decouple from the ratchet mechanism 330. In this embodiment, the gear system 322 includes a worm gear 323 and a gear reduction assembly comprising spur gears 324a, 324b, and 324c. As described in more detail below, one of the spur gears (e.g., segmented gear 324c) may engage the limit switch 302 when it reaches the opposite ends of its reciprocating motion, thereby indicating that the motor 320 should reverse its rotational direction or stop rotating.

The pusher arm 325 can be pivotably coupled to the gear 324c so that partial rotation of the gear 324c causes the pusher arm to reciprocate within a guide slot 328. The guide slot 328 can be formed in the body of the chassis 307 (FIGS. 18-20) of the pump housing. The pusher arm 325 can have a slider pin 326 that fits into the guide slot 328 are reciprocates therein.

Accordingly, rotation of the motor 320 in a first direction can be translated into an advancement force to the pusher arm 325. The advancement force on the pusher arm 325 is applied to a pawl member 335, which (in this embodiment) causes the pawl member 335 to pivot to a reset position (refer to FIG. 29). In addition, rotation of the motor 320 in a second direction can be translated into an refraction force to the pusher arm 325, which can cause the pusher arm 325 to be separated from the pawl member 335 during the drive step (refer to FIG. 25). As such, the motor 320, the gear system 322, and the pusher arm 325 can collectively operate as an actuator assembly that provides a reliable and consistent adjustment of the ratchet mechanism 330 during a reset step (refer to FIG. 24). Moreover, this actuator assembly (e.g., the motor 320, the gear system 322, and the pusher arm 325) can be activated to separate from the pawl member 335, thereby permitting the motor 320 to decouple from the ratchet mechanism 330 during a drive step (refer to FIG. 25).

Figure 22:
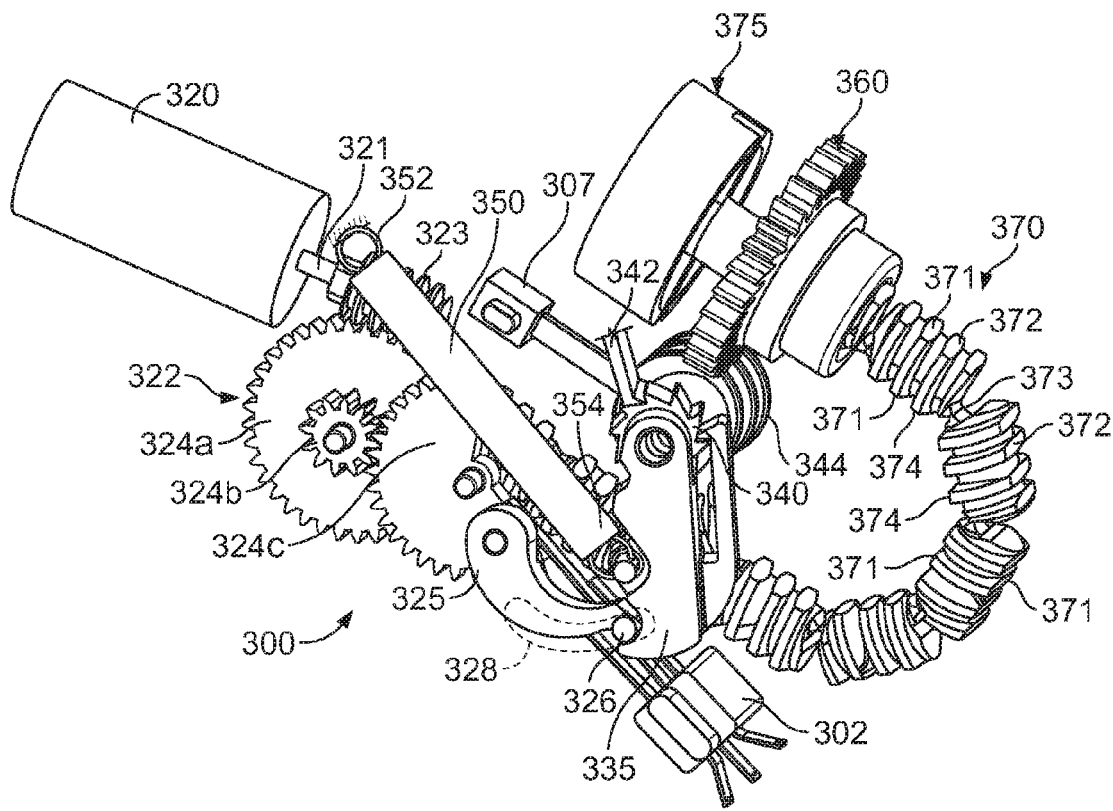
FIGS. 22-25 are perspective views of a portion of a drive system for the pump device of FIG. 18.

Referring to FIG. 22, the motion path of the pusher arm 325 can be configured to provide an efficient mechanical advantage orientation during the desired motion of the adjustable pawl member 335. In this embodiment, the pusher arm 325 is directed by the guide slot 328 formed in an interior surface of the pump housing 110. In this embodiment, the pusher arm 325 includes the slider pin 326 that is received within the guide slot 328 during assembly of the pump device 100. The portion of the pusher arm 325 proximate the slider pin 326 can abut against the pawl member 335 when the pusher arm 325 is advanced. As such, when a first end of the pusher arm 325 is moved by the gear 324c, a second end of the pusher arm (proximate the slider pin 326) is directed by the guide slot 328. The orientation of the pusher arm 325 relative to the guide slot 328 can be configured to provide an efficient mechanical advantage for the pushing force applied by the pusher arm 325 during the desired motion of the adjustable pawl member 335.

Still referring to FIG. 22, the ratchet mechanism 330 includes the pawl member 335 and a ratchet body 340, which in this embodiment is a ratchet wheel having a number of teeth along its circumferential surface. In this embodiment, the ratchet wheel 340 is coupled with a worm gear 344, and incremental rotation of the ratchet wheel 340 causes rotation of a drive wheel 360 (due to engagement with the worm gear 344). The pawl member 335 is adjustable between a reset position (refer to FIG. 24) and a forward position (refer to FIG. 25). For example, during the reset step, the motor 320 may be activated to advance the pusher arm 325 (guided by the guide slot 328), and the pusher arm 325 then applies a pushing force that adjusts the pawl member 335 to the reset position in which the pawl member 335 grabs a new tooth of the ratchet wheel 340 (refer to FIG. 24). In this embodiment, the adjustable pawl member 335 is pivotably coupled to about the axis of rotation for the ratchet wheel 340 and the worm gear 344.

Figure 24:
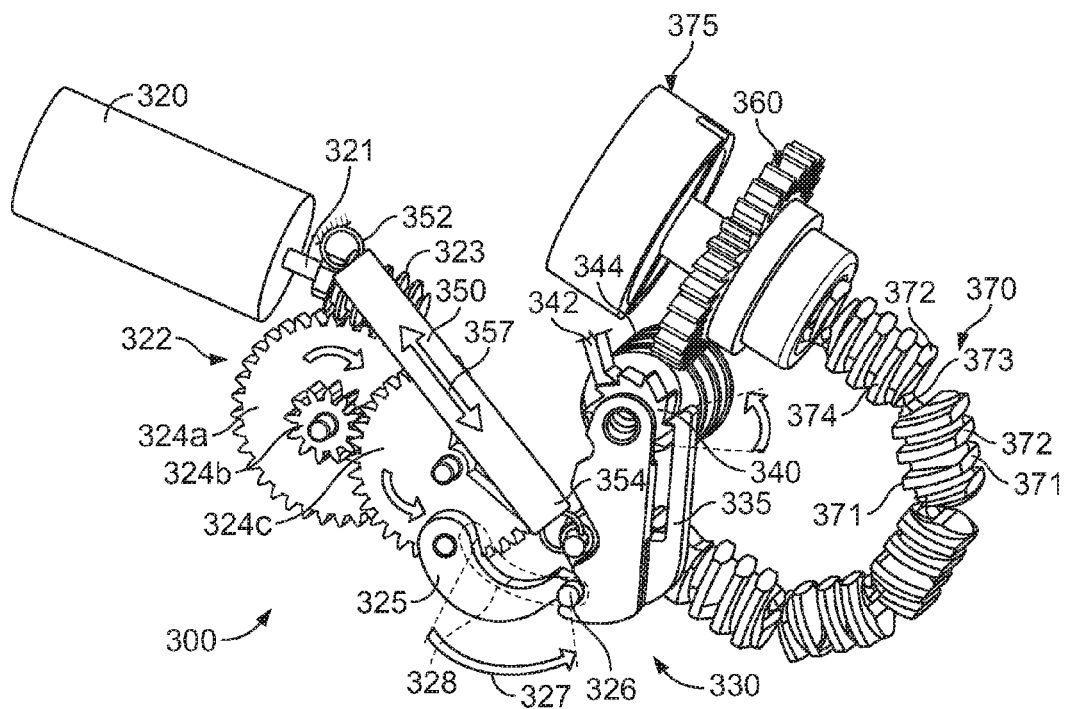
Figure 25:
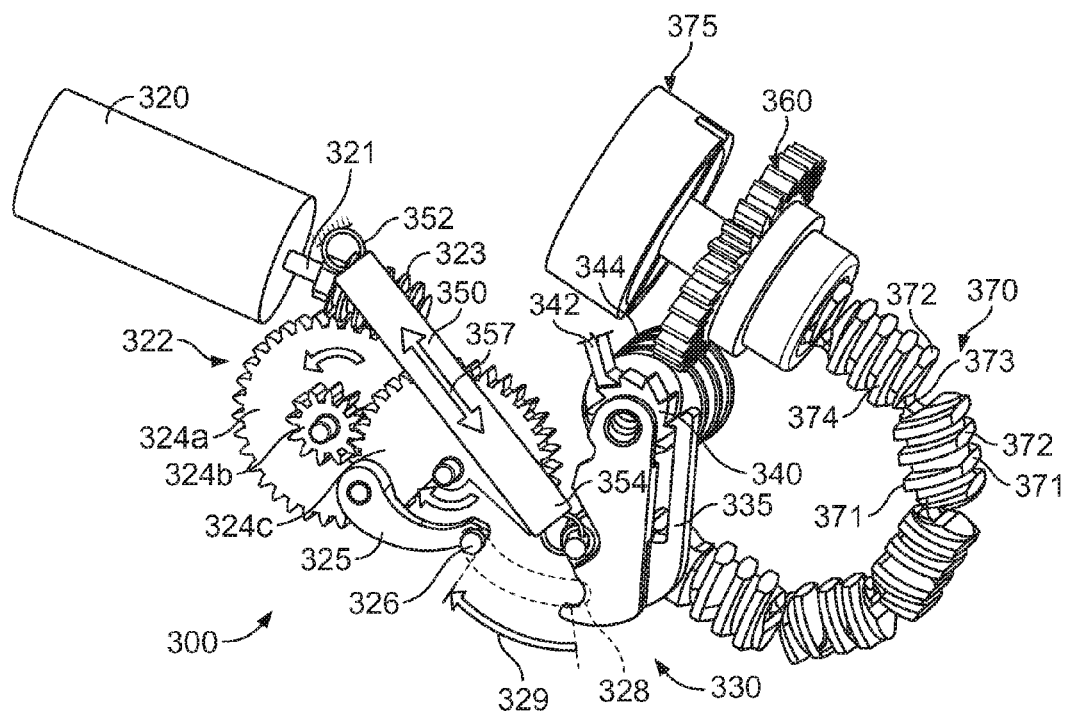

A spring device 350 is also coupled to the pawl member 335 so as to urge the pawl member 335 toward the forward position (refer to FIG. 25). In this embodiment, the spring device 350 is in the form of a coil spring that is fixed to the pump housing 110 (not shown in FIGS. 22-25) at a first end portion 352 and that is engaged with the pawl member 335 at a second end portion 354. Thus, as shown in FIG. 24, when the pawl member 335 is adjusted to the reset position, the spring device 350 is in tension and stores potential energy that urges the pawl member 335 to return to the forward position (refer to FIG. 25) and thereby drive the ratchet wheel 340 in a forward rotational direction.

In some embodiments, a locking pawl 342 can be used to prevent the ratchet wheel 340 from reverse motion. The locking pawl 342 can flex or otherwise adjust to permit the incremental forward rotation of the ratchet wheel 340. As such, the adjustable pawl member 335 can adjust from the forward position (refer to FIG. 28) to the reset position (refer to FIG. 29) to engage a new tooth of the ratchet wheel 340 while the ratchet wheel 340 remains in position due to the locking pawl 342.

Still referring to FIG. 22, in some embodiments the ratchet wheel 340 can be integrally formed with the worm gear 344 so that the incremental rotation of the ratchet wheel 340 is translated to the worm gear 344. Such rotation of the worm gear 344 causes rotation of the drive wheel 360. The drive wheel 360 includes a central aperture having an internal thread pattern therein (not shown in FIG. 22), which mates is an external thread pattern 374 on the rod segments 372. Thus, the incremental motion provided by the ratchet mechanism 330, the pusher arm 325, and the motor 320 causes the drive wheel 360 to incrementally rotate, which in turn translates to a longitudinal advancement of the flexible piston rod 370.

Accordingly, in these embodiments, the piston rod 370 may undergo only forward or positive longitudinal displacement as a result of drive system 300. For example, the drive system 300 substantially hinders the piston rod 370 from retracting or "backing up" in response to fluid pressure in the medicine cartridge 120 or other reversal forces. In such circumstances, the flexible piston rod 370 can be retracted only upon manual disassembly of the pump device 100 (e.g., to disengage the drive gear 360 or the ratchet mechanism 330). In those embodiments in which the pump device 100 is intended to be disposable and non-reusable, the non-retractable piston rod configuration may facilitate a "one time use" disposable pump device by hinder attempts to insert a new medicine cartridge 120 in a previously used pump device 100. Such a configuration can thereby reducing the likelihood of failure due to non-intended repeated use of the disposable pump device 100.

Figure 23:
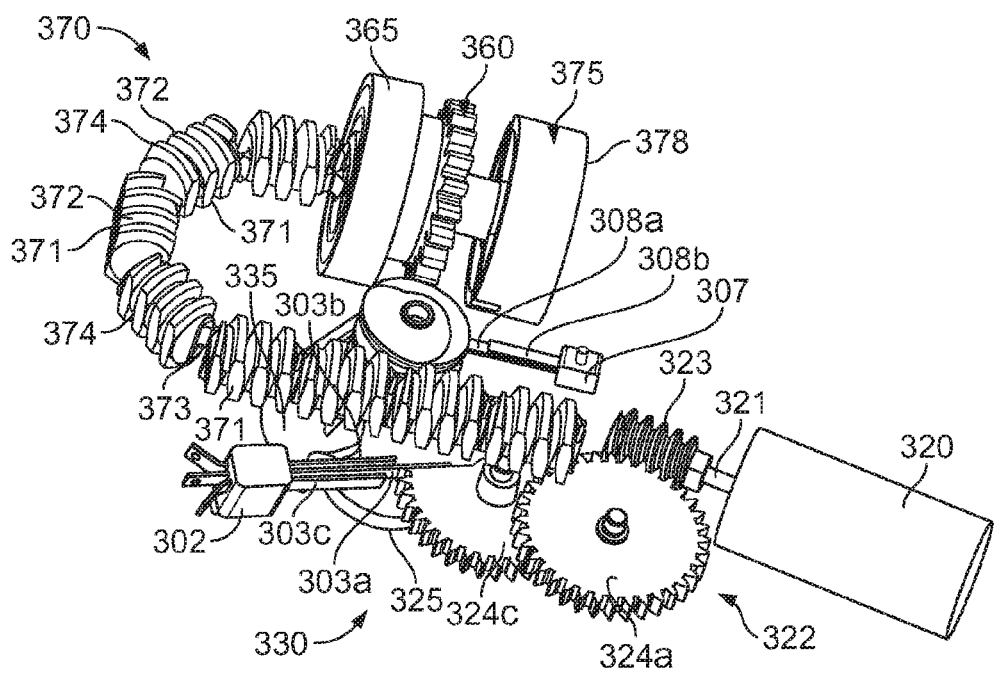

In the embodiment depicted in FIGS. 22-23, the pump device includes at least two motion detectors 302 and 307. As previously described, the first motion detector 302 may comprise a limit switch that is activated when the segmented gear 324c of the gear system 320 reaches the ends of its reciprocating travel path. For example, as shown in FIG. 23, the limit switch 302 may include a middle arm 303a that is arranged between two lateral arms 303b-c. When the motor 320 rotates and causes the segmented gear 324c to rotate in a first direction along its travel path, the middle arm 303a of the limit switch 302 engages a first wall of the segmented gear 324 when the gear 324 reaches the end of its travel path. This causes the middle arm 303a to flex and thereby contact one of the lateral arms 303b, which signals to the controller device 200 that the gear 324c (and the rotational motor 320) reached the end of its travel path. Thereafter, the controller device 200 signals the motor 320 to reverse its rotation, which causes the segmented gear to reciprocate back toward the opposite end of its travel path. When the segmented gear 324c reaches the opposite end of its travel path, the middle arm 303a of the limit switch 302 engages a second wall of the segmented gear 324. This causes the middle arm 303a to flex and thereby contact the opposite lateral arm 303c, which signals to the controller device 200 that the gear 324c (and the rotational motor 320) reached the opposite end of its travel path. Thereafter, the controller device 200 signals the motor 320 to cease rotation until a later time when a new drive cycle is signaled.

As previously described, the second motion detector 307 may comprise a mechanical error switch that is activated when the worm gear 344 is incrementally rotated with each drive cycle. For example, as shown in FIG. 23, mechanical error switch 307 may include a first arm 3083a that is arranged adjacent to a second arm 308b. The first arm 308a has a longer length so that is can be engaged by the threads of the worm gear 344. Accordingly, when the drive system 300 operates to incrementally rotate the worm gear 344, the first arm 308a is temporarily flexed into contact with the second arm 308b. This temporary contact signals to the controller device 200 that the ratchet mechanism 330 and spring 350 successfully translated the drive energy to rotate the worm gear 344 (which rotates the drive gear 360 and thereby advances the piston rod 370).

Accordingly, the pump device 100 can include one or more motion detectors coupled with the drive system 300 to provide feedback regarding the operation of the drive system 300. It should be understood that, in other embodiments, these detectors can be optical, magnetic, or other contact-type sensors. The detectors can be capable of transmitting signals that indicate when components of the drive system 300 (e.g., one of the gears in the gear system 322, the pusher arm 325, or the pawl member 335) has completed a particular motion. Such detector signals may be transmitted to the motor 330, to the controller device 200 (FIGS. 1-5), or a combination thereof.

Referring now to FIGS. 24-25, the incremental motion cycle of the drive system 300 may include rotation of the motor 320 so that the pusher arm 325 is advanced from a first position to act upon the pawl member 335 and then retracted back to the first position. Such movement of the pusher arm 325 can cause the pawl member 335 to adjust from the forward position, to the reset position (refer to FIG. 24), and back to the forward position (refer to FIG. 25) under the driving force of the spring device 350. The adjustment of the pawl member 352 from the reset position to the forward position drives the ratchet wheel 340 and worm gear 344, which incrementally rotates the drive wheel 360 and thereby advances the flexible piston rod 370 a longitudinal increment distance. In one example, the drive system 300 can advance the piston rod 370 a longitudinal increment distance of about 16 microns or less (about 4 microns to about 12 microns, about 5 microns to about 9 microns, and preferably about 6 microns to about 8 microns) for each incremental motion cycle of the ratchet mechanism 330.

In this embodiment of the incremental motion cycle, the pawl member 335 begins with the pusher arm 325 retracted in a first position (e.g., the rest position in this embodiment). The adjustable pawl member 335 can be in this forward position, for example, because the drive system 300 previously completed a drive step at an earlier time.

Referring to FIG. 24, in response to the controller device transmitting a signal to initiate the cycle, the motor 320 may begin to rotate in a first rotational direction that advances the pusher arm 325 to push against the pawl member 335. Such movement of the pusher arm 325 causes a pushing force 327 that overcomes the bias of the spring device 350 and adjusts the pawl member 335 toward the reset position (e.g., the reset step). When the adjustable pawl member 335 reaches the reset position, as shown in FIG. 24, the pawl member 335 is capable of engaging a new tooth of the ratchet wheel 340. The locking pawl 342 prevents the ratchet wheel 340 from rotating in a reverse (non-forward) rotational direction while the adjustable pawl member 335 is shifting back to the reset position. Such an adjustment of the pawl member 335 back to the reset position creates a tension force 357 in the spring device 350 (as shown in FIG. 24), thereby storing potential energy to drive the adjustable pawl member 335 and ratchet wheel 340 in a forward rotational direction for the drive step.

Referring to FIG. 25, after the pawl member 335 reaches the reset position, the motor 330 stops rotating in the first rotational direction and reverses to rotate in the second, opposite rotational direction. Such rotation in the second direction by the motor 320 causes the pusher arm 325 to promptly retract to the first position (while guided by the guide slot 328). As such, the spring device 350 begins to urge the pawl member 335 toward the forward position. When the adjustable pawl 335 is driving the ratchet wheel 340 in the forward rotational direction, the potential energy of the spring device 350 is being translated to kinetic energy for the motion of the pawl member 335 and the ratchet wheel 340. Such an adjustment of the pawl member 335 from the reset position to the forward position drives the ratchet wheel 340 and the integrally formed worm gear 344. The incremental rotation of the worm gear 344 results in an incremental rotation by the drive wheel 360, which advances the flexible piston rod 370 a longitudinal increment distance. Such an incremental advancement of the flexible piston rod 370 can cause a predetermined volume of fluid to be dispensed from the cartridge 120. In the event of a subsequent cycle (including the reset step and the drive step), the motor 320 would begin by rotating in the first rotational direction so as to advance the pusher arm 325 yet again. This pattern of cycles may continue until the piston rod 370 has reached the limit of its longitudinal travel.

Figure 28:
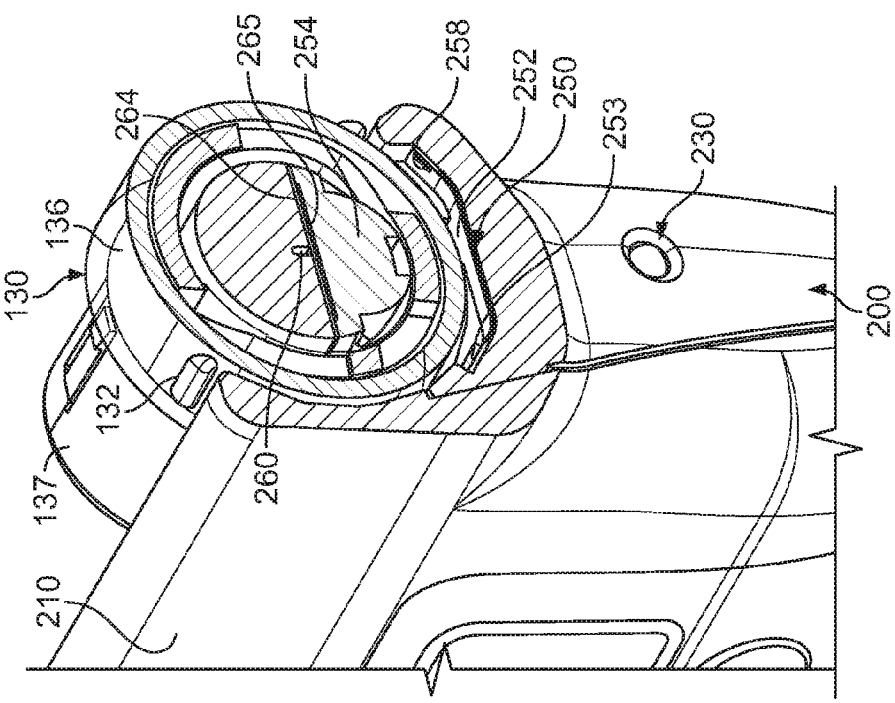

Still referring to FIG. 25, although the pusher arm 325 can be promptly retracted to the first position due to the reverse rotation of the motor 320, the pawl member 335 is driven to the forward position (refer to the motion 329 in FIG. 25) over a greater period of time. This period of time required for the drive step is affected by a number of factors, including the spring force from the spring device 350, the fluid pressure inside the medicine cartridge 120, and the like. Accordingly, the pusher arm 325 can be temporarily separated from the pawl member 335 when it is retracted to its first position, thereby causing the motor 320 to be decoupled from the ratchet mechanism 330 during the drive step. For example, the portion of the pusher arm 325 proximate the slider pin 326 can become temporarily spaced apart by a distance 329 from the pawl member 335 while the pawl member 335 is being driven from the reset position (FIG. 29) to the forward position (FIG. 28). Such a configuration permits the motor 320 to expend a short burst of electrical energy to reset the ratchet mechanism 330 (e.g., during advancement of the pusher arm 325) while contributing no energy during the drive step to drive the ratchet mechanism 330 to the forward position for dispensation of medicine. Because the motor 320 can be decoupled from the ratchet mechanism 330 during the drive step, only the spring device 350 expends energy over a period of time to drive the ratchet mechanism 330 to the forward position. Accordingly, the pump device 100 can reliably and accurately dispense dosages of medicine in a safe and energy efficient manner. In particular, the motor 320 is not required to draw energy from the battery over an extended period of time (e.g., during the drive step in which the piston rod 370 is advanced to dispense medicine over a period of time). Instead, the motor 320 may draw upon the battery power during advancement of the pusher arm 325 to quickly reset the ratchet mechanism 330 and during the brief retraction of the pusher arm 325.

Moreover, the reversible rotation of the motor 320 may provide enhanced safety. As previously described, each drive cycle (including the reset step and the drive step) includes rotation of the motor 320 in a first direction and subsequent rotation in a second opposite direction. Thus, in certain embodiments, if a short-circuit or other malfunction of the motor 320 causes continuous rotation of the motor 320 in one direction, such a malfunction does not result in continuous dispensation (e.g., a possible over dosage) of medicine to the user. Accordingly, the drive system 300 can be reliably operated to dispense the selected dosages of medicine.

Referring now to FIGS. 26-33, the infusion pump system 10 can be equipped with an occlusion sensor that detects occlusions in the fluid flow path extending to the user. For example, the controller device 200 may include an optical sensor system 250 that detects the amount of light reflected from a portion of the cap device 130. In this embodiment, the optical sensor system 250 can detect changes in the amount of light reflected from the cap device 130 in response to an occlusion that causes an increase in the fluid pressure. For example, as described below in connection with FIGS. 32-33, the optical sensor system 250 may operate using the principle of total internal reflection.

Figure 26:
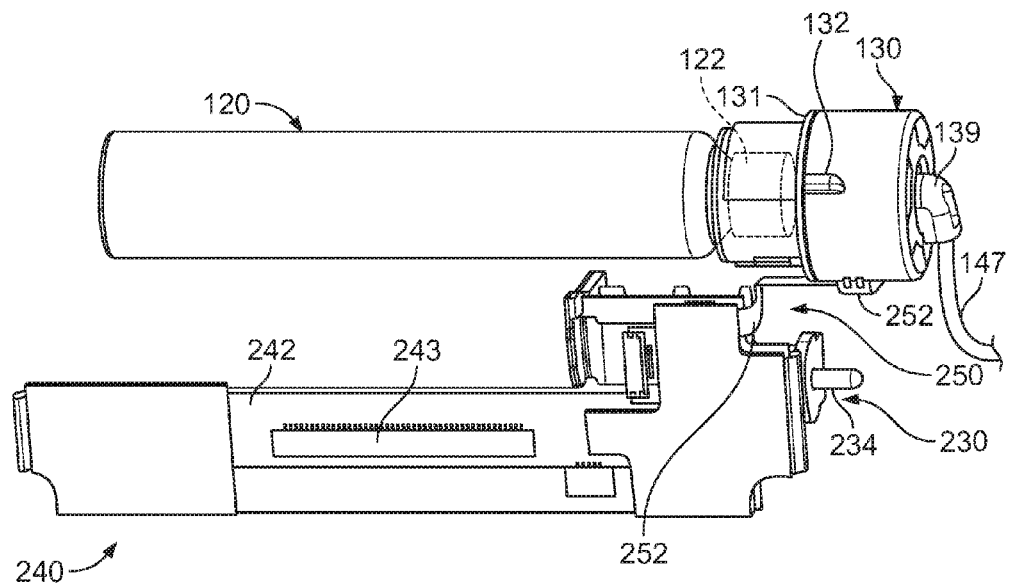
FIG. 26 is a perspective view of occlusion sensor circuitry from a controller device arranged adjacent to a cap of a pump device, in accordance with some embodiments.

Referring to FIG. 26, although the optical sensor system 250 operates to detect changes in the flow path from the pump device 100 (e.g., through the cap device 130), the optical sensor system 250 may include a number of components that are housed in the controller device 200. For example, a light emitter and light sensor may be arranged on a sensor circuit 252 that is housed by the controller device 200, thereby permitting these components to be reused along with the controller device (while the relatively low cost components in the pump device 100 are discarded after the "one time use" of the pump device 100). The sensor circuit 252 can be arranged so that the cap device 130 is aligned with the light emitter and the light sensor (described below) when the pump device 100 is attached to the controller device 200. It should be understood that the pump housing 110 and the controller housing 210 have been removed from FIG. 26 for purposes of showing the relative position of the sensor circuit 252 (in the controller device 200 as shown in FIGS. 4-5) and the cap device 130 (attached to the pump housing 110 as shown in FIG. 4-5).

The sensor circuit 252 can be connected to the control circuitry 240 of the controller device 200 (FIG. 17) via a flexible circuit substrate or one or more wires. In this embodiment, the sensor circuit 252 connects with the main processor board 242 via a flexible circuit substrate. As such, the control circuitry 240 can receive sensor signals and employ detection software stored in one or more memory devices to determine if an occlusion exists. If the sensor signals from optical sensor system 250 indicate that an occlusion exists in the fluid flow path, the controller device 200 can trigger an alert to inform the user. The alert may include a visual or audible alarm communicated via the user interface 220 of the controller device 200.

Figure 27:
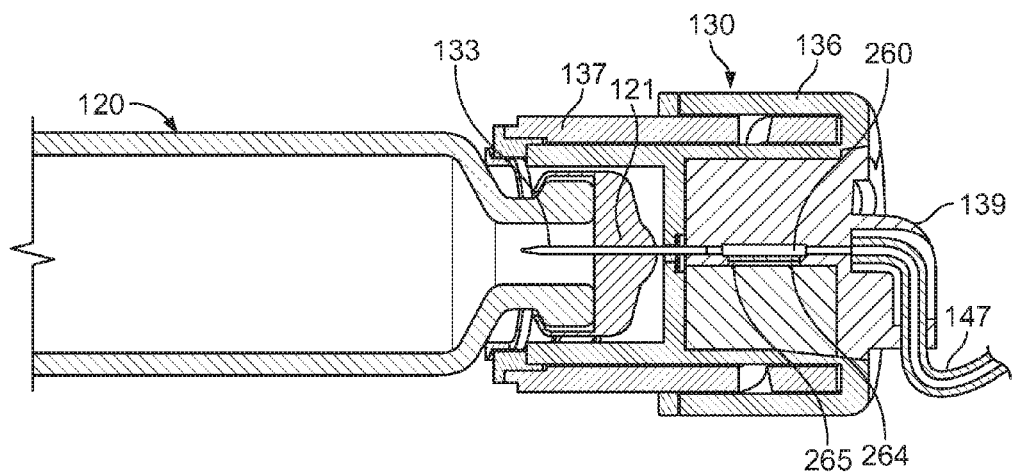
FIG. 27 is a cross-sectional view of the cap device of FIG. 26.

Referring to FIG. 27, the cap device 130 can have a multi-piece construction that provides a flow path from the medicine container 120 to the output port 139 (and to the infusion set tubing 147). At least a portion of the flow path through the cap device 130 may be monitored by the optical sensor system 250 to determine if an occlusion exists downstream of the cap device 130 (e.g., if a kink or clog exists in the infusion set tubing 147 of cannula 149). The multi-piece construction of the cap device 130 can facilitate proper alignment of the cap device 130 and proper engagement with the medicine cartridge 120 during attachment of the cap device 130 to the pump housing 110. For example, the cap device 130 may include a first component 136 that is movably engaged with a second component 137. During attachment of the cap device 130 to the pump housing, the first component 136 can be rotated relative to the second component 137, which causes the second component 137 to advance longitudinally toward the medicine cartridge 120. In such circumstances, a needle penetrator 133 attached to the second component 137 can be advanced toward the septum 121 of the medicine cartridge 120 to pierce the septum and open a fluid flow path. The flow path for the medicine that is dispensed from the medicine cartridge 120 can pass through the needle penetrator 133, through a fluid channel 260 (described below), through the infusion set tubing 147, and to the user.

The fluid channel 260 arranged in the cap device 130 may be at least partially defined by a flexible member 264. For example, in this embodiment, one side of the fluid channel 260 is defined by the flexible membrane 264 so that the channel 260 through which the medicine travels includes a portion that is flexible. An air cavity 265 is disposed adjacent to the flexible membrane 264 opposite to the fluid channel 260, thus providing a volume into which the flexible membrane 264 can expand as pressure rises in the fluid channel 260. The flexible membrane 264 may comprise a flexible polymer material that bulges or otherwise deforms as the fluid pressure in the flow channel 260 rises. As such, the flexible membrane 264 can flex into the air cavity 265 when the fluid pressure rises due to an occlusion in the flow path downstream of the fluid channel 260.

Figure 29:
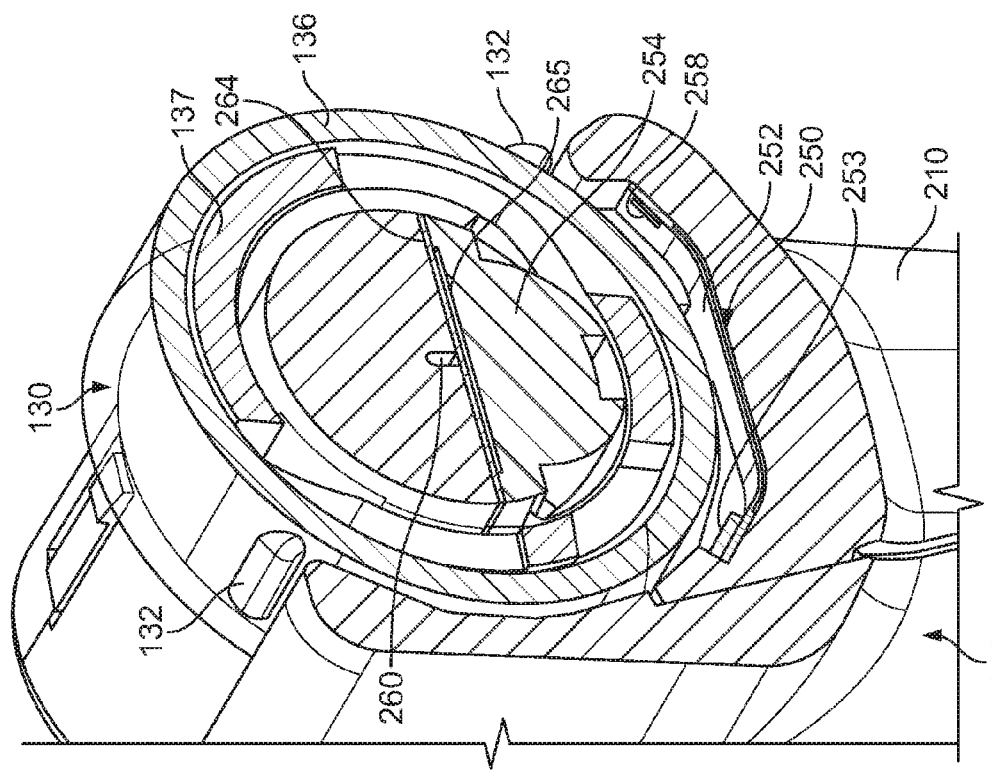
FIGS. 28-29 are cross-sectional views of an occlusion sensor for use in an infusion pump system.

Referring now to FIGS. 28-29, the sensor circuit 252 can be arranged so that fluid channel 260 in the cap device 130 is aligned with the light emitter 253 and the light sensor 258 when the pump device 100 is attached to the controller device 200. Thus, when the infusion pump system 10 is operating to dispense medicine, the light emitter 253 in the controller device 200 can direct light toward the fluid channel 260 in the cap device 130, and the light sensor 258 can receive light reflected from portions of the cap device 130. A cross-section through the cap device 130 and the controller device 200 (refer to FIGS. 28-29) illustrates one example of the alignment. It should be understood from the description herein that other alignment configurations can be implemented so that the light sensor 258 in the reusable controller device 200 is able to detect changes to fluid flow conditions in the pump device 100.

In this embodiment, the sensor circuit 252 is arranged to at least partially extend to the barrel channel 211 (FIGS. 4-5) of the controller device 200 so that the light emitter 253 and the light sensor 258 are positioned adjacent to the cap device 130. As previously described, the tabs 132 of the cap device 130 can be positioned in a manner that facilitates the particular orientation of the cap device 130 relative to the sensor circuit 252. The light from the light emitter 253 can pass through one or more portions of the cap device 130 during its travel toward the fluid channel 260, flexible membrane 264, and air cavity 265. Accordingly, some portions of the cap device 130 may comprise a generally transparent material to permit light transmission therethrough. In this embodiment, the first component 136 of the cap device 130 can include a generally transparent polymer material. Also, in some embodiments, some portions of the cap device 130 may include windows or openings to avoid interfering with the light from the light emitter 253. For example, the second component 137 may includes openings at selected locations so that light from the light emitter 253 can pass by the second component 137 and to the internal light transmissive member 254.

Still referring to FIGS. 28-29, the internal light transmissive member 254 can be configured to receive light from the light emitter 253, transmit at least a portion of that light toward the fluid channel 260. In this embodiment, the internal light transmissive member 254 comprises a generally transparent polymer material that is capable of light transmission. As described in more detail below, the light that is transmitted in the transmission member 254 toward the fluid channel 260 can (in some circumstances) reflect from the interface where the internal light transmissive member 254 meets the air cavity 265. This reflected light can be further transmitted through the internal light transmissive member 254 to the light sensor 258.

Referring now to FIGS. 30-31, the optical sensor system 250 can be used to detect when an occlusion exists in the flow path from the pump device 100 to the user. For example, when an occlusion occurs in the infusion set tubing 147 (FIGS. 6-7), the delivery of medicine from the infusion pump system 10 to the user can be stopped or otherwise limited. If the user is unaware of the occlusion, the user may be deprived of the intended dosages of medicine from the infusion pump device for a period of time. Accordingly, the optical sensor system 250 can be used to detect when such occlusions occur in the flow path to the user, and the controller device 200 can thereafter alert the user of the occlusion when particular conditions are met. The user may then inspect the pump device 100 or the infusion set 146 to eliminate the occlusion.

As shown in FIG. 30, when no substantial occlusion exists in the flow path, the medicine can be dispensed under normal operating conditions from the medicine cartridge 120, through the cap device 130, and into the infusion tubing 147. In these normal operating conditions, the fluid pressure of the medicine passing through the cap device 130 may be below a selected threshold value. As such, the flexible membrane 264 that is adjacent to the fluid channel 260 is not substantially deformed (e.g., the membrane 264 does not flex downwardly into the air cavity 265 to abut the internal light transmissive member 254). In these circumstances, the light from the light emitter 253 can be reflected at the interface where the internal light transmissive member 254 meets the air cavity 265. In some embodiments, this light reflection may occur due to total internal reflection that the interface. Total internal reflection can occur in some circumstances when light passes through a first medium (e.g., the internal light transmissive member 254) and strikes an interface between the first medium and a second medium (e.g., the air cavity 265) at an angle greater than the critical angle. If the refractive index of the second medium (e.g., the air cavity 265) is lower than refractive index of the first medium (e.g., the internal light transmissive member 254), the light may undergo total internal reflection within the first medium.

For example, as shown in FIG. 30, the light emitter 253 can be an infrared light emitted that is directed toward the internal light transmissive member 254. The infrared light passes through the generally transparent first component 136 of the cap device 130 and then strikes a curved surface 255 of the internal light transmissive member 254. The infrared light may be refracted at the interface with the internal light transmissive member 254. The curved surface 255 may operate as a focusing lens that directs the infrared light toward the air cavity 265 proximate to the fluid channel 260. When the medicine is dispensed under normal operating conditions, the flexible membrane 264 does not flex downwardly into the air cavity 265 to abut the internal light transmissive member 254. Accordingly, the infrared light passing through the internal light transmissive member 254 reflects at the interface where the internal light transmissive member 254 meets the air cavity 265. This reflected light continues through the internal light transmissive member 254 toward a second curved surface 257. The second curved surface 255 may operate as a focusing lens that directs the infrared light toward the light sensor 258. The light sensor 258 may comprise an infrared photo detector that is capable of converting the receipt of infrared light into electrical signals. These electrical signals from the light sensor 258 can be transmitted via the sensor circuit 252 to the control circuitry 240 (FIGS. 17 and 26) for processing to determine if an occlusion alarm should be provided to the user.

As shown in FIG. 31, when an occlusion exists in the flow path, the fluid pressure of the medicine passing through the cap device 130 may rise to a level above the threshold value. For example, if pump device 100 attempts to dispense another incremental dosage medicine when the infusion set tubing 147 is clogged or kinked, the fluid pressure upstream of the occlusion (e.g., in the medicine cartridge 120 and in the cap device 130) may be increased. In these circumstances, the flexible membrane 264 that is adjacent to the fluid channel 260 may be substantially deformed (e.g., the membrane 264 will flex downwardly into the air cavity 265 to abut the internal light transmissive member 254.)

The interface where the internal light transmissive member 254 meets the flexible membrane 264 (FIG. 31) provides different optical results than the previously described interface where the internal light transmissive member 254 meets the air cavity (FIG. 30). In particular, the amount of light from the light emitter 253 that is internally reflected at the interface where the internal light transmissive member 254 meets the flexible membrane 264 is measurably less (as illustrated by the dotted lines in FIG. 31). For example, none of the light or some other reduced portion of light from the light emitter 253 is internally reflected. (The light that is not internally reflected at this interface may pass into the medium of flexible membrane 264 as illustrated, for example, in FIG. 33.) If any portion of the light is internally reflected, this reduced portion of reflected light continues through the internal light transmissive member 254 toward a second curved surface 257 and then toward the light sensor 258. As previously, the light sensor 258 may comprise an infrared photo detector that is capable of converting the receipt of infrared light into electrical signals. Because amount of light that is internally reflected in the light transmissive member 254 is measurably less, the light sensor 258 can produce detection signals that are different from those described in connection with FIG. 30. These detection signals may indicate that the fluid pressure in the cap device 130 has risen above a threshold level due to a downstream occlusion. Again, these detection signals from the light sensor 258 can be transmitted via the sensor circuit 252 to the control circuitry 240 (FIGS. 17 and 26) for processing to determine if an occlusion alarm should be provided to the user.

Figure 32:
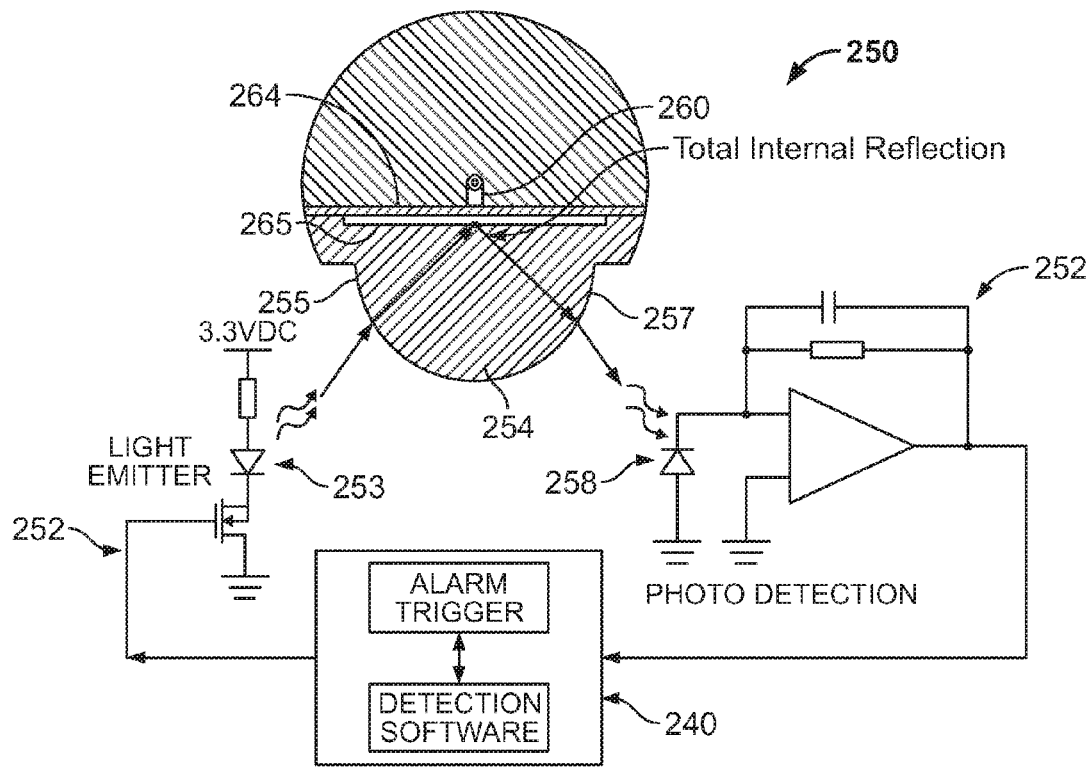
FIGS. 32-33 are diagrams of the occlusion sensor of FIGS. 30-31.
Figure 33:
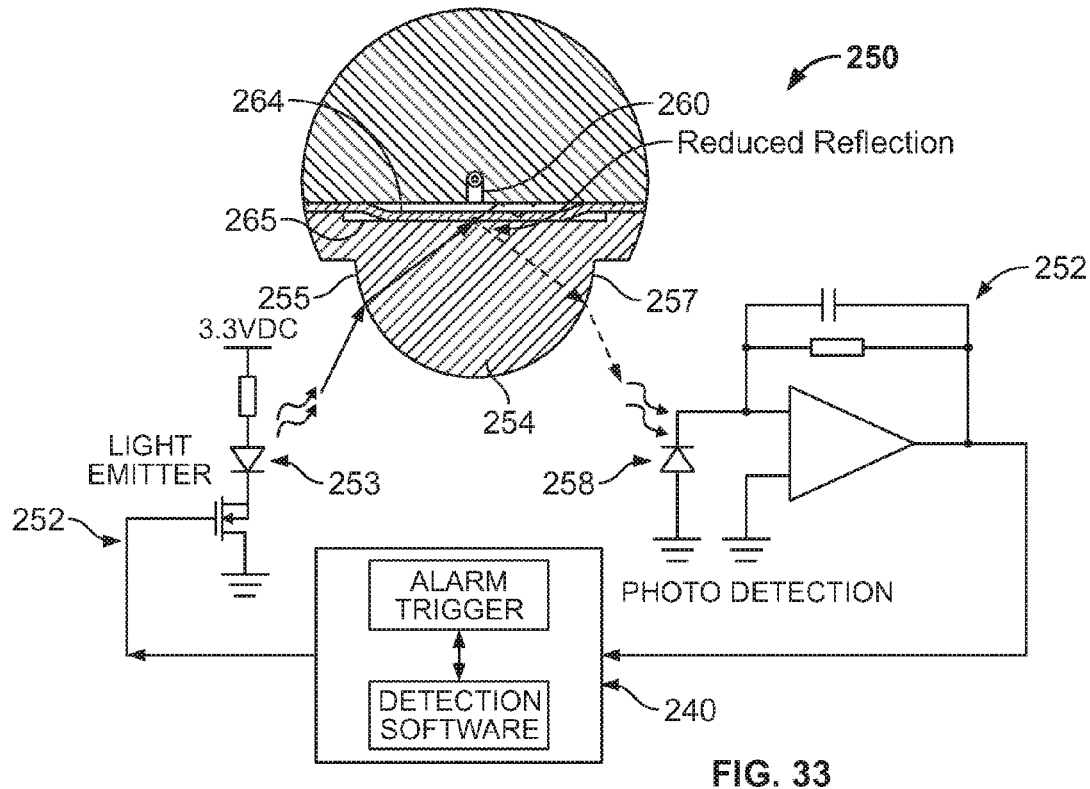

Referring to FIGS. 32-33, the process of determining whether an occlusion exists can be implemented using the control circuitry 240 of the controller device 200. In particular, the control circuitry 240 can be used to activate the light emitter 253 and the light sensor 258 at selected times to monitor the fluid pressure in the flow path. For example, the control circuitry 240 can activate the light emitter 253 and the light sensor 258 one or more times before the drive system 300 (FIGS. 18-20) is activated to force medicine from the medicine cartridge 120, while the drive system 300 is activated, or after the drive system 300 is activated. The control circuitry 240 can receive detector signals from the light sensor 258 and thereafter process the data to determine if an alarm should be triggered to notify the user of an occlusion.

Referring to FIG. 32, in this embodiment, the control circuitry 240 can activate the sensor circuit 252 one or more times shortly before the drive system 300 (FIGS. 18-20) is activated to force medicine from the medicine cartridge 120. When the sensor circuit 252 is activated, the light emitter 253 emits light toward the internal light transmissive member 254. The light from the light emitter 253 can be in the form of an infrared light beam. As shown in FIG. 32, when no substantial occlusion exists in the flow path, the fluid pressure of the medicine passing through the cap device 130 may be below a selected threshold value. In these circumstances, the flexible membrane 264 that is adjacent to the fluid channel 260 is not substantially deformed (e.g., the membrane 264 does not flex downwardly into the air cavity 265 to abut the internal light transmissive member 254). As previously described in connection with FIG. 30, the light from the light emitter 253 can be reflected at the interface where the internal light transmissive member 254 meets the air cavity 265. In some embodiments, this light reflection may occur due to total internal reflection at the interface. This reflected light continues through the internal light transmissive member 254 toward a second curved surface 257. The second curved surface 255 may operate as a focusing lens that directs the infrared light toward the light sensor 258. As previously described, in some embodiments, the light sensor 258 may comprise an infrared photo detector that is capable of converting the receipt of infrared light into electrical signals. These electrical signals from the light sensor 258 can be transmitted via the sensor circuit 252 to the control circuitry 240. The control circuitry 240 receives the signals from the light sensor 258 and uses this data to determine if an occlusion alarm should be provided to the user. In this example depicted in FIG. 32, the control circuitry 240 receives signals that indicate the pressure in the fluid channel 260 is within the normal operating range, so the control circuitry would not trigger an alarm for the user.

Referring to FIG. 33, again, the control circuitry 240 can activate the sensor circuit 252 one or more times shortly before the drive system 300 (FIGS. 18-20) is activated to force medicine from the medicine cartridge 120. When the sensor circuit 252 is activated, the light emitter 253 emits light toward the light transmissive member 254. When an occlusion exists in the flow path, the fluid pressure of the medicine passing through the cap device 130 may rise to a level above the threshold value. For example, when one or more earlier drive cycles were attempted while the infusion set tubing 147 is clogged or kinked, the fluid pressure upstream of the occlusion (e.g., in the medicine cartridge 120 and in the cap device 130) can be increased. In these circumstances, the flexible membrane 264 that is adjacent to the fluid channel 260 may be substantially deformed (e.g., the membrane 264 will flex downwardly into the air cavity 265 to abut the light transmissive member 254.) As previously described in connection with FIG. 31, the interface where the light transmissive member 254 meets the flexible membrane 264 (FIGS. 31 and 33) provides different optical results than the previously described interface where the light transmissive member 254 meets the air cavity (FIGS. 30 and 32). In particular, the amount of light from the light emitter 253 that is internally reflected at the interface where the light transmissive member 254 meets the flexible membrane 264 is measurably less (as illustrated by the dotted lines in FIG. 33).

As shown in FIG. 33, the light that is not internally reflected at this interface may pass into the medium of flexible membrane 264 and perhaps into the fluid channel 260. For example, the refractive index of the material of the flexible membrane 264 can be substantially similar to that of the material of the light transmissive member 254. As a result, the light being transmitted through the light transmissive member 254 can pass into the flexible membrane 264 when the membrane 264 flexes into the air cavity 265 and contacts the flat surface of the light transmissive member 254. The light from the light emitter 253 does not undergo total internal reflection at the portion where the flexible membrane 264 interfaces with light transmissive member 254, thereby resulting in reduced amount of light received by the light sensor 258. If any portion of the light is internally reflected, this reduced portion of reflected light continues through the light transmissive member 254 toward a second curved surface 257 and then toward the light sensor 258. Because the amount of light that is internally reflected in the light transmissive member 254 is measurably less, the light sensor 258 can produce detection signals that are different from those described in connection with FIG. 32. These detection signals from the light sensor 258 can be transmitted via the sensor circuit 252 to the control circuitry 240. The control circuitry 240 receives the signals from the light sensor 258 and uses this data to determine if an occlusion alarm should be provided to the user. In this example depicted in FIG. 33, these detection signals may indicate that the fluid pressure in the cap device 130 has risen above the threshold level due to a downstream occlusion.

As previously described, the control circuitry 240 receives the signals from the light sensor 258 and uses this data to determine if an occlusion alarm should be provided to the user. For example, the control circuitry 240 may include a detection software module and an alarm trigger module stored in one or more memory devices (e.g., on the main processor board 242).

The detection software module may include instructions to use the data signals from the light sensor 258 as input data for a comparative algorithm that determines if an occlusion exists. The comparative algorithm can, for example, compare the data values from the light sensor 258 to an initial value recorded when the pump device 100 was initially activated with no occlusions in the flow path. Alternatively, the comparative algorithm can, for example, average the data values from the light sensor 258 recorded over a predetermined period of time (e.g., 2 minutes, 5 minutes, 10 minutes, 30 minutes, or the like) or over a predetermined number of pump drive cycles (e.g., the last 3 drive cycles, the last 5 drive cycles, the last 10 drive cycles). Then, this average value can be compare to an initial value recorded when the pump device 100 was initially activated with no occlusions in the flow path. These comparative algorithms can be used to reduce the instances of "false alarms" that are provided to the user, and in some cases, can be used to reduce error created by noise in the sensor system. It should be understood from the description herein that, in other embodiments, the detection software module may employ other algorithms to process the data and thereby determine if an occlusion exists.

If the detection software module indicates than an occlusion exists, the control circuitry 240 can activate the alarm trigger module to alert the user. The alarm trigger module can be used to activate the user interface 220 (FIGS. 1-2) to communicate one or more alarms. For example, the alarm trigger module of the control circuitry may be used to activate an audible alarm, a visual alarm (e.g., on the display device 222 (FIGS. 1-2)), or a combination thereof. In some embodiments, the alarm trigger module is configured to provide a set of escalating alarms. For example, the first stage of the alarm may include a low intensity audible alert followed by a textual alarm on the display device. If the user does not respond after a predetermined period of time (e.g., 10 seconds, 30 seconds, or the like), the alarm trigger module may then provide a high intensity audible alert (e.g., louder alert) in combination with a visual alarm having image effects on the display device (e.g., a blinking screen, alternating images, or the like). The alarm trigger module may include further stages of alarm if the user does not respond after a predetermined period of time. When the user is alerted to the occlusion in the flow path, the user can inspect the infusion set tubing 147 and the cannula 149 to determine if there is a repairable kink. If the occlusion is substantial, the user can suspend the operation of the infusion pump system 10 and replace the infusion set 146 with a new infusion set 146.

Referring to FIGS. 34-38, some embodiments of the occlusion sensor system 250 may operate to detect changes in the pressure of the fluid even though the flexible membrane is not positioned against the medicine flow path. For example, in this embodiment, the flexible membrane 264' is not positioned against the medicine flow path through the fluid channel 260' of the cap device 130. Instead, the flexible member 264' is arranged near a terminal end of a capillary tube 261' that offshoots from the fluid channel 260'. The capillary tube 261' may have an orientation and size such that a pocket of air is trapped in the capillary tube 261' as the medicine flows through the fluid channel 260' and to the infusion set tubing 147 (e.g., during an initial priming operation or the like). Accordingly, the infusion pump system 10 can operate to dispense the medicine from the cartridge 120 and through the fluid channel 260' without the requirement that the medicine contacts the material of the membrane 264' (described in more detail below in connection with FIGS. 35-36). Furthermore, the capillary tube 261' enables the flexible membrane 264' and air cavity 265' to be arranged in a greater range of positions that are offset from the centrally located fluid channel 260', which can provide a greater angle of incidence for the reflected light within the light transmissive member 254 (described in more detail below in connection with FIGS. 37-38).

Similar to the previous embodiments described in connection with FIG. 27, the cap device 130 has a multi-piece construction that provides a flow path from the medicine container 120, through the fluid channel 260', and to the output port 139 (and then to the infusion set tubing 147). The pressure of the medicine passing through the cap device 130 may be monitored by the optical sensor system 250 to determine if an occlusion exists downstream of the cap device 130 (e.g., if a kink or clog exists in the infusion set tubing 147 of cannula 149). Similar to the previous embodiments described in connection with FIG. 27, the cap device 130 may include a first component 136 that is movably engaged with a second component 137. During attachment of the cap device 130 to the pump housing, the first component 136 can be rotated relative to the second component 137, which causes the second component 137 to advance longitudinally toward the medicine cartridge 120. In such circumstances, the needle penetrator 133 attached to the second component 137 can be advanced toward the septum 121 of the medicine cartridge 120 to pierce the septum and open a fluid flow path. The flow path for the medicine that is dispensed from the medicine cartridge 120 can pass through the needle penetrator 133, through the fluid channel 260', and then to the infusion set tubing 147 for delivery to the user.

Figure 34:
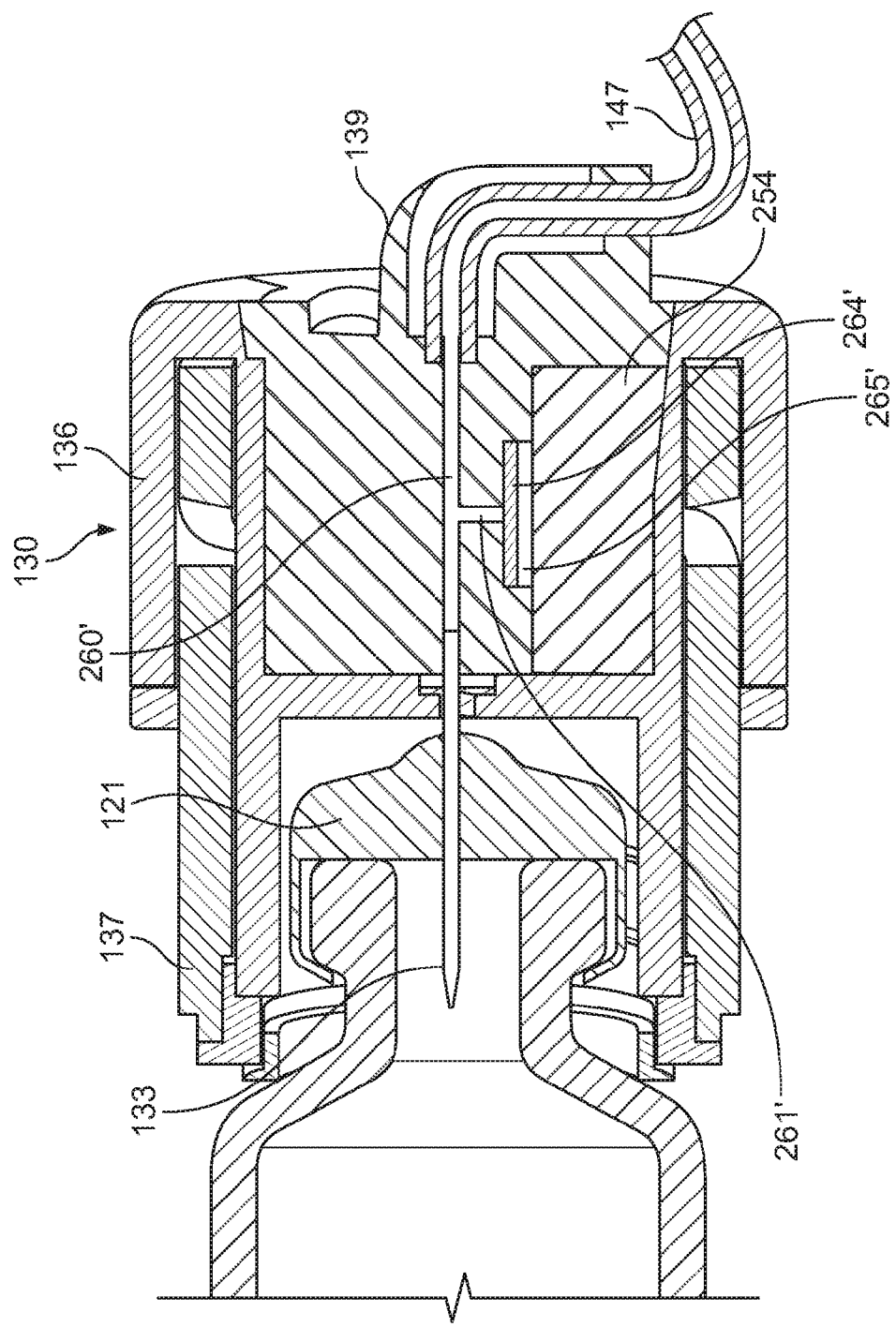
FIG. 34 is a cross-sectional view of an alternative embodiment of the cap device of FIG. 26.

As shown in FIG. 34, the fluid channel 260' arranged in the cap device 130 is defined by one or more rigid side walls, and the capillary tube 261' may extend in a transverse direction from the fluid channel 260'. The capillary tube 261' may have an orientation and size such that the medicine forced through the fluid channel 260' (e.g., during an initial priming operation or the like) does not completely fill the capillary tube 261', but instead traps a pocket of air in the capillary tube 261' as the medicine flows through the channel 260' and to the infusion set tubing 147 (refer, for example, to FIGS. 35-36). The flexible membrane 264' is positioned against a terminal end of the capillary tube 261' so that the air trapped in the capillary tube 261' can apply a pressure to the membrane 264'. An air cavity 265' is disposed adjacent to the flexible membrane 264' opposite to the pocket of air in the capillary tube 261', thus providing a volume into which the flexible membrane 264' can expand as the pressure is applied to the flexible membrane 264'. Similar to previously described embodiments, the flexible membrane 264 may comprise a flexible polymer material that bulges or otherwise deforms as the air pressure in the capillary tube 261' rises (in response to a rise in the fluid pressure in the flow channel 260'). As such, the flexible membrane 264' can flex into the air cavity 265' when the fluid pressure rises due to an occlusion in the flow path downstream of the fluid channel 260'.

Figure 35:
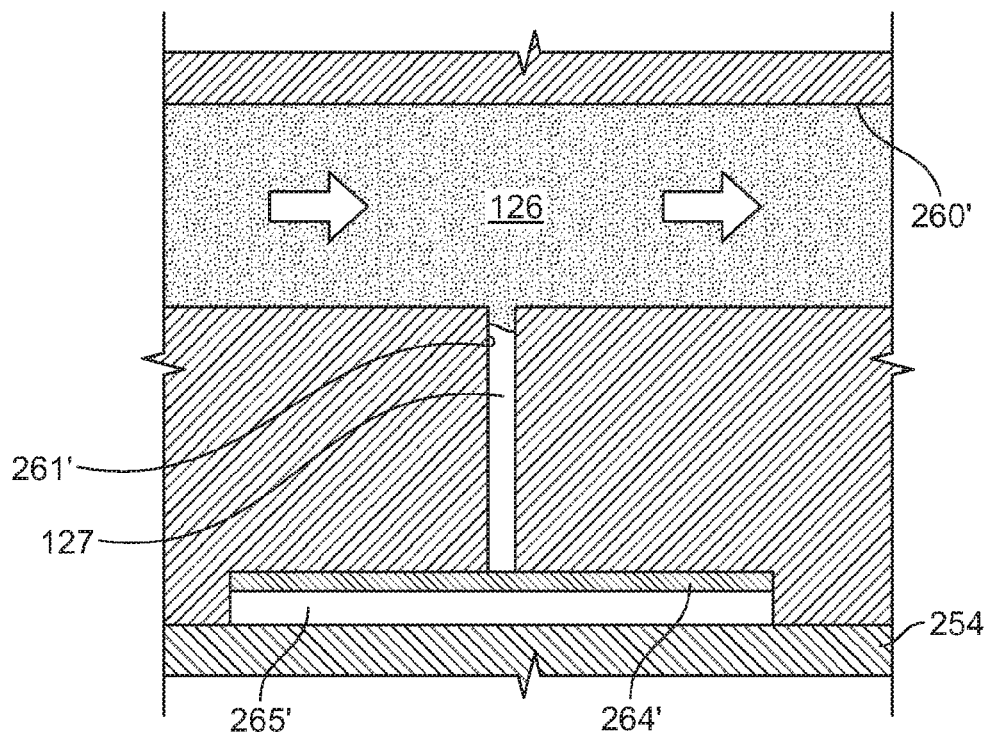
FIGS. 35-36 are cross-sectional views of a portion of a fluid channel through the cap device of FIG. 34, in accordance with some embodiments.
Figure 36:
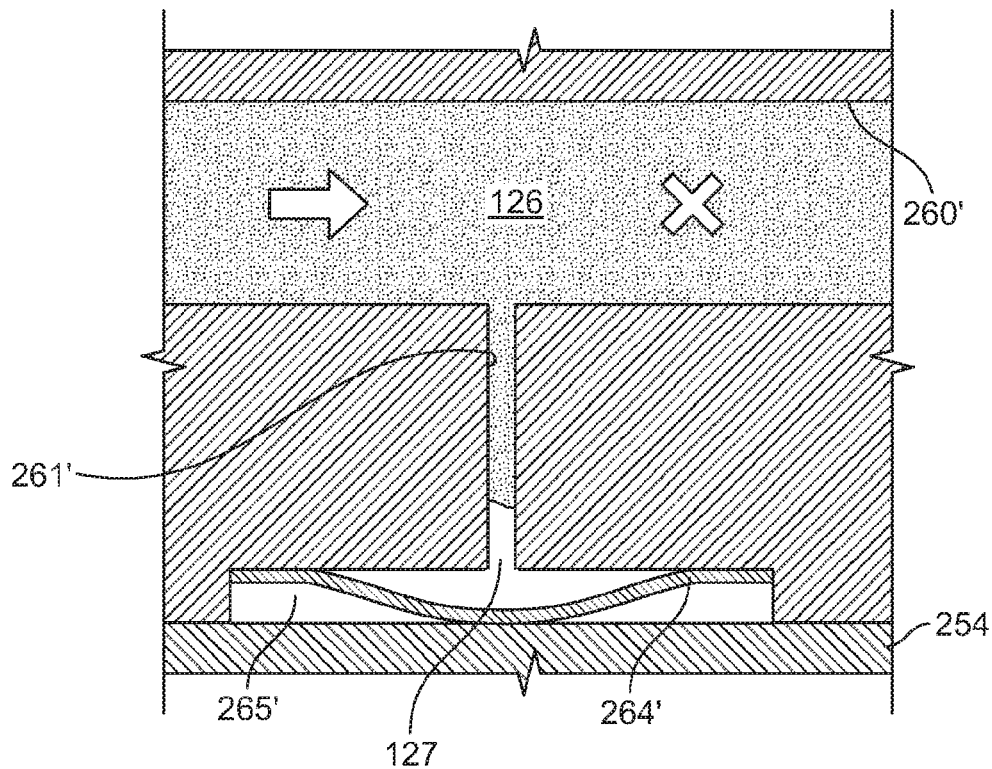

Referring now to FIGS. 35-36 (which show a closer view of the capillary tube 261' and flexible membrane 264' from FIG. 34), a pocket of air 127 can be trapped in the capillary tube 261' to separate the flexible membrane 264' from the flow of medicine 126 through the fluid channel 260'. For example, before the medicine 126 is initially dispensed through the fluid channel 260' and to the infusion set tubing 147 (FIG. 34), the fluid channel 260' and the capillary tube 261' may have air therein. When the pump device 100 (FIG. 1) is activated to dispensing medicine 126 from the cartridge 120 (FIG. 34) (e.g., during a priming operation or the like), the medicine 126 is delivered through the fluid channel 260' along the flow path to the infusion set tubing 147 (FIG. 34). When the medicine 126 is forced through the fluid channel 260', the pocket of air 127 can be trapped in the capillary tube 261' so as to separate the medicine 126 in the flow path from the flexible membrane 264'.

As shown in FIG. 35, during normal operation, the medicine 126 can move along the flow path through the fluid channel 260' and to the infusion set tubing 147 (FIG. 34) for dispensation to the user. In such circumstances, the fluid pressure of the medicine 126 is maintained within a normal operating range because the infusion set tubing 147 (FIG. 34) or other part of the flow path is not kinked, clogged, or otherwise occluded. Because the fluid pressure of the medicine 126 is within the normal operating range, the air pocket 127 in the capillary tube 261' is also maintained within the normal operating range. Because the fluid pressure of the air pocket 127 in the capillary tube 261' is below a particular level, the flexible membrane 264' that is adjacent to the capillary tube 261' is not substantially deformed (e.g., the membrane 264' does not flex downwardly into the air cavity 265' to abut the internal light transmissive member 254). As previously described, the light from the light emitter 253 can be reflected at the interface where the internal light transmissive member 254 meets the air cavity 265'.

As shown in FIG. 36, when an occlusion exists in the flow path, the fluid pressure of the medicine 126 passing through the cap device 130 may rise to a level above the normal operating range. For example, if pump device 100 attempts to dispense another incremental dosage medicine when the infusion set tubing 147 (FIG. 34) is clogged or kinked, the fluid pressure upstream of the occlusion (e.g., in the fluid channel 260') may be increased. In these circumstances, the air pocket 127 trapped in the capillary tube 261' may be compressed due to the added pressure from the medicine 126. The increased pressure in the air pocket 127 can cause the flexible membrane 264' to be substantially deformed (e.g., the membrane 264' will flex downwardly into the air cavity 265' to abut the light transmissive member 254.) Even though some portion of the medicine 126 may advance into the capillary tube 261', the air pocket 127 separates the flexible membrane 264' from the flow path such that the flexible membrane 264' does not contact the medicine 126.

Still referring to FIGS. 35-36, the capillary tube 261' may have an orientation and size such that the medicine forced through the fluid channel 260' (e.g., during an initial priming operation or the like) does not completely fill the capillary tube 261', thereby trapping the air pocket 127 therein. For example, in this embodiment, the capillary tube 261' may extend generally perpendicularly from the longitudinal axis of the fluid channel 261. Furthermore, the capillary tube 261' may have a diameter at the opening that meets the fluid channel 260' which is substantially small than the length of the capillary tube 261'. In one example, the capillary tube 261' may have a length-to-diameter ratio that is greater than about four, greater than about 6, greater than about 10, and preferably greater than about twelve. (Note that the capillary tube 261' is not necessarily illustrated in proportion in FIG.

34.) Accordingly, the medicine 126 forced through the fluid channel 260' (e.g., during an initial priming operation or the like) does not advance to the flexible membrane 264' but instead traps the air pocket 127 in the capillary tube 261' as the medicine flows through the channel 260' and to the infusion set tubing 147

Figure 37:
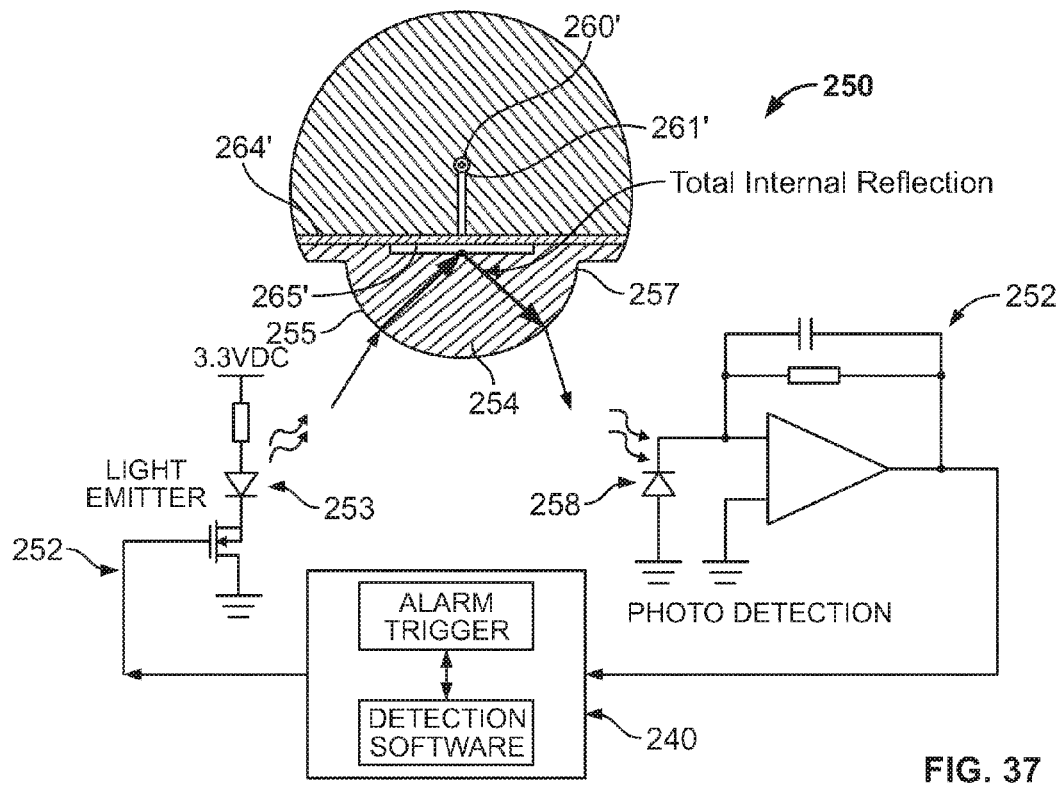
FIGS. 37-38 are diagrams of an alternative embodiment of an occlusion sensor to be arranged adjacent to the cap device of FIG. 34.
Figure 38:
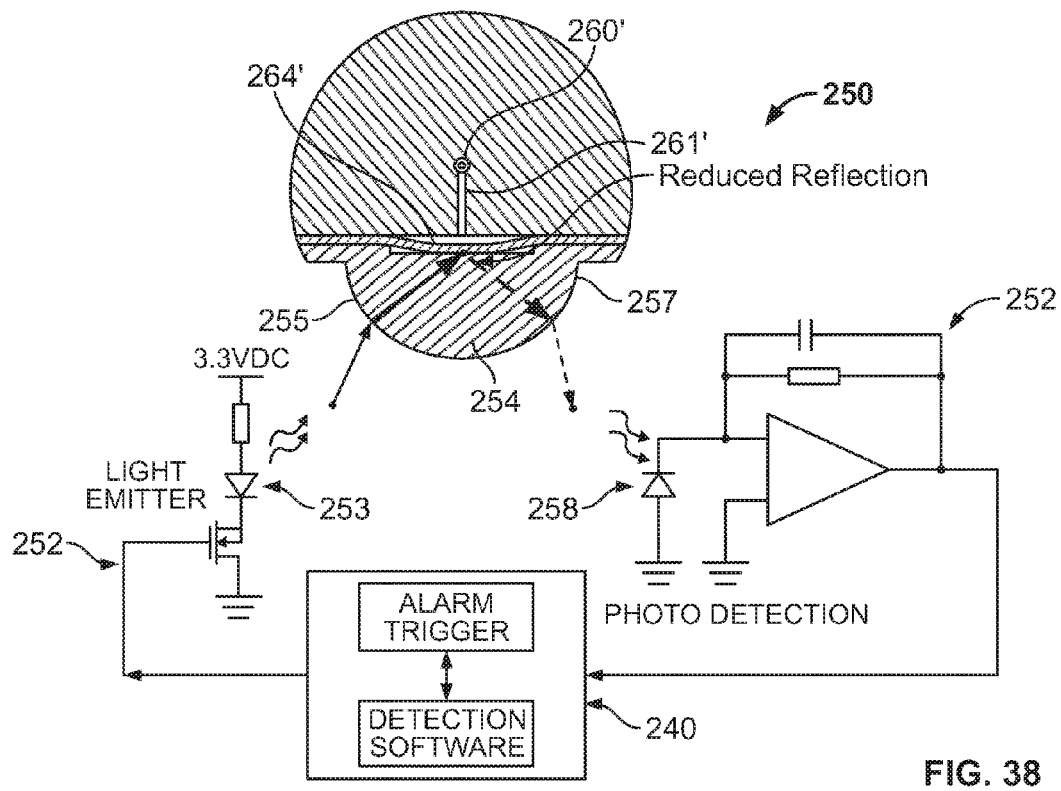

Referring now to FIGS. 37-38, the capillary tube 261' enables the flexible membrane 264' and air cavity 265' to be arranged in a position that is offset from the fluid channel 260', thereby providing a greater angle of incidence for the reflected light within the light transmissive member 254. For example, the embodiment depicted in FIGS. 37-38 illustrates that the flexible membrane 264' and the air cavity 265' are arranged close to the light emitter 253 and light sensor 258 (as compared to the embodiment depicted in FIGS. 32-33). In such circumstances, the light from the light emitter 253 (as directed by surface 255) approaches the interface between the light transmissive member 254 and the air cavity 265' at a greater angle of incidence, thereby facilitating the phenomenon of total internal reflection (refer to FIG. 37). As previously described, total internal reflection can occur in some circumstances when light passes through a first medium (e.g., the internal light transmissive member 254) and strikes an interface between the first medium and a second medium (e.g., the air cavity 265) at an angle of incidence greater than the critical angle. If the refractive index of the second medium (e.g., the air cavity 265) is lower than refractive index of the first medium (e.g., the internal light transmissive member 254), the light can undergo total internal reflection within the first medium.

Similar to embodiments previously described in connection with FIGS. 32-33, the process of determining whether an occlusion exists can be implemented using the control circuitry 240 of the controller device 200. In particular, the control circuitry 240 can be used to activate the light emitter 253 and the light sensor 258 at selected times to monitor the fluid pressure in the flow path. The control circuitry 240 can receive detector signals from the light sensor 258 and thereafter process the data to determine if an alarm should be triggered to notify the user of an occlusion.

As shown in FIG. 37, when no substantial occlusion exists in the flow path, the fluid pressure of the medicine passing through the fluid channel 260' may be within the normal operating range. In these circumstances, the flexible membrane 264' that is adjacent to the capillary tube 261' is not substantially deformed (e.g., the membrane 264' does not flex downwardly into the air cavity 265' to abut the internal light transmissive member 254). As such, the light from the light emitter 253 can pass through the light transmissive member 254, and then reflect at the interface where the internal light transmissive member 254 meets the air cavity 265. This light reflection may occur due to total internal reflection at the interface. This reflected light continues through the internal light transmissive member 254 toward a second curved surface 257, directs the light toward the light sensor 258. As previously described, in some embodiments, the light sensor 258 may comprise an infrared photo detector that is capable of converting the receipt of infrared light into electrical signals. These electrical signals from the light sensor 258 can be transmitted via the sensor circuit 252 to the control circuitry 240. The control circuitry 240 receives the signals from the light sensor 258 and uses this data to determine if an occlusion alarm should be provided to the user. In this example depicted in FIG. 37, the control circuitry 240 receives signals that indicate the pressure in the fluid channel 260 is within the normal operating range, so the control circuitry would not trigger an alarm for the user.

As shown in FIG. 38, when an occlusion exists in the flow path, the fluid pressure of the medicine passing through the cap device 130 may rise to a level above the normal operating range. As such, the air pocket 127 (FIGS. 35-36) in the capillary tube 261' may act upon the flexible membrane 264' to substantially deform it (e.g., the membrane 264' will flex downwardly into the air cavity 265' to abut the light transmissive member 254.) As previously described, the interface where the light transmissive member 254 meets the flexible membrane 264' provides different optical results than the previously described interface where the light transmissive member 254 meets the air cavity 265' (FIG. 37). In particular, the amount of light from the light emitter 253 that is internally reflected at the interface where the light transmissive member 254' meets the flexible membrane 264' is measurably less (as illustrated by the dotted lines in FIG. 38).

The light that is not internally reflected at this interface may pass into the medium of flexible membrane 264' and perhaps into the capillary tube 261'. For example, the refractive index of the material of the flexible membrane 264' can be substantially similar to that of the material of the light transmissive member 254. As a result, the light being transmitted through the light transmissive member 254 can pass into the flexible membrane 264' when the membrane 264' flexes into the air cavity 265' and contacts the flat surface of the light transmissive member 254. The light from the light emitter 253 does not undergo total internal reflection at the portion where the flexible membrane 264' interfaces with light transmissive member 254, thereby resulting in reduced amount of light received by the light sensor 258. If any portion of the light is internally reflected, this reduced portion of reflected light continues through the light transmissive member 254 toward a second curved surface 257 and then toward the light sensor 258. Because the amount of light that is internally reflected in the light transmissive member 254 is measurably less, the light sensor 258 can produce detection signals that are different from those described in connection with FIG. 37. These detection signals from the light sensor 258 can be transmitted via the sensor circuit 252 to the control circuitry 240. The control circuitry 240 receives the signals from the light sensor 258 and uses this data to determine if an occlusion alarm should be provided to the user. For example, the control circuitry 240 may include the previously described detection software module and the previously described alarm trigger module stored in one or more memory devices (e.g., on the main processor board 242). In this example depicted in FIG. 38, the detection signals may indicate that the fluid pressure in the cap device 130 has risen above the normal operating range due to a downstream occlusion.

In alternative embodiments, the occlusion sensor may include a system other than the optical sensor system 250 described in connection with FIGS. 26-33 and 34-38. For example, the occlusion sensor may comprise a force transducer arranged on the piston rod 370 (FIGS. 22-25) so as to detect changes in the fluid pressure in the medicine cartridge. In such embodiments, the controller device 200 may be configured to receive the signals from the force transducer to determine if an occlusion alarm should be provided to the user. For example, the force transducer signals can be input to the detection software module stored in one or more memory devices (e.g., on the main processor board 242).

In another example, the cap device 130 may house at least a portion of an occlusion sensor that is configured to detect the flow of medicine through the cap device 130 or to detect an occlusion in the fluid path. Such an occlusion sensor housed at least partially in the cap device 130 may include a pair of electrodes surfaces that are arranged to detect fluid flow through the cap device 130. For example, an AC current may be passed through the fluid between the two electrodes, and the electrodes can be configured to sense the electrical admittance (e.g., the inverse of the electrical impedance) through the fluid in the bypass fluid path 166. The electrical admittance sensed using the electrodes can be correlated to a fluid velocity (e.g., a change in the flow speed causes a change in the electrical admittance). In such embodiments, the controller device 200 may be programmed to correlate the fluid velocity from the electrical admittance sensed using the electrodes.

It should be understood from the description herein that, in alternative embodiments, other types of occlusion sensors can operate within the cap device 130 to detect flow (or nonflow) of the medicine. For example, the occlusion sensor housed at least partially in the cap device may include a pressure sensor that indicates the fluid pressure in the cap device 130. For example, a miniature pressure transducer can be arranged in the cap device 130 to detect the fluid pressure. In some cases, the miniature pressure transducer can be formed as a MEMS (Micro-ElectroMechanical System) device. The miniature pressure transducer may be output an electrical signal that can be correlated to a fluid pressure value. In such embodiments, the controller device 200 may be programmed to correlate the fluid pressure from the signal output by the pressure transducer. In another example, the occlusion sensor may include a first probe and a second probe arranged in the cap device 130—the first probe being used to induce a small oxygen ($O_2$) concentration into the fluid flow, and the second probe being used to detect the oxygen level in the fluid flow. If the second probe detects an oxygen concentration greater than a threshold level, the fluid flow may be occluded or partially occluded. As such, the controller device 200 may communicate an alarm to the user that an occlusion exists in the fluid path.

A number of embodiments of the invention have been described. Nevertheless, it will be understood that various modifications may be made without departing from the spirit and scope of the invention. Accordingly, other embodiments are within the scope of the following claims.

What is claimed is:

1. An occlusion sensor system for an infusion pump system including a reusable controller device removably attachable to a disposable pump device, the occlusion sensor system comprising:
   a light emitter and a light sensor in electrical communication with control circuitry of a reusable controller device; and
   a light transmissive member aligned with the light emitter and the light sensor when the reusable controller device is removably attached to a disposable single-use pump device;
   wherein the light sensor receives light from the light emitter that undergoes total internal reflection within the light transmissive member; and
   comprising a flexible membrane arranged in the disposable single-use pump device, the flexible membrane spaced apart from the light transmissive member by a cavity when in a first operative position.

2. The occlusion sensor system of claim 1, wherein when the flexible membrane is in the first operative position, the light from the light emitter undergoes total internal reflection within the light transmissive member at an interface with the cavity.

3. The occlusion sensor system of claim 2, wherein in response to a flow condition in a flow path extending from the disposable single-use pump device, the flexible membrane is adjustable to a second operative position in which the flexible membrane abuts the light transmissive member.

4. The occlusion sensor system of claim 3, wherein when the flexible membrane is in the second operative position, at least a portion the light from the light emitter passes from the light transmissive member and into the flexible membrane at an interface between the light transmissive member and the flexible membrane.

5. A method for detecting an occlusion in a flow path from an infusion pump system, comprising:
   activating a light emitter to direct light into a light transmissive member;
   receiving signals from a light sensor by control circuitry arranged in a controller device housing, the signals from the light sensor being generated in response to the light sensor receiving light from the light emitter that undergoes total internal reflection within the light transmissive member in a region proximate to a flexible membrane, the light transmissive member aligned with the light emitter and a light sensor when the controller device housing is removably attached to a disposable single-use pump device; and
   determining if an occlusion exists in a flow path based at least in part on the signals received from the light sensor.

6. The method of claim 5, wherein the determining step comprises inputting data from the light sensor and executing a comparative process to determine if the occlusion exists.

7. The method of claim 5, further comprising activating a drive system at least partially housed in the pump device so as to force medicine from the pump device and into the flow path.

8. The method of claim 7, wherein the light emitter is activated one or more times shortly before the drive system is activated.

9. An occlusion sensor system for an infusion pump system, the occlusion sensor system comprising:
   a light emitter and a light sensor in electrical communication with control circuitry of the infusion pump system;
   a light transmissive member aligned with the light emitter and the light sensor; and
   a flexible membrane spaced apart from the light transmissive member by a cavity,
   wherein the light sensor receives light from the light emitter that undergoes total internal reflection within the light transmissive member.

10. The occlusion sensor system of claim 9, wherein the light emitter and the light sensor are arranged in a reusable controller device.

11. The occlusion sensor system of claim 10, wherein the light transmissive member is arranged in a disposable single-use pump device removably attached to the reusable controller device.

12. The occlusion sensor system of claim 11, wherein the light transmissive member is arranged in a cap device of the disposable single-use pump device.

13. The occlusion sensor system of claim 12, wherein the light emitter is configured to direct light towards a fluid channel in the cap device of the disposable single-use pump device and the light sensor is configured to receive light reflected from the cap device.

14. The occlusion sensor system of claim 9, wherein the light from the light emitter undergoes total internal reflection within the light transmissive member at an interface with an air cavity adjacent to the light transmissive member.

15. The occlusion sensor system of claim 9, wherein the light emitter is an infrared light emitter.

16. The occlusion sensor system of claim 9, wherein the light emitter and the light sensor are reusable with a series of disposable single-use pump devices.

17. The occlusion sensor system of claim 9, wherein the flexible membrane is arranged in a disposable single-use pump device.

18. The occlusion sensor system of claim 17, wherein the flexible membrane comprises a material having a refractive index that is substantially similar to the light transmissive member.

19. The occlusion sensor system of claim 17, wherein the flexible membrane is separated from a medicine flow path by an air pocket in a capillary tube.

20. The occlusion sensor system of claim 9, wherein the light from the light emitter undergoes total internal reflection within the light transmissive member at an interface with the cavity when the flexible membrane is spaced apart from the light transmissive member by the cavity.

21. The occlusion sensor system of claim 20, wherein in response to a flow condition in a flow path, the flexible membrane is adjustable to at least partially abut the light transmissive member.

22. The occlusion sensor system of claim 21, wherein when the flexible membrane at least partially abuts the light transmissive member, at least a portion the light from the light emitter passes from the light transmissive member and into the flexible membrane at an interface between the light transmissive member and the flexible membrane to reduce an amount of light internally reflected by the light transmissive member and received by the light sensor.

23. The occlusion sensor system of claim 9, wherein the control circuitry receives signals from the light sensor to determine a fluid pressure condition in a flow path extending from the disposable single-use pump device.

24. The occlusion sensor system of claim 23, wherein the control circuitry includes a detection module stored in one or more memory devices, the detection module including instructions that, when executed, performs a comparative process to determine if an occlusion exists.

* * * * *